(12) United States Patent
Tyte et al.

(10) Patent No.: US 8,940,913 B2
(45) Date of Patent: Jan. 27, 2015

(54) HERBICIDES

(75) Inventors: Melloney Tyte, Bracknell (GB); Stephane André Marie Jeanmart, Bracknell (GB); Christopher John Mathews, Bracknell (GB); Louisa Robinson, Bracknell (GB)

(73) Assignee: Syngenta Crop Protection, LLC, Greensboro, NC (US)

( * ) Notice: Subject to any disclaimer, the term of this patent is extended or adjusted under 35 U.S.C. 154(b) by 1308 days.

(21) Appl. No.: 12/671,975

(22) PCT Filed: Aug. 7, 2008

(86) PCT No.: PCT/EP2008/006496
§ 371 (c)(1),
(2), (4) Date: Oct. 14, 2011

(87) PCT Pub. No.: WO2009/019015
PCT Pub. Date: Feb. 12, 2009

(65) Prior Publication Data
US 2012/0142529 A1  Jun. 7, 2012

(30) Foreign Application Priority Data

Aug. 9, 2007 (GB) .................................. 0715576.5

(51) Int. Cl.
*C07D 493/08* (2006.01)
*C07D 493/04* (2006.01)

(52) U.S. Cl.
CPC ............ *C07D 493/04* (2013.01); *C07D 493/08* (2013.01)
USPC ...................................................... 549/459

(58) Field of Classification Search
CPC .................................................. C07D 493/08
USPC ...................................................... 549/459
See application file for complete search history.

(56) References Cited

U.S. PATENT DOCUMENTS

| | | | |
|---|---|---|---|
| 4,175,135 A | 11/1979 | Haines et al. | |
| 4,209,532 A | 6/1980 | Wheeler | |
| 4,256,659 A | 3/1981 | Wheeler | |
| 4,283,348 A | 8/1981 | Wheeler | |
| 4,338,122 A | 7/1982 | Wheeler | |
| 4,371,711 A | 2/1983 | Saito et al. | |
| 4,409,153 A | 10/1983 | Hodakowski et al. | |
| 4,436,666 A * | 3/1984 | Wheeler | 558/248 |
| 4,489,012 A | 12/1984 | Hodakowski | |
| 4,526,723 A | 7/1985 | Wheeler et al. | |
| 4,551,547 A | 11/1985 | Wheeler | |
| 4,659,372 A | 4/1987 | Wheeler | |
| 4,670,041 A * | 6/1987 | Payne et al. | 504/251 |
| 5,808,135 A | 9/1998 | Fischer et al. | |
| 5,840,661 A | 11/1998 | Fischer et al. | |
| 6,251,833 B1 | 6/2001 | Erdelen et al. | |
| 6,252,093 B1 * | 6/2001 | McMorris | 549/459 |
| 6,358,887 B1 | 3/2002 | Fischer et al. | |
| 6,458,965 B1 | 10/2002 | Lieb et al. | |
| 6,515,184 B1 | 2/2003 | Fischer et al. | |
| 6,569,810 B1 | 5/2003 | Fischer et al. | |
| 6,642,180 B1 | 11/2003 | Fischer et al. | |
| 6,894,005 B1 | 5/2005 | Maetzke et al. | |
| 8,058,210 B2 | 11/2011 | Lieb et al. | |
| 8,084,649 B2 | 12/2011 | Muehlebach et al. | |
| 8,530,388 B2 | 9/2013 | Whittingham et al. | |
| 8,530,667 B2 | 9/2013 | Jeanmart et al. | |
| 2003/0199572 A1 | 10/2003 | Lieb et al. | |
| 2003/0216260 A1 | 11/2003 | Ruther et al. | |
| 2005/0164883 A1 | 7/2005 | Maetzke et al. | |
| 2006/0058194 A1 | 3/2006 | Fischer et al. | |
| 2006/0166829 A1 | 7/2006 | Fischer et al. | |
| 2007/0015664 A1 | 1/2007 | Fischer et al. | |
| 2007/0298968 A1 | 12/2007 | Bretschneider et al. | |
| 2008/0167188 A1 | 7/2008 | Fischer et al. | |
| 2009/0137393 A1 | 5/2009 | Fischer et al. | |
| 2009/0227563 A1 | 9/2009 | Fischer et al. | |
| 2009/0239906 A1 | 9/2009 | Fischer et al. | |
| 2009/0298828 A1 | 12/2009 | Fischer et al. | |
| 2009/0305891 A1 | 12/2009 | Fischer et al. | |
| 2010/0009850 A1 | 1/2010 | Fischer et al. | |

(Continued)

FOREIGN PATENT DOCUMENTS

| | | |
|---|---|---|
| CA | 2322158 | 8/2000 |
| CA | 2325526 | 9/2000 |

(Continued)

OTHER PUBLICATIONS

M. Muehlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.

(Continued)

*Primary Examiner* — Andrew D Kosar
*Assistant Examiner* — Raymond Covington
(74) *Attorney, Agent, or Firm* — R. Kody Jones

(57) ABSTRACT

Compounds of formula (I), wherein the substituents are as defined in claim 1, are suitable for use as herbicides.

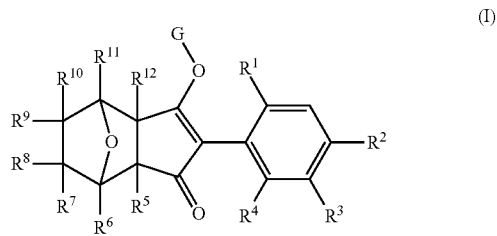

(I)

20 Claims, No Drawings

(56) References Cited

U.S. PATENT DOCUMENTS

| | | |
|---|---|---|
| 2010/0029814 A1 | 2/2010 | Inbe et al. |
| 2010/0113270 A1 | 5/2010 | Mathews et al. |
| 2010/0210466 A1 | 8/2010 | Muehlebach et al. |
| 2010/0216638 A1 | 8/2010 | Mathews et al. |
| 2011/0263428 A1 | 10/2011 | Jeanmart et al. |
| 2012/0002191 A1 | 1/2012 | Van Neste et al. |
| 2012/0002880 A1 | 1/2012 | Lipson et al. |
| 2012/0009483 A1 | 1/2012 | Chu et al. |
| 2012/0065064 A1 | 3/2012 | Taylor et al. |
| 2012/0065066 A1 | 3/2012 | Mathews et al. |
| 2012/0094832 A1 | 4/2012 | Tyte et al. |
| 2012/0142529 A1 | 6/2012 | Tyte et al. |

FOREIGN PATENT DOCUMENTS

| | | |
|---|---|---|
| CA | 2382432 | 2/2002 |
| CA | 2382435 | 2/2002 |
| CA | 2404868 | 9/2002 |
| CA | 2456776 | 2/2004 |
| CA | 2636352 | 7/2008 |
| DE | 2813341 | 4/1983 |
| WO | 9601798 | 1/1996 |
| WO | 9603366 | 2/1996 |
| WO | 9625395 | 8/1996 |
| WO | 9635664 | 11/1996 |
| WO | 9714667 | 4/1997 |
| WO | 9839281 | 9/1998 |
| WO | 9943649 | 9/1999 |
| WO | 9947525 | 9/1999 |
| WO | 9948869 | 9/1999 |
| WO | 0015615 | 3/2000 |
| WO | 0047585 | 8/2000 |
| WO | 0109092 | 2/2001 |
| WO | 0117972 | 3/2001 |
| WO | 0117973 | 3/2001 |
| WO | 0174770 | 10/2001 |
| WO | 03132249 | 2/2003 |
| WO | 2004037749 | 5/2004 |
| WO | 2004058712 | 7/2004 |
| WO | 2004080962 | 9/2004 |
| WO | 2004111042 | 12/2004 |
| WO | 2005092897 | 10/2005 |
| WO | 2005123667 | 12/2005 |
| WO | 2006024411 | 3/2006 |
| WO | 2006029799 | 3/2006 |
| WO | 2007068427 | 6/2007 |
| WO | 2007080066 | 7/2007 |
| WO | 2007096058 | 8/2007 |
| WO | 2007121868 | 11/2007 |
| WO | 2007140881 | 12/2007 |
| WO | 2008071405 | 6/2008 |
| WO | 2008110307 | 9/2008 |
| WO | 2008110308 | 9/2008 |
| WO | 2008145336 | 12/2008 |
| WO | 2009019015 | 2/2009 |
| WO | 2009304450 | 3/2009 |
| WO | 2010000773 | 1/2010 |
| WO | 2010133232 | 11/2010 |

OTHER PUBLICATIONS

J. Wenger and T. Nidermann, "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

J. Wenger, T. Nidermann and C. Mathews, "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

W. Ried et al., "Ringweiterungen and Umlagerungen von 3-alkyl-4-phenylcyclobutendionen", Chemische Berichte, vol. 115, 1982, pp. 783-790 (see p. 785 compound 7).

Zora et al., Organomettallics, vol. 18, No. 21, 1999, pp. 4429-4436 (see p. 4430, compds 45D-4H).

Chemical Abstracts Reg. No. 52833-96-7, Jun. 11, 2003, "4-cyclopentene-1,3-dione, 2-(5-chloro-2-methoxyphenyl)".

Chemical Abstracts Reg. No. 299968-82-4, Oct. 27, 2000, "4-cyclopentene-1,3-dione, 2-(2-bromophenyl)".

* cited by examiner

HERBICIDES

This application is a 371 of International Application No. PCT/EP2008/006496 filed Apr. 7, 2008, which claims priority to GB 0715576.5 filed Aug. 9, 2007, the contents of which are incorporated herein by reference.

The present invention relates to novel, herbicidally active cyclopentanedione compounds, and derivatives thereof, to processes for their preparation, to compositions comprising those compounds, and to their use in controlling weeds, especially in crops of useful plants, or in inhibiting undesired plant growth.

Cyclopentanedione compounds having herbicidal action are described, for example, in WO 01/74770 and WO 96/03366.

Novel cyclopentanedione compounds, and derivatives thereof, having herbicidal and growth-inhibiting properties have now been found.

The present invention accordingly relates to compounds of formula I

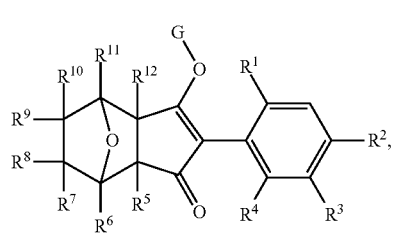

(I)

wherein $R^1$ is methyl, ethyl, n-propyl, isopropyl, halomethyl, haloethyl, halogen, vinyl, ethynyl, methoxy, ethoxy, halomethoxy, haloethoxy or cyclopropyl, $R^2$ and $R^3$ are independently of each other hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, optionally substituted aryl or optionally substituted heteroaryl, where at least one of $R^2$ and $R^3$ is optionally substituted aryl or optionally substituted heteroaryl, $R^4$ is hydrogen, methyl, ethyl, n-propyl, isopropyl, halomethyl, haloethyl, halogen, vinyl, ethynyl, methoxy, ethoxy, halomethoxy or haloethoxy, $R^5$ and $R^{12}$ are independently of each other hydrogen, $C_1$-$C_3$alkyl, $C_1$-$C_3$haloalkyl, $C_1$-$C_3$alkoxy, $C_1$-$C_3$alkylthio, halogen or $C_1$-$C_6$alkoxycarbonyl, or $R^5$ and $R^{12}$ join together to form a 3-7 membered carbocyclic ring, optionally containing an oxygen or sulfur atom, and $R^6$, $R^7$, $R^8$, $R^9$, $R^{10}$ and $R^{11}$ are independently of each other hydrogen or a aubstituent, or $R^7$ and $R^8$ or $R^9$ and $R^{10}$, together with the carbon atoms to which they are attached form a keto, or optionally substituted imino or optionally substituted alkenyl unit, or any two of $R^7$, $R^8$, $R^9$ and $R^{10}$ together form a 3-8 membered carbocyclic ring optionally containing a heteroatom selected from O, S or N and optionally substituted, or $R^7$ and $R^{10}$ together form a bond, and G is hydrogen, an alkali metal, alkaline earth metal, sulfonium, ammonium or a latentiating group.

In the substituent definitions of the compounds of the formula I, each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$ to $C_6$ alkyl groups, but are preferably $C_1$-$C_4$ alkyl and, more preferably, $C_1$-$C_2$alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that alkenyl and alkylinylalkenyl are included in these terms.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" preferably refers to phenyl and naphthyl. The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, ebenzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidinyl, triazinyl, thienyl, furyl, oxazolyl, isoxazolyl, 2,1,3-benzoxadiazolyl and thiazolyl.

Cycloalkyl includes preferably cyclopropyl, cyclobutyl, cyclopentyl and cyclohexyl. Cycloalkylalkyl is preferentially cyclopropylmethyl. Cycloalkenyl includes cyclopentenyl and cyclohexenyl.

Carbocyclic rings such as those formed together by any two of $R^7$, $R^8$, $R^9$ and $R^{10}$ include cycloalkyl and cycloalkenyl groups with up to 7 atoms, optionally including one or more, preferably 1 or 2 heteroatoms selected from O, S and N leading to heterocycles such as 1,3-dioxolane, oxetane, tetrahydrofuran, morpholine, thiomorpholine and piperazine.

When present, the optional substituents on aryl, heteroaryl, cycloalkyl or heterocyclyl are selected independently, from halogen, nitro, cyano, rhodano, isothiocyanato, $C_{1-6}$ alkyl, $C_{1-6}$haloalkyl, $C_{1-6}$ alkoxy-($C_{1-6}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$) alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, mercapto, $C_{1-10}$ alkylthio, $C_{1-10}$ haloalkylthio, aryl($C_{1-4}$)alkylthio, $C_{3-7}$ cycloalkylthio (where the cycloalkyl group is optionally substituted with $C_{1-6}$ alkyl or halogen), tri($C_{1-4}$)-alkylsilyl($C_{1-6}$)-alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include arylcarbonylamino (where the aryl group is substituted by $C_{1-6}$ alkyl or halogen), ($C_{1-6}$) alkoxycarbonylamino ($C_{1-6}$)alkoxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonylamino, di($C_{1-6}$) alkylaminocarbonylamino, arylaminocarbonylamino where the aryl group is substituted by $C_{1-6}$ alkyl or halogen), aryl-N—($C_{1-6}$)alkylamino-carbonylamino where the aryl group is substituted by $C_{1-6}$ alkyl or halogen), $C_{1-6}$ alkylaminocarbonyl-N—($C_{1-6}$)alkylamino, di($C_{1-6}$)alkylaminocarbonyl-N—($C_{1-6}$)alkylamino, arylaminocarbonyl-N—($C_{1-6}$)alkylamino where the aryl group is substituted by $C_{1-6}$ alkyl or halogen) and aryl-N—($C_{1-6}$)alkylaminocarbonyl-N—($C_{1-6}$)alkylamino where the aryl group is substituted by $C_{1-6}$ alkyl or halogen).

For substituted aryl moieties, heterocyclyl and heteroaryl groups it is particularly preferred that one or more substituents are independently selected from halogen, in particular chloro, cyano, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

The invention relates also to the salts which the compounds of formula I are able to form with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

The latentiating groups G are selected to allow their removal by one or a combination of biochemical, chemical or physical processes to afford compounds of formula I where G is H before, during or following application to the treated area or plants. Examples of these processes include enzymatic cleavage, chemical hydrolysis and photoloysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

Depending on the nature of the substituents G, $R^1$, $R^2$, $R^3$, $R^4$, $R^5$, $R^6$, $R^7$ and $R^8$, compounds of formula I may exist in different isomeric forms. When G is hydrogen, for example, compounds of formula I may exist in different tautomeric forms. Also, when substituents contain double bonds, cis- and trans-isomers can exist. This invention covers all such isomers and tautomers and mixtures thereof in all proportions. These isomers, too, are within the scope of the claimed compounds of the formula I.

It should be understood that in those compounds of formula I where G is a metal, ammonium (such as $NH_4+$; $N(alkyl)_4+$) or sulfonium (such as $S(alkyl)_3+$) cation, the corresponding negative charge is largely delocalised across the O—C=C—C=O unit.

In a preferred group of compounds of the formula I, $R^1$ is methyl, ethyl, vinyl, ethynyl, cyclopropyl, difluoromethoxy or trifluoromethoxy. More preferably, $R^1$ is methyl or ethyl.

Preferably, $R^2$ and $R^3$ are independently of each other hydrogen, optionally substituted phenyl, optionally substituted naphthyl or optionally substituted heteroaryl. More preferably, $R^2$ and $R^3$ are independently of each other hydrogen, phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, heteroaryl or heteroaryl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano.

It is particularly preferred, that $R^2$ is hydrogen and $R^3$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, or that $R^2$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano and $R^3$ is hydrogen.

Preference is given to those phenyl groups $R^2$ and $R^3$, which are substituted by fluoro, chloro, bromo, especially fluoro or chloro, in the 4-position.

Preferably, $R^4$ is hydrogen, methyl, ethyl, vinyl or ethynyl. More preferably, $R^4$ is hydrogen, methyl or ethyl.

In preferred compounds of the formula I $R^5$ and $R^{12}$ are independently of each other hydrogen or $C_1$-$C_3$alkyl, where, more preferably, $R^5$ and $R^{12}$ are hydrogen.

Preferably, in the compounds of the formula I, $R^6$ and $R^{11}$ are independently of each other hydrogen, halogen, formyl, cyano or nitro or
$R^6$ and $R^{11}$ are independently of each other $C_1$-$C_6$alkyl, $C_2$-$C_6$alkenyl, $C_2$-$C_6$alkynyl, $C_1$-$C_6$alkoxy, $C_3$-$C_7$ cycloalkyl, $C_3$-$C_7$ cycloalkenyl, phenyl, heteroaryl or a 3-7 membered heterocyclyl, where all these substituents are optionally substituted, or
$R^6$ and $R^{11}$ are independently of each other a group $COR^{13}$, $CO_2R^{14}$ or $CONR^{15}R^{16}$, $CR^{17}$=$NOR^{18}$, $CR^{19}$=$NNR^{20}R^{21}$, $NHR^{22}$, $NR^{22}R^{23}$ or $OR^{24}$, wherein
$R^{13}$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted,
$R^{14}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted,
$R^{15}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted,
$R^{16}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, phenylsulfonyl, heteroarylsulfonyl, amino, $C_1$-$C_6$alkylamino, di$C_1$-$C_6$alkylamino, phenyl, heteroaryl or a 3-7 membered heterocyclyl, where all these substituents are optionally substituted, or
$R^{15}$ and $R^{16}$ may be joined to form an optionally substituted 3-7 membered ring, optionally containing an oxygen, sulfur or nitrogen atom,
$R^{17}$ and $R^{16}$ are independently of each other hydrogen, $C_1$-$C_3$alkyl or $C_3$-$C_6$cycloalkyl,
$R^{18}$, $R^{20}$ and $R^{21}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, aminocarbonyl, $C_1$-$C_6$alkylaminocarbonyl, di$C_1$-$C_6$alkylaminocarbonyl, phenyl or heteroaryl, where all these substituents are optionally substituted,
$R^{22}$ is $C_1$-$C_6$alkoxycarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenylcarbonyl, phenoxycarbonyl, phenylaminocarbonyl, phenylthiocarbonyl, phenylsulfonyl, heteroarylcarbonyl, heteroaryloxycarbonyl, heteroarylaminocarbonyl, heteroarylthiocarbonyl or heteroarylsulfonyl, where all these substituents are optionally substituted,
$R^{23}$ is $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl, where all these substituents are optionally substituted, or
$R^{22}$ and $R^{23}$ may be joined to form an optionally substituted 3-7 membered ring, optionally containing an oxygen, sulfur or nitrogen atom, where all these substituents are optionally substituted, and
$R^{24}$ is $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, aminocarbonyl, $C_1$-$C_6$alkylaminocarbonyl, di$C_1$-$C_6$alkylaminocarbonyl, $C_1$-$C_6$alkylsulfonyl, tri($C_1$-$C_6$alkyl)silyl, phenyl or heteroaryl, where all these substituents are optionally substituted.

More preferably, $R^6$ and $R^{11}$ are independently of each other hydrogen, halogen, cyano, optionally substituted $C_1$-$C_6$alkyl or a group $COR^{13}$, $CO_2R^{14}$ or $CONR^{15}R^{16}$, $CR^{17}$=$NOR^{18}$ or $CR^{19}$=$NNR^{20}R^{21}$, wherein
$R^{13}$, $R^{14}$, $R^{15}$, and $R^{16}$ are $C_1$-$C_6$alkyl,
$R^{17}$ and $R^{19}$ are hydrogen or $C_1$-$C_3$ alkyl,
$R^{18}$ is $C_1$-$C_3$ alkyl, and
$R^{20}$ and $R^{21}$ are independently of each other hydrogen or $C_1$-$C_3$alkyl, where
$R^6$ and $R^{11}$ being independently of each other hydrogen, methyl or methyl substituted by $C_1$-$C_3$alkoxy is particularly preferred.

Preference is given to compounds of formula I wherein $R^7$, $R^8$, $R^9$ and $R^{10}$ are independently of each other hydrogen, halogen, hydroxyl, formyl, amino, cyano or nitro, or
$R^7$, $R^8$, $R^9$ and $R^{10}$ are independently of each other $C_1$-$C_6$alkyl, $C_2$-$C_6$alkenyl, $C_2$-$C_6$alkynyl, $C_1$-$C_6$alkoxy, $C_1$-$C_6$alkylthio, $C_1$-$C_6$alkylsulfonyl, $C_3$-$C_7$ cycloalkyl, $C_4$-$C_7$cycloalkenyl, tri($C_1$-$C_6$alkyl)silyl, phenyl, heteroaryl or a 3-7 membered heterocyclyl, where all these substituents are optionally substituted, or
$R^7$, $R^8$, $R^9$ and $R^{10}$ are independently of each other a group $COR^{13}$, $CO_2R^{14}$ or $CONR^{15}R^{18}$, $CR^{17}$=$NOR^{18}$, $CR^{19}$=$NNR^{20}R^{21}$, $NR^{22}R^{23}$ or $OR^{24}$, wherein
$R^{13}$ is $C_1$-$C_6$alkyl, $C_2$-$C_6$alkenyl, $C_2$-$C_6$alkynyl, $C_3$-$C_7$ cycloalkyl, $C_5$-$C_7$cycloalkenyl, phenyl, heteroaryl or a 3-7 membered heterocyclyl, where all these substituents are optionally substituted,
$R^{14}$ is hydrogen, $C_1$-$C_6$alkyl, $C_3$-$C_6$alkenyl, $C_3$-$C_6$alkynyl, $C_3$-$C_7$ cycloalkyl, $C_5$-$C_7$cycloalkenyl, phenyl, heteroaryl or is 3-7 membered heterocyclyl, where all these substituents are optionally substituted, $R^{15}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, phenyl, heteroaryl or a 3-7 membered heterocyclyl, where all these substituents are optionally substituted, $R^{16}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$cycloalkenyl, $C_1$-$C_6$alkylsulfonyl, amino, $C_1$-$C_6$alkylamino, di$C_1$-$C_6$alkylamino, phenyl, heteroaryl or a 3-7 membered heterocyclyl, where all these substituents are optionally substituted, or $R^{15}$ and $R^{16}$ may be joined to form an optionally substituted 3-7 membered ring, optionally containing an oxygen, sulfur or nitrogen atom, $R^{17}$ and $R^{19}$ are independently of each other hydrogen, $C_1$-$C_3$alkyl or $C_3$-$C_6$cycloalkyl, $R^{18}$, $R^{20}$ and $R^{21}$ are independently of each other hydrogen, $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, phenyl or heteroaryl, where all these substituents are optionally substituted, $R^{22}$ and $R^{23}$ are independently of each other $C_1$-$C_6$alkyl, $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl or $R^{22}$ and $R^{23}$ may be joined to form an optionally substituted 3-7 membered ring, optionally containing an oxygen, sulfur or nitrogen atom, where all these substituents are optionally substituted, and $R^{24}$ is $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, tri($C_1$-$C_6$alkyl)silyl, phenyl or heteroaryl, where all these substituents are optionally substituted.

More preferably, $R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, 3-7 membered heterocyclyl or $CR^{17}$=$NOR^{18}$, wherein $R^{17}$ is hydrogen or $C_1$-$C_3$ alkyl and $R^{18}$ is $C_1$-$C_3$ alkyl.

It is especially preferred that $R^7$, $R^8$, $R^9$ and $R^{10}$ are independently of each other hydrogen, $C_1$-$C_6$alkyl, $C_2$-$C_6$alkenyl, $C_1$-$C_6$alkoxy or $C_1$-$C_6$alkoxy$C_1$-$C_6$alkyl.

In a group of preferred compounds of the formula I $R^7$ and $R^8$ together form a unit =O, or form a unit =$CR^{25}R^{26}$, or form a unit =$NR^{27}$, or form together with the carbon atom to which they are attached a 3-8 membered ring, optionally containing a heteroatom selected from O, S or N and optionally substituted by $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, $C_1$-$C_3$haloalkyl, halogen, phenyl, phenyl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, $C_1$-$C_4$alkoxycarbonyl, aminocarbonyl, $C_1$-$C_6$alkylaminocarbonyl, di$C_1$-$C_6$alkylaminocarbonyl, halogen, cyano or by nitro, heteroaryl or heteroaryl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, halogen, cyano or by nitro, wherein $R^{25}$ and $R^{26}$ are independently of each other hydrogen, halogen, cyano or nitro, or $R^{25}$ and $R^{26}$ are independently of each other $C_1$-$C_6$alkyl, $C_1$-$C_6$alkoxy, $C_1$-$C_6$alkylamino, di$C_1$-$C_6$alkylamino, $C_1$-$C_6$alkylcarbonyl, $C_1$-$C_6$alkoxycarbonyl, $C_1$-$C_6$alkylaminocarbonyl, di$C_1$-$C_6$alkylaminocarbonyl, N-phenyl-N—$C_1$-$C_6$alkylaminocarbonyl, N-phenyl$C_1$-$C_6$alkyl-N—$C_1$-$C_6$alkylaminocarbonyl, N-heteroaryl-N—$C_1$-$C_6$alkylaminocarbonyl, N-heteroaryl$C_1$-$C_6$alkyl-N—$C_1$-$C_6$alkylaminocarbonyl, phenyl, heteroaryl, $C_3$-$C_8$cycloalkyl or 3-7 membered heterocyclyl, where all these substituents are optionally substituted, or $R^{25}$ and $R^{26}$ may be joined together to form a 5-8 membered ring optionally containing a heteroatom selected from O, S or N and optionally substituted by $C_1$-$C_2$alkyl or $C_1$-$C_2$alkoxy, $R^{27}$ is nitro or cyano, or $R^{27}$ is $C_1$-$C_6$alkylamino, di$C_1$-$C_6$alkylamino, $C_1$-$C_6$alkoxy, $C_3$-$C_6$alkenyloxy, $C_3$-$C_6$alkynyloxy, phenoxy, phenylamino, N-phenyl-N—$C_1$-$C_6$alkylamino, N-phenyl$C_1$-$C_6$alkyl-N—$C_1$-$C_6$alkylamino heteroaryloxy, heteroarylamino, N-heteroaryl-N—$C_1$-$C_6$alkylamino or N-heteroaryl$C_1$-$C_6$alkyl-N—$C_1$-$C_6$alkylamino, where all these substituents are optionally substituted, where It is particularly preferred, when $R^7$ and $R^8$ together form a unit =O or =$NR^{27}$, wherein $R^{27}$ is $C_{1-3}$alkoxy.

Preference is given to compounds of the formula I, wherein $R^7$ and $R^{10}$ together with the carbon atoms to which they are attached form a saturated 3-4 membered ring, optionally containing a heteroatom or group selected from O, S or $NR^{28}$, and optionally substituted by $C_1$-$C_4$alkyl, $C_1$-$C_4$alkoxy, $C_1$-$C_4$alkylthio, halogen, $C_1$-$C_6$alkylcarbonyl or $C_1$-$C_4$alkoxycarbonyl, or $R^7$ and $R^{10}$ together with the carbon atoms to which they are attached form a 5-8 membered ring, optionally containing a heteroatom selected from O, S or N, and optionally substituted by $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, $C_1$-$C_3$haloalkyl, halogen, phenyl, phenyl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, $C_1$-$C_4$alkoxycarbonyl, aminocarbonyl, $C_1$-$C_6$alkylaminocarbonyl, di$C_1$-$C_6$alkylaminocarbonyl, halogen, cyano or by nitro, heteroaryl or heteroaryl substituted by $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylcarbonyl, halogen, cyano or by nitro, or $R^7$ and $R^{10}$ together form a bond, wherein $R^{28}$ is hydrogen, $C_1$-$C_6$alkyl, $C_3$-$C_6$alkenyl, $C_3$-$C_6$alkynyl, $C_1$-$C_6$alkoxy, $C_1$-$C_6$alkylcarbonyl, $C_1$-$C_6$alkoxycarbonyl, $C_1$-$C_6$alkylaminocarbonyl, di$C_1$-$C_6$alkylaminocarbonyl, phenoxycarbonyl $C_1$-$C_6$alkylsulfonyl, phenylsulfonyl or heteroaryloxycarbonyl, where all these substituents are optionally substituted.

More preferably, $R^7$ and $R^{10}$ together form a bond.

The latentiating group G is preferably selected from the groups —C($X^a$)—$R^a$, C($X^b$)—$X^c$—$R^b$, C($X^d$)—N($R^c$)—$R^d$, —$SO_2$—$R^e$, —P($X^e$)($R^f$)—$R^g$ or $CH_2$—$X^f$—$R^h$, wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$-nitroalkyl, $C_2$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_5$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_2$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_2$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_8$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

Preferably, G denotes hydrogen, an alkali metal or alkaline earth metal or a latentiating group.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

G as hydrogen is especially preferred.

A compound of formula (I) wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C($X^a$)—$R^a$, C($X^b$)—$X^c$—$R^b$, C($X^d$)—N($R^e$)—$R^d$, —$SO_2$—$R^e$, —P($X^e$)($R^f$)—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, [$R^a$C($X^a$)]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—C($X^d$)—N($R^c$)—$R^d$ (wherein $X^d$ is sulfur and with the proviso that neither $R^c$ or $R^d$ is hydrogen) or a chloroformate, Cl—C($X^b$)—$X^c$—$R^b$, (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$, (wherein $X^b$ and $X^c$ are sulfur), or an isothiocyanate, $R^c$N=C=S, or by sequential treatment with carbon disulfide and an alkylating agent, or with a phosphorylating agent such as a phosphoryl chloride, Cl—P($X^e$)($R^f$)—$R^9$ or with a sulfonylating agent such as a sulfonyl chloride Cl—$SO_2$—$R^e$, preferably in the presence of at least one equivalent of base. Those skilled in the art will recognise that when a compound of formula (A) contains an unsymmetrical dione (for example, where substituents $R^6$ and $R^{11}$ are different), these reactions may produce, in addition to a compound of formula (1), a second compound of formula (1A). This invention covers both a compound of formula (1) and a compound of formula (1A), together with mixtures of these compounds in any ratio.

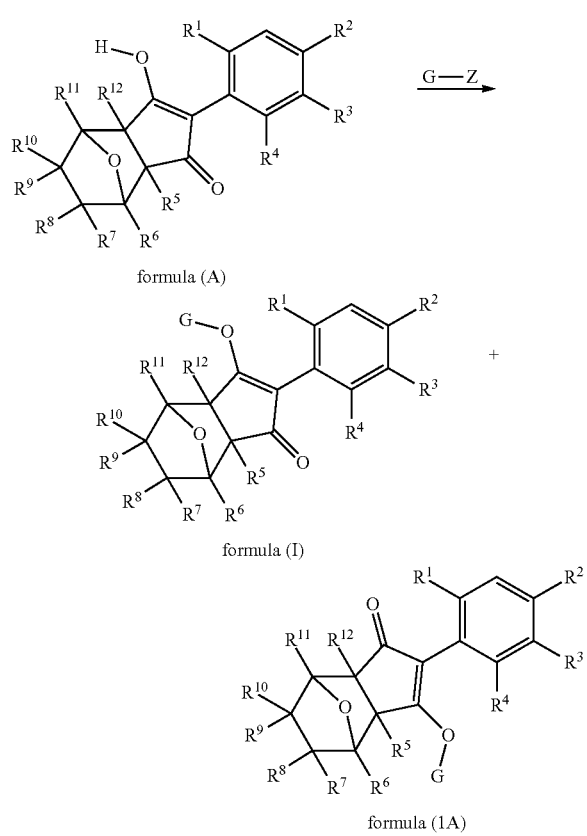

formula (A)

formula (I)

formula (1A)

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425; H. Born et al., J. Chem. Soc., (1953), 1779; M. Constantino et al., Synth. Commun., (1992), 22 (19), 2859; Y. Tian et al., Synth. Commun., (1997), 27 (9), 1577, S. Chandra Roy et al., Chem. Letters, (2006), 35 (1) 16, and P. Zubaidha et al., Tetrahedron Lett., (2004), 45, 7187.

The O-acylation of cyclic 1,3-diones may be effected by procedures similar to those described, for example, by R Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595 and T. Isobe and T. Ishikawa, J. Org. Chem., (1999), 64 (19), 6984.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197.

A compound of formula (A) may be prepared by the cyclisation of a compound of formula (B), wherein R is hydrogen or an alkyl group, preferably in the presence of an acid or base, and optionally in the presence of a suitable solvent, by analogous methods to those described by T. Wheeler, U.S. Pat. No. 4,209,532. The compounds of formula (B) have been particularly designed as intermediates in the synthesis of the compounds of the formula (I). A compound of formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

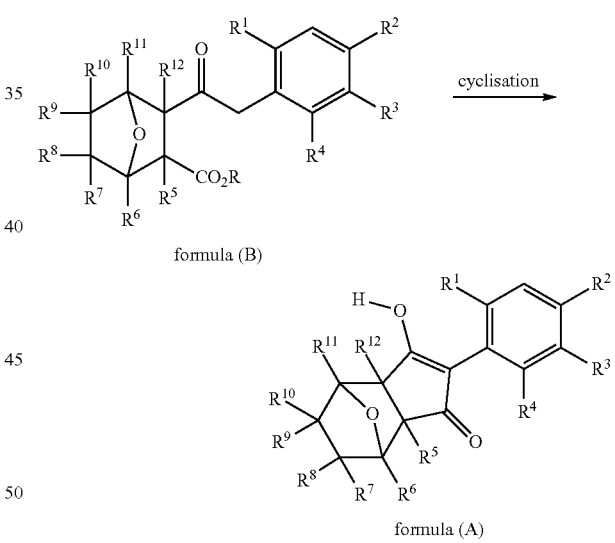

formula (B)

formula (A)

A compound of formula (B) wherein R is alkyl (preferably methyl or ethyl), may be cyclised under acidic or basic conditions, preferably in the presence of at least one equivalent of a strong base such as potassium Pert-butoxide, lithium diisopropylamide or sodium hydride and in a solvent such as tetrahydrofuran, dimethylsulfoxide or N,N-dimethylformamide.

A compound of formula (B), wherein R is H, may be prepared by saponification of a compound of formula (C) wherein R' is alkyl (preferably methyl or ethyl), under standard conditions, followed by acidification of the reaction mixture to effect decarboxylation, by similar processes to those described, for example, by T. Wheeler, U.S. Pat. No. 4,209,532.

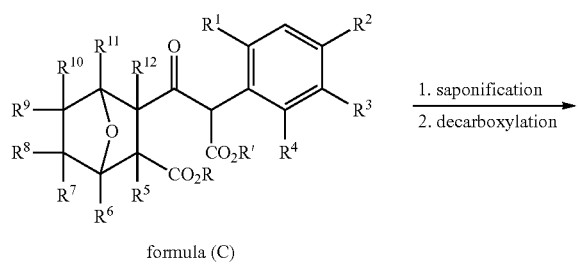

formula (C)

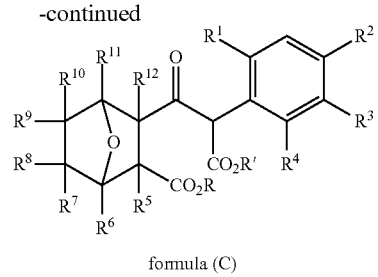

formula (C)

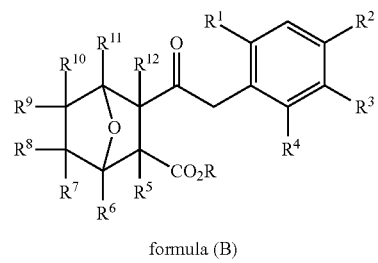

formula (B)

A compound of formula (B), wherein R is H, may be esterified to a compound of formula (B), wherein R is alkyl, under known conditions, for example by heating with an alkyl alcohol, ROH, in the presence of an acid catalyst.

A compound of formula (C), wherein R is alkyl, may be prepared by treating a compound of formula (D) with a suitable carboxylic acid chloride of formula (E) under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C. Alternatively, a compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F):

Compounds of formula (D) are known compounds, or may be prepared from known compounds by known methods (see, for example, R. Fischer et al., WO2004/111042; T. Maetzke, S. Wendeborn and A. Stoller, WO2001/017973; F. Lieb et al., WO99/55673; F. Lieb et al., WO99/043649; I. Bell et al., GB 2326639; JP56125338 and JP56135339 (to Nippon Shinyaku Co. Ltd.); Y. Tamura et al., J. Med. Chem., (1981), 24 (8), 1006).

A compound of formula (E) may be prepared from a compound of formula (F) by treatment with an alkyl alcohol, R—OH, in the presence of a base, such as an alkaline metal alkoxide (see, for example, S. Buser and A. Vasella, Helv. Chim. Acta, (2005), 88, 3151, M. Hart et al., Bioorg. Med. Chem. Letters, (2004), 14, 1969), followed by treatment of the resulting acid with a chlorinating reagent such as oxalyl chloride or thionyl chloride under known conditions (see, for example, C. Santelli-Rouvier. Tetrahedron Lett., (1984), 25 (39), 4371; D. Walba and M. Wand, Tetrahedron Lett., (1982), 23 (48), 4995; J. Cason, Org. Synth. Coll. Vol. III, (1955), 169).

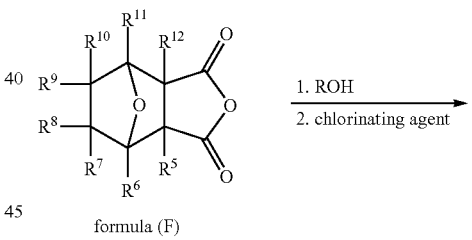

formula (F)

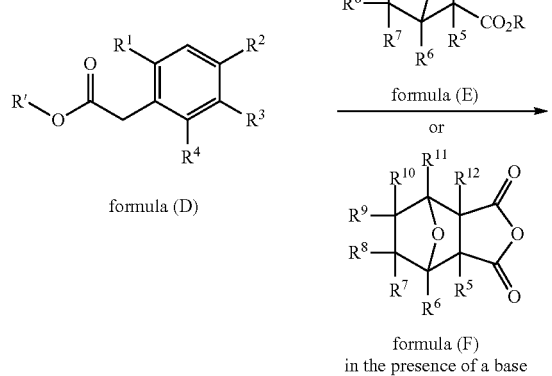

formula (D)

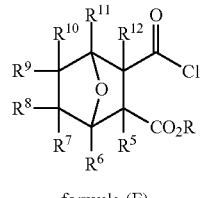

formula (E)

or

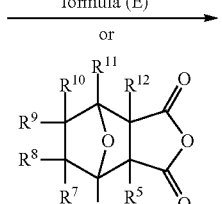

formula (F)
in the presence of a base

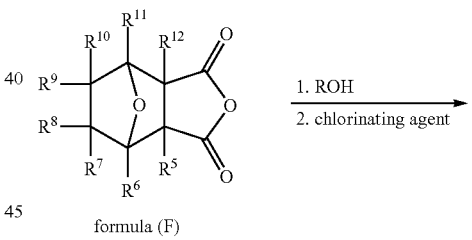

formula (E)

A compound of formula (F) wherein $R^7$ and $R^{10}$ are hydrogen may be prepared by the reduction of a compound of formula (G) under known conditions (see, for example, Y. Baba, N. Hirukawa and M. Sodeoka, Bioorg. Med. Chem. (2005), 13 (17), 5164, M. Hart et al., Bioorg. Med. Chem. Letters, (2004), 14 (18), 1969, Y. Baba, N. Hirukawa, N. Tanohira and M. Sodeoka, J. Am. Chem. Soc., (2003), 125, 9740).

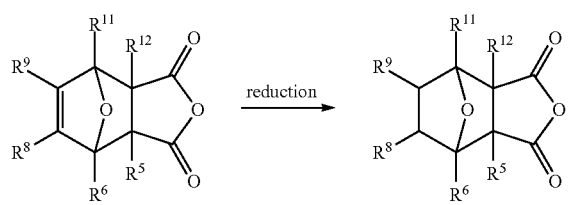

formula (G) → formula (F)

wherein R[7] and R[10] = H

A compound of formula (G) may be prepared by reacting a compound of formula (H) with a maleic anhydride of formula (J), optionally in the presence of a Lewis acid catalyst, according to procedures described, for example, by O. Diels and K. Alder, Liebigs Ann. Chem., (1931), 490, 257; K. Potts and E. Walsh, J. Org. Chem., (1984), 49 (21), 4099; J. Jurczak, T. Kozluk, S. Filipek and S. Eugster, Helv. Chim. Acta, (1982), 65, 1021; W. Dauben, C. Kessel and K. Takemura, J. Am. Chem. Soc., (1980), 102, 6893; A. Pelter and B. Singaram, Tetrahedron Lett., (1982), 23, 245; M. Lee and C. Hemdon, J. Org. Chem., (1978), 43, 518; B. Fisher and J. Hodge, J. Org. Chem. (1964), 29, 776; G. D'Alelio, C. Williams and C. Wilson, J. Org. Chem., (1960), 25, 1028; Z. Song, M. Ho and H. Wong, J. Org. Chem., (1994), 59 (14), 3917-3926; W. Tochtermann, S. Bruhn and C. Wolff, Tetrahedron Lett., (1994), 35(8), 1165-1168; W. Dauben, J. Lam and Z. Guo, J. Org. Chem., (1996), 61(14), 4816-4819; M. Sodeoka, Y. Baba, S. Kobayashi and N. Hirukawa, Bioorg. Med. Chem. Lett., (1997), 7(14) 1833; M. Avalos, R. Babiano, J. Bravo, P. Cintas, J. Jimenez and J. Palacios, Tetrahedron Lett., (1998), 39(50), 9301; J. Auge, R. Gil, S. Kalsey and N. Lubin-Germain, Synlett, (2000), 6, 877; I. Hemeon, C. Deamicis, H. Jenkins, P. Scammells and R. Singer, Synlett, (2002), 11, 1815; M. Essers, B. Wibbeling and G. Haufe, Tetrahedron Lett., (2001), 42 (32), 5429; P. Vogel et al., Tetrahedron Asymmetry, (1996), 7 (11), 3153; Y. Baba, N. Hirukawa, N. Tanohira and M. Sodeoka, J. Am. Chem. Soc., (2003), 125, 9740; L. Ghosez et al., Tetrahedron Lett., (1988), 29 (36), 4573; H. Kotsuki, S. Kitagawa and H. Nishizawa, J. Org. Chem., (1978), 43 (7), 1471; Y. Li et al., J. Org. Chem., (1997), 62 (23), 7926; M. Drew et al., J. Chem. Soc. Perkin Trans. 1, (1985), 1277; R. McDonald and C. Reineke, J. Org. Chem., (1967), 32, 1878; R. Fleming and B. Murray, J. Org. Chem., (1979), 44 (13), 2280; M. Goldstein and G. Thayer Jr. J. Am. Chem. Soc., (1965), 87 (9), 1925 and G. Keglevich et al., J. Organomet. Chem., (1999), 579, 182 and references therein.

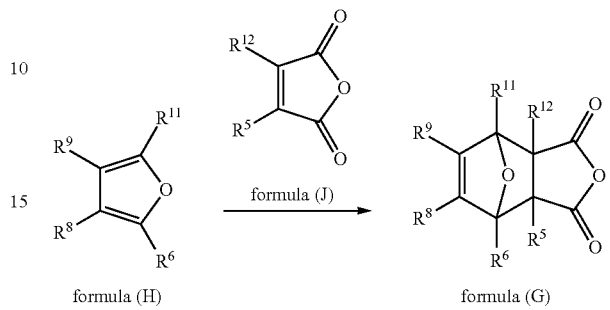

formula (H) + formula (J) → formula (G)

Compounds of formula (H) and formula (J) are known compounds, or may be made from known compounds by known methods.

Compounds of formula (G) are alkenes, and as such undergo further reactions typical of alkenes to give additional compounds of formula (F) according to known procedures. Examples of such reactions include, but are not restricted to, halogenation, epoxidation, cyclopropanation, dihydroxylation, hydroarylation, hydrovinylation and hydration of alkenes. Compounds of formula (G) wherein $R^8$ or $R^9$ are bromine or iodine are vinyl halides, and undergo known reactions of vinyl halides such as Suzuki-Miyaura, Sonogashira, Stille and related reactions. Compounds of formula (G) wherein $R^8$ or $R^9$ are $C_1$-$C_6$alkoxy are enol ethers, and these may be hydrolysed to the corresponding ketone using standard procedures to give additional compounds of formula (F). In turn, these products may be transformed into additional compounds of formula (F) by methods described, for example by J. March, Advanced Organic Chemistry, third edition, John Wiley and Sons.

In a further approach, a compound of formula (G) may be prepared by reacting a compound of formula (H) with a compound of formula (K), wherein R" is hydrogen or an alkyl group, to give a compound of formula (L) and cyclising a compound of formula (L) under known conditions (see, for example, P. Sprague et al., J. Med. Chem., (1985), 28, 1580; A. Guzaev and M. Manoharan, J. Am. Chem. Soc., (2003), 125, 2380, and A. Marchand and R. Allen, J. Org. Chem., (1975), 40 (17), 2551.

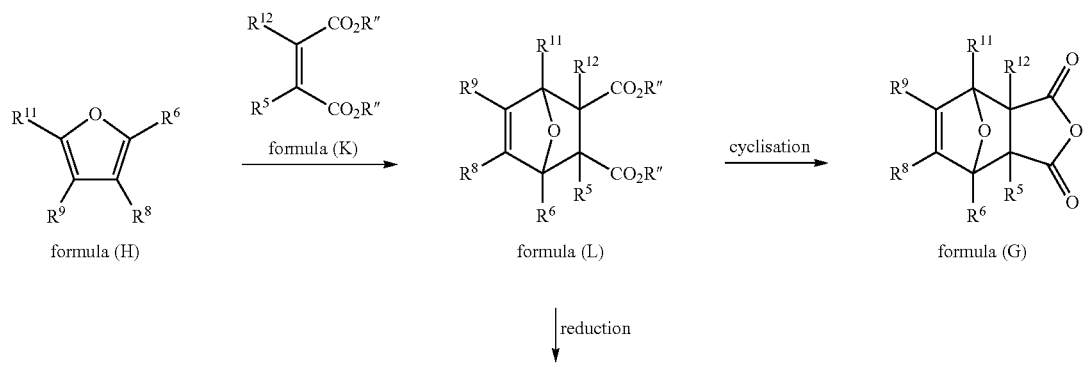

formula (H) + formula (K) → formula (L) → (cyclisation) → formula (G)

↓ reduction

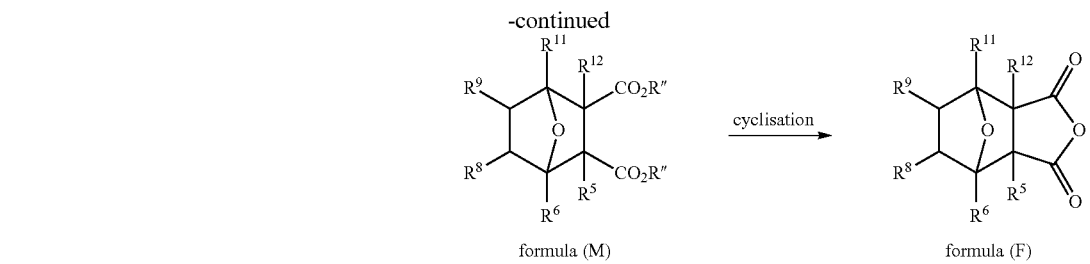

formula (M) → cyclisation → formula (F)

wherein R⁷ and R¹⁰ = H

A compound of formula (L) may also be reduced to a compound of formula (M), and a compound of formula (M) cyclised to a compound of formula (F) wherein $R^7$ and $R^{10}$ are hydrogen, under conditions similar to those described previously.

Compounds of formula (K) are known compounds, or may be prepared from known compounds by known methods.

Additional compounds of formula (A) may be prepared by reacting an iodonium ylide of formula (N), wherein Ar is an optionally substituted phenyl group, with an aryl boronic acid of formula (O), in the presence of a suitable palladium catalyst, a base and in a suitable solvent.

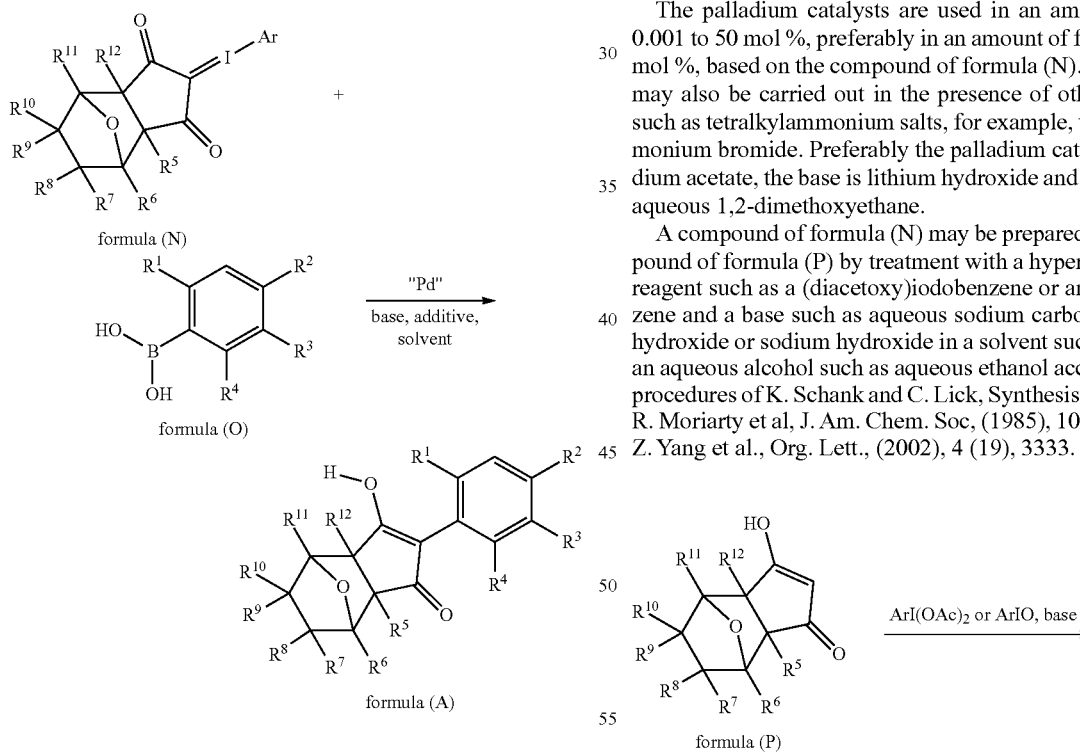

formula (N) + formula (O) →("Pd", base, additive, solvent)→ formula (A)

Suitable palladium catalysts are generally palladium(II) or palladium(0) complexes, for example palladium(II) dihalides, palladium(II) acetate, palladium(II) sulfate, bis(triphenylphosphine)-palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenyl-phosphine ($PPh_3$), tricyclopentylphosphine, tricyclohexylphosphine, 2-dicyclohexylphosphino-2',6'-dimethoxybiphenyl or 2-dicyclohexylphosphino-2',4',6'-triisopropylbiphenyl and the selected solvent, with a compound of formula (N), the arylboronic acid of formula (O), and a base. Also suitable are bidendate ligands, for example 1,1'-bis(diphenylphosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula (N). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of formula (N) may be prepared from a compound of formula (P) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis, (1983), 392; R. Moriarty et al, J. Am. Chem. Soc, (1985), 107, 1375, or of Z. Yang et al., Org. Lett., (2002), 4 (19), 3333.

formula (P) →(ArI(OAc)₂ or ArIO, base)→

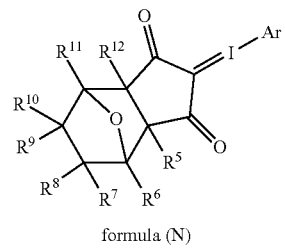

formula (N)

A compound of formula (P) may be prepared from a compound of formula (Q) by known reactions. Examples of such reactions include, but are not restricted to, hydrogenation, halogenation, epoxidation, cyclopropanation, dihydroxylation, hydroarylation, hydrovinylation and hydration of alkenes. In turn, these products may be transformed into additional compounds of formula (P) by methods described, for example by J. March, Advanced Organic Chemistry, third edition, John Wiley and Sons. For example, a compound of formula (P) wherein $R^7$ and $R^{10}$ are hydrogen may be prepared by reduction of a compound of formula (Q) under known conditions. Preferably the reduction is carried out by hydrogenation in the presence of a suitable catalyst such as a platinum, palladium or nickel catalyst, and in a suitable solvent such as ethyl acetate, methanol, ethanol, tetrahydrofuran or acetic acid.

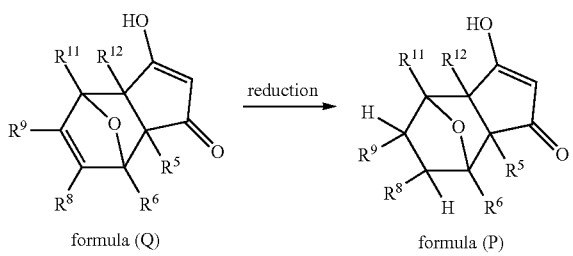

wherein $R^7$ and $R^{10}$ = H

Compounds of formula (Q) wherein $R^8$ or $R^9$ are bromine or iodine are vinyl halides, and undergo known reactions of vinyl halides such as Suzuki-Miyaura, Sonogashira, Stille and related reactions. Compounds of formula (Q) wherein $R^8$ or $R^9$ is $C_1$-$C_6$alkoxy are enol ethers, and these may be hydrolysed to the corresponding ketone using standard procedures. In turn, the ketone may be further transformed, for example by ketalisation, oximation, reduction and the like under known conditions to give additional compounds of formula (P).

A compound of formula (Q) may be prepared by reacting a compound of formula (H) with a cyclopentenedione of formula (R), optionally in the presence of a Lewis acid catalyst, according to procedures described, for example by B. Zwanenburg et al., Tetrahedron (1989) 45 (22), 7109 and by M. Oda et al., Chem. Lett., (1977), 307.

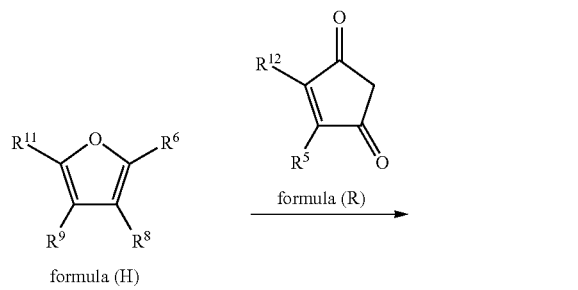

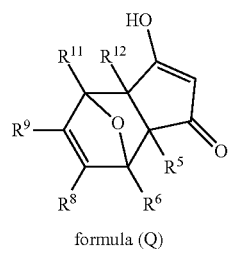

Compounds of formula (R) are known compounds or may be made from known compounds by known methods.

A compound of formula (P) may also be converted into a compound of formula (A) via a compound of formula (S). Thus, a compound of formula (S) may be converted into a compound of formula (A), wherein G is $C_{1-4}$ alkyl, by coupling with an arylboronic acid of formula (O) in the presence of a suitable palladium catalyst and a base and preferably in the presence of a suitable ligand, and in a suitable solvent. Preferably the palladium catalyst is palladium acetate, the base is potassium phosphate, the ligand is 2-dicyclohexylphosphino-2',6'-dimethoxybiphenyl and the solvent is toluene. A compound of formula (A), wherein G is H, may be prepared from a compound of formula (A), wherein G is $C_{1-4}$ alkyl, by hydrolysis, preferably in the presence of an acid catalyst such as hydrochloric acid and optionally in the presence of a suitable solvent such as tetrahydrofuran, acetone or 4-methylpentan-2-one.

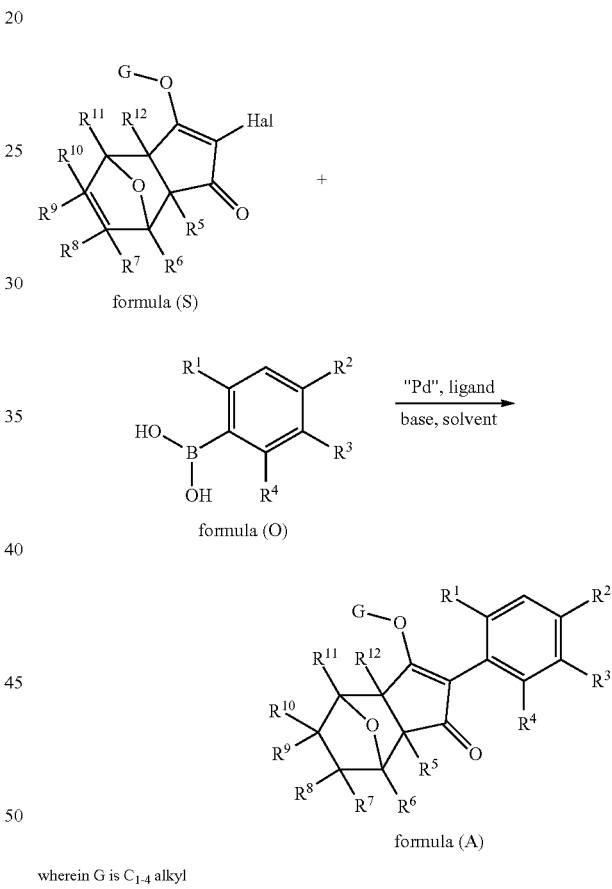

wherein G is $C_{1-4}$ alkyl

A compound of formula (S), wherein G is $C_{1-4}$ alkyl, may be prepared by halogenating a compound of formula (P), followed by reaction of the resulting halide of formula (T) with a $C_{1-4}$ alkyl halide or tri-$C_{1-4}$-alkylorthoformate under known conditions, for example by the procedures of R. Shepherd and A. White (J. Chem. Soc. Perkin Trans. 1 (1987), 2153) and Y.-L. Lin et al.

(Bioorg. Med. Chem. 10 (2002) 685). Alternatively, a compound of formula (S) may be prepared by reacting a compound of formula (P) with a $C_{1-4}$ alkyl halide or a tri-$C_{1-4}$-alkylorthoformate, and halogenating the resulting enone of formula (U) under known conditions.

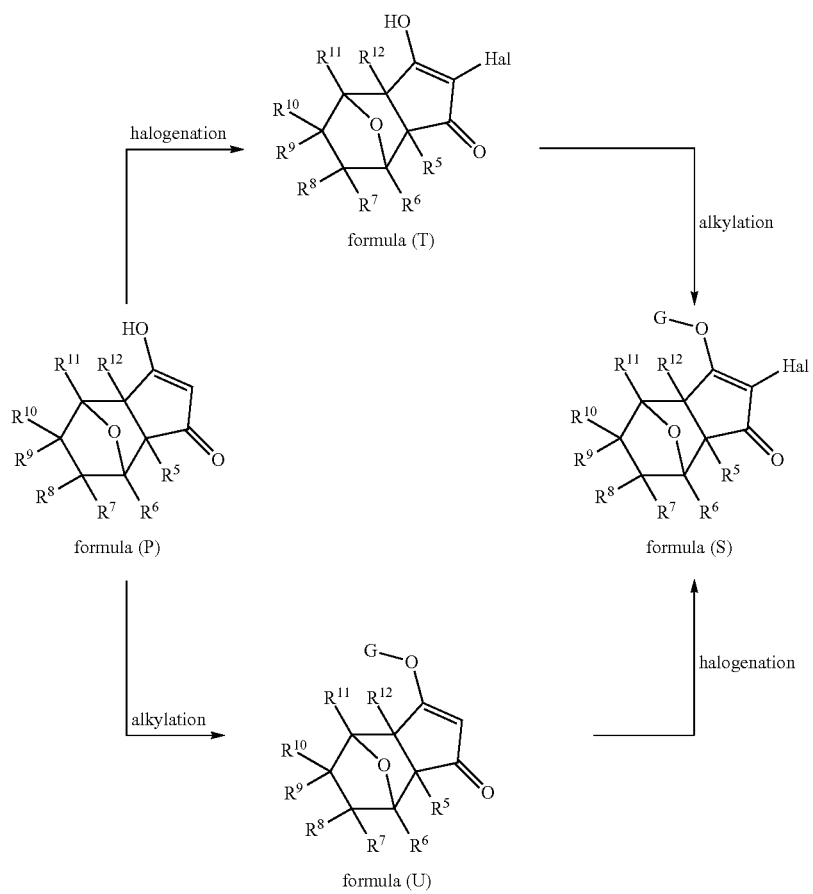

A compound of formula (O) may be prepared from an aryl halide of formula (V), wherein Hal is bromine or iodine, by known methods (see, for example, W. Thompson and J. Gaudino, J. Org. Chem., (1984), 49, 5237 and R. Hawkins et al., J. Am. Chem. Soc., (1960), 82, 3053). For example, an aryl halide of formula (V) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkylborate (preferably trimethylborate or triisopropylborate) to give an aryl dialkylboronate which may be hydrolysed to provide a boronic acid of formula (O) under acidic conditions.

Alternatively a compound of formula (V) may be reacted with bis(pinacolato)diboron or pinacolborane under known conditions (see, for example, N. Miyaura at al., J. Org. Chem., (1995), 60, 7508, and W. Zhu and D. Ma, Org. Lett., (2006), 8 (2), 261), and in turn the resulting products may be hydrolysed under acidic conditions to give a boronic acid of formula (O).

An aryl halide of formula (V) may be prepared from an aniline of formula (W) by known methods, for example the Sandmeyer reaction, via the corresponding diazonium salts.

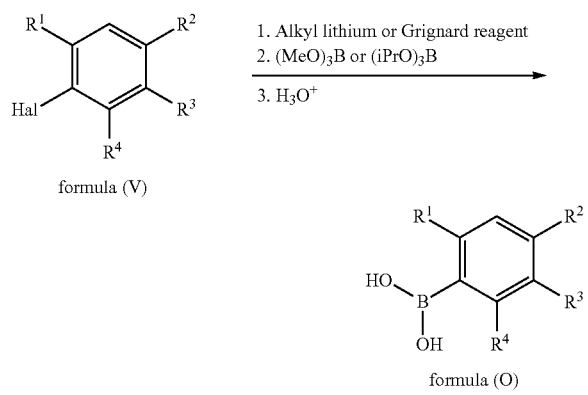

An aniline of formula (W) may be made by the cross-coupling of an aryl halide of formula (X), wherein Hal is chlorine, bromine or iodine or a pseudohalide such as a trifluoromethanesulfonyl moiety, with a suitable coupling partners such as an aryl- or heteroarylboronic acid, $R^3$—$B(OH)_2$, an aryl- or heteroarylboronate ester, $R^3$—$B(OR'''')_2$, wherein $R^3$—$B(OR'''')_2$ represents a cyclic boronate ester derived from a 1,2- or a 1,3-alkane diol such as pinacol, 2,2-dimethyl-1,3-propanediol and 2-methyl-2,4-pentanediol, or a metal (especially potassium) aryl-, or heteroaryltrifluoroborate salt, $M^+[R^3$—$BF_3]^-$ in the presence of a suitable palladium catalyst, a suitable ligand and a suitable base in the presence of a suitable solvent, under Suzuki-Miyaura conditions (see, for example, J.-H. Li, Q.-M. Zhu and Y.-X. Xie, Tetrahedron, (2006), 62, 10888; K. Anderson and S. Buchwald, Angew. Chem. Int. Ed. (2005), 44, 6173; M. Lysen and K. Mohler, Synthesis, (2006), 4, 692; N. Kudo, M. Perseghini and G. Fu, Angew. Chem. Int. Ed., (2006), 45, 1282; J. Yan, W. Hu and W. Zhou, Synth. Commun. (2006), 36, 2102; R. Arvela and N. Leadbeater, Org. Lett., (2005), 7 (11) 2101; T. Barder and S. Buchwald, Org. Lett., (2004), 6 (16), 2649; F. Bellina, A. Carpita and R. Rossi, Synthesis (2004), 15, 2419 and A. Suzuki, Journal of Organometallic Chemistry, (2002), 653, 83).

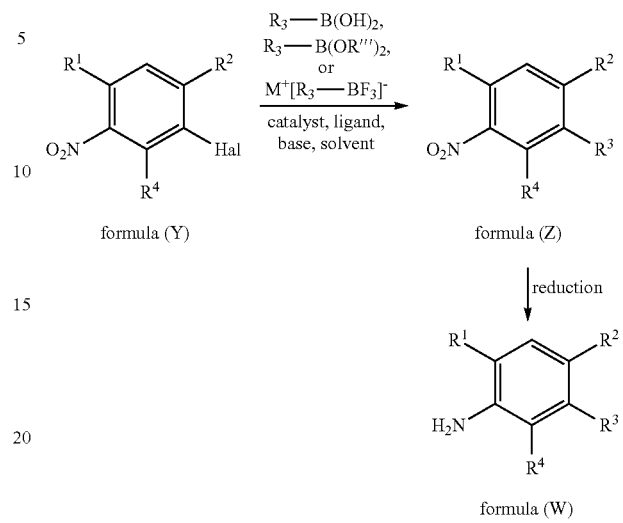

By similar methods, a compound of formula (W) may also be prepared from a compound of formula (AA) via a compound of formula (BB) or a compound of formula (CC).

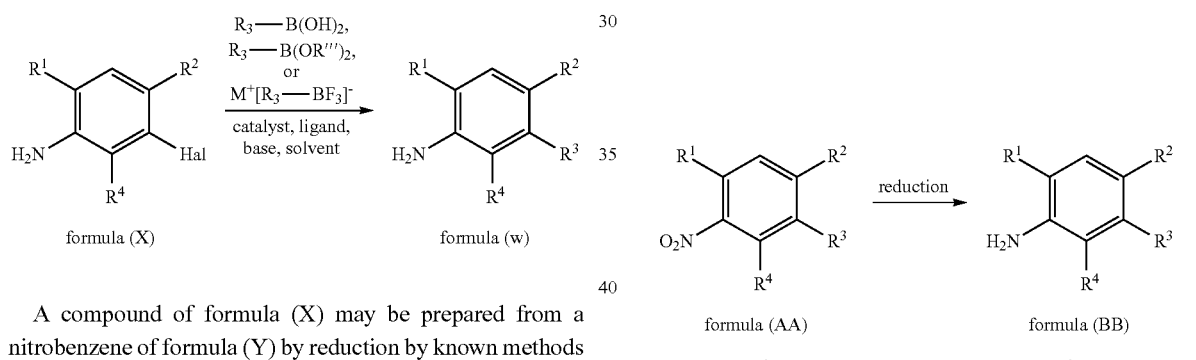

A compound of formula (X) may be prepared from a nitrobenzene of formula (Y) by reduction by known methods (for example by treatment with a reducing agent such as iron or zinc in the presence of an acid, or by catalytic hydrogenation).

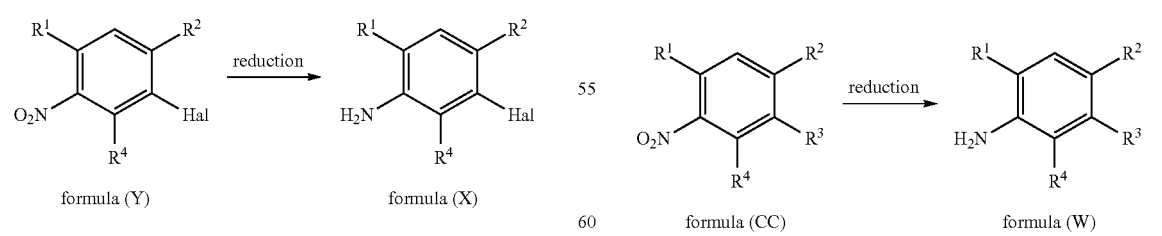

Alternatively, a compound of formula (Y) may be cross-coupled with a suitable aryl- or heteroaryl boronic acid, ester or salt under Suzuki-Miyaura conditions, and the resulting nitrobenzene of formula (Z) reduced under known conditions to give a compound of formula (W).

A compound of formula (BB) may be prepared by reduction of a nitrobenzene of formula (AA), or by halogenating an aniline of formula (DD), or by halogenating an anilide such as an acetanilide of formula (EE) and hydrolysing the resulting amide under known conditions.

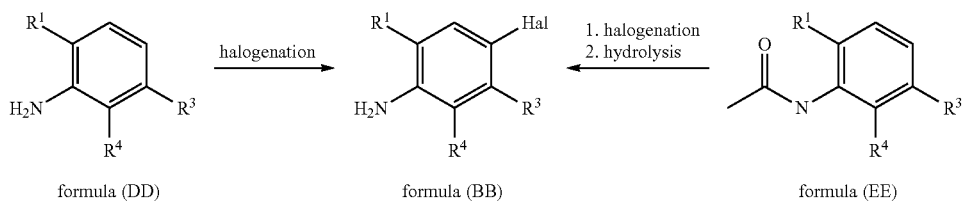

Nitrobenzenes of formula (AA), anilines of formula (DD) and acetanilides of formula (EE) are known compounds or may be prepared by known methods.

In a further approach, a compound of formula (A) may be prepared by reaction of a compound of formula (P) with an aryl lead tricarboxylate, preferably an aryl lead triacetate of formula (FF) in the presence of a suitable ligand (for example N,N-dimethylaminopyridine, pyridine, imidazole, bipyridine, and 1,10-phenanthroline, preferably one to ten equivalents of N,N-dimethylaminopyridine with respect to compound (P)) in a suitable solvent (for example chloroform, dichloromethane and toluene, preferably chloroform and optionally in the presence of a co-solvent such as toluene) at 25° C. to 100° C. (preferably 60-90° C.) and optionally in the presence of a suitable catalyst such as a mercury (II) salt such as mercury (II) acetate. Similar reactions are described in the literature (for example see, J. Pinhey, B. Rowe, Aust. J. Chem., (1979), 32, 1561; J. Morgan, J. Pinhey, J. Chem. Soc. Perkin Trans. 1; (1990), 3, 715).

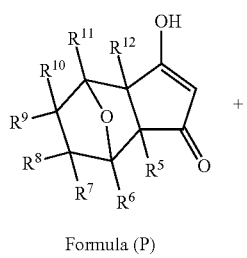

Formula (P)

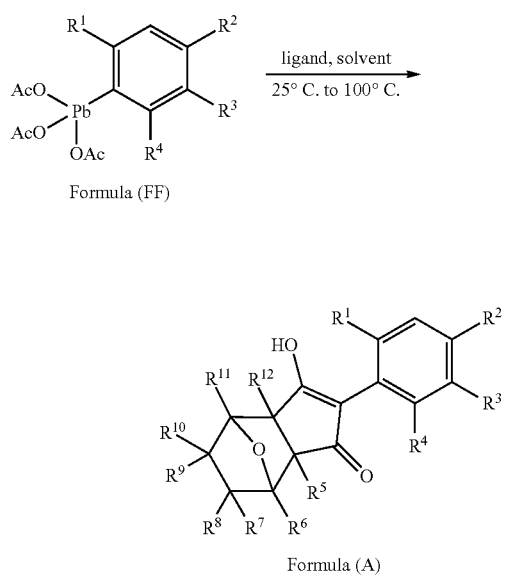

The organolead reagent of formula (FF) may be prepared from a boronic acid of formula (O) a stannane of formula (GG), or by direct plumbation of a compound of formula (HH) with lead tetraacetate according to known procedures.

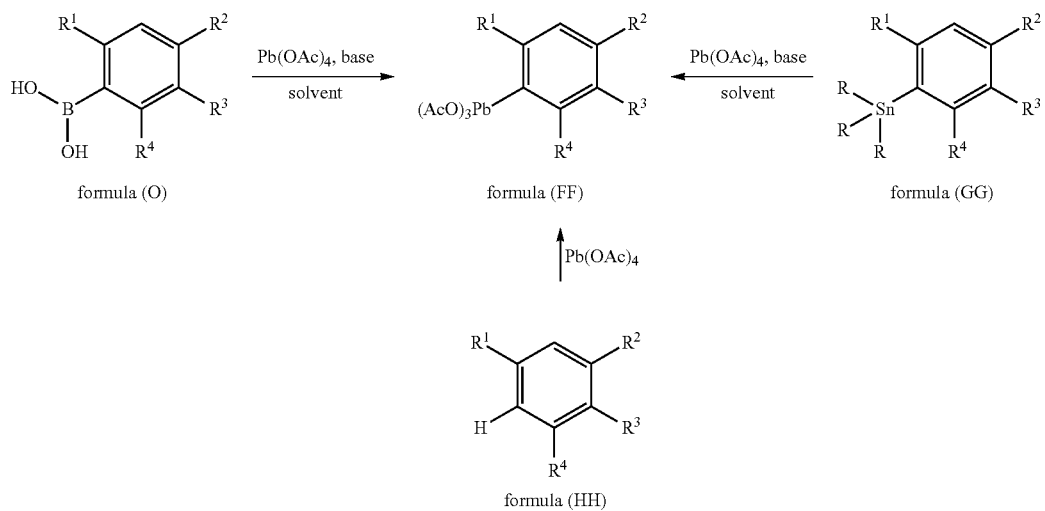

In another approach, a compound of formula (A) may be prepared by reacting a compound of formula (P) with a suitable triarylbismuth (V) reagent (such as a triarylbismuth diacetate of formula (JJ) or a triarylbismuth dichloride) under conditions described, for example, by J-P Finet and A. Yu. Fedorov, J. Organometallic Chemistry, (2006), 691, 2386; A. Yu. Fedorov et al., Russ. Chem. Bull. Int. Ed., (2005), 54 (11), 2602, and by P. K. Koech and M. J. Krische, J. Am. Chem. Soc., (2004), 126 (17), 5350 and references therein.

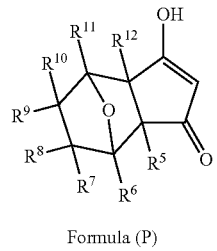

Formula (P)

+

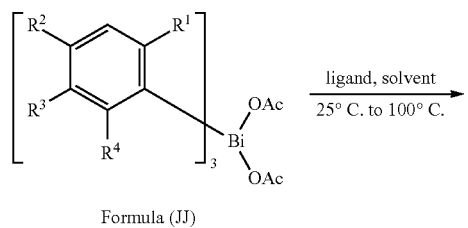

Formula (JJ)

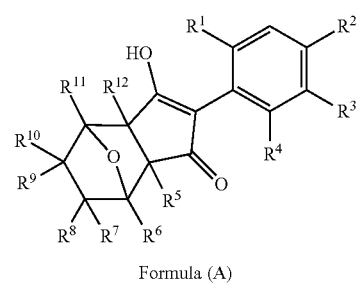

Formula (A)

In a further approach, additional compounds of formula (I), wherein $R^7$ and $R^{10}$ form a bond, may be prepared by hydrolysing compounds of formula (I), wherein G is $C_1$-$C_6$ alkyl and $R^7$ and $R^{10}$ form a bond, under aqueous acidic conditions.

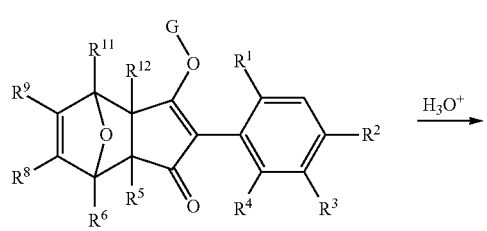

formula (I) wherein G is $C_1$-$C_6$alkyl
and $R^7$ and $R^{10}$ form a bond

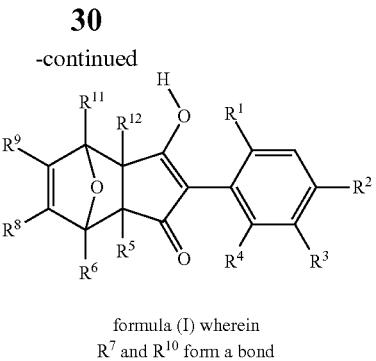

formula (I) wherein
$R^7$ and $R^{10}$ form a bond

A compound of formula (I), wherein G is $C_1$-$C_6$alkyl and $R^7$ and $R^{10}$ form a bond, may be prepared by reacting a compound of formula (KK), wherein G is $C_1$-$C_6$alkyl, X is halogen or other suitable leaving group (such as an alkyl or arylsulfonate, or an arylselenoxide), with a compound of formula (H), optionally in a suitable solvent such as chloroform or toluene, and optionally in the presence of a suitable base such as 1,8-diazabicyclo[5.4.0]undec-7-ene at a suitable temperature (preferably between −80° C. and 30° C.).

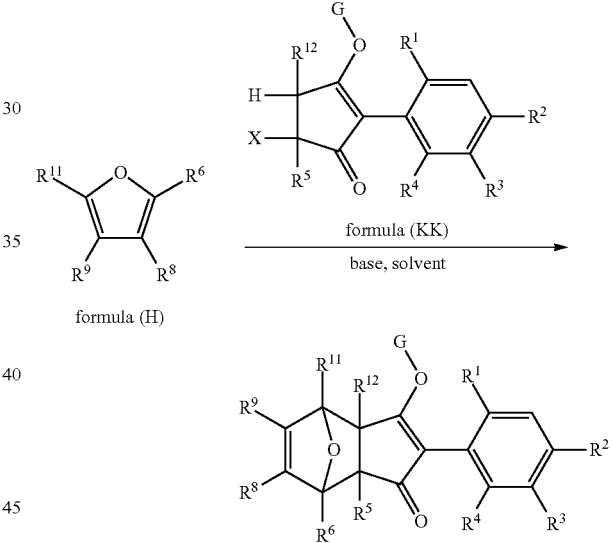

formula (I) wherein G is $C_1$-$C_6$alkyl
and $R^7$ and $R^{10}$ form a bond

A compound of formula (KK), wherein G is $C_1$-$C_6$alkyl and X is halogen may be prepared from a compound of formula (LL), wherein G is $C_1$-$C_6$alkyl, under known conditions.

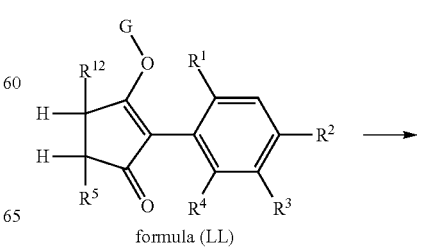

formula (LL)

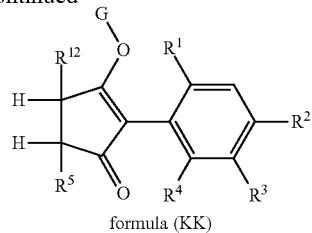

formula (KK)

For example, a compound of formula (KK) wherein X is chlorine may be prepared by reacting a compound of formula (LL) with copper(II) chloride and lithium chloride according to the procedure of E. Kosower et al., J. Org. Chem., (1963), 28, 630.

Compounds of formula (LL) are known compounds or may be made from known compounds by known methods (see, for example, Y. Song, B. Kim and J-N Heo, Tetrahedron Lett., (2005), 46, 5977). Alternatively, a compound of formula (LL) wherein G is $C_1$-$C_6$alkyl may be prepared by alkylation of a compound of formula (LL), wherein G is hydrogen under known conditions.

Compounds of formula (LL), wherein G is hydrogen, are known, or may be prepared from known compounds by known methods (see, for example, T. Wheeler, U.S. Pat. No. 4,338,122; T. Wheeler, U.S. Pat. No. 4,283,348; J. Kuethe et al., J. Org. Chem., (2002), 67, 5993; S. Buchwald et al., J. Am. Chem. Soc., (2003), 125, 11818).

Alternatively, a compound of formula (LL), wherein G is $C_{1-6}$alkyl, may be prepared by reacting a compound of formula (MM), wherein G is $C_{1-6}$alkyl and Z is bromine or iodine with an arylboronic acid of formula (O) in the presence of a suitable metal catalyst, a suitable base, and optionally a suitable ligand, in a suitable solvent.

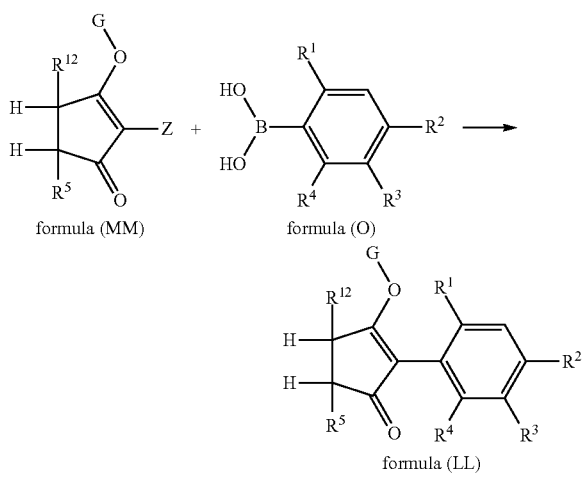

formula (MM)    formula (O)

formula (LL)

Suitable solvents include toluene and n-butanol, suitable bases include inorganic bases such as potassium phosphate, a suitable metal catalyst is palladium, for example in the form of palladium(II) acetate, and suitable ligands include substituted phosphines, for example 2-dicyclohexylphosphino-2', 6'-dimethoxybiphenyl.

Compounds of formula (MM) are known compounds, or may be prepared by methods known in the literature. For example a compound of formula (MM) wherein G is $C_{1-6}$alkyl and Z is a bromine atom may be prepared by reacting a compound of formula (NN), wherein G is $C_{1-6}$alkyl, with a suitable brominating agent, such as N-bromosuccinimide, in a suitable solvent, such as 1,2-dichloroethane, as described by R. Shepherd and A. White (J. Chem. Soc. Perkin Trans. 1 (1987), 10, 2153).

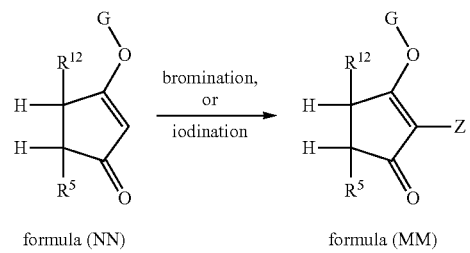

formula (NN)    formula (MM)

Compounds of formula (A) wherein $R^7$ and $R^{10}$ form a bond are alkenes and as such undergo further reactions typical of alkenes to give additional compounds of formula (A) according to known procedures. Examples of such reactions include, but are not restricted to, halogenation, epoxidation, cyclopropanation, dihydroxylation, hydroarylation, hydrovinylation and hydration of alkenes. In turn, these products may be transformed into additional compounds of formula (A) by methods described, for example by J. March, Advanced Organic Chemistry, third edition, John Wiley and Sons. For example, a compound of formula (A) wherein $R^7$ and $R^{10}$ are both hydrogen may be prepared by reduction of a compound of formula (A) wherein $R^7$ and $R^{10}$ form a bond. Preferably the reduction is carried out by hydrogenation in the presence of a suitable catalyst such as a platinum, palladium or nickel catalyst, and in a suitable solvent such as ethyl acetate, methanol, ethanol, tetrahydrofuran or acetic acid.

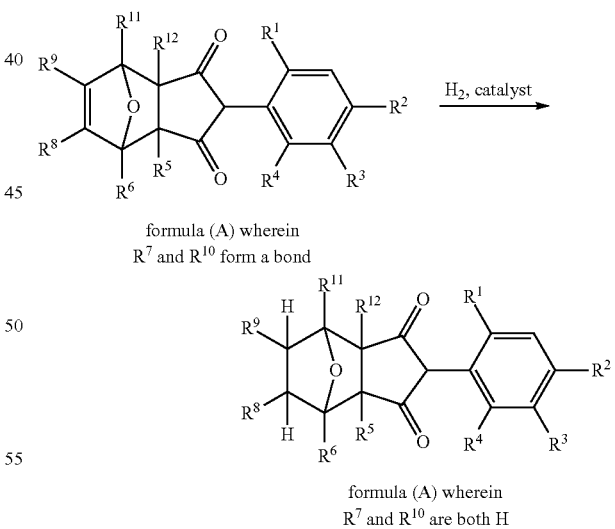

formula (A) wherein
$R^7$ and $R^{10}$ form a bond formula (A) wherein
$R^7$ and $R^{10}$ are both H Compounds of formula (A) wherein $R^8$ or $R^9$ are bromine or iodine are vinyl halides, and undergo known reactions of vinyl halides such as Suzuki-Miyaura, Sonogashira, Stille and related reactions. Compounds of formula (A) wherein $R^7$ and $R^{10}$ form a bond and $R^8$ or $R^9$ is $C_1$-$C_6$alkoxy are enol ethers, and these may be hydrolysed to the corresponding ketone using standard procedures. In turn, the ketone may be further transformed, for example by ketalisation, oximation, reduction and the like under known conditions to give additional compounds of formula (A).

In a further approach, a compound of formula (A) wherein $R^7$ and $R^{10}$ form a bond, may be prepared by the reaction of a compound of formula (OO), with a compound of formula (H), optionally in the presence of a suitable solvent and a suitable catalyst.

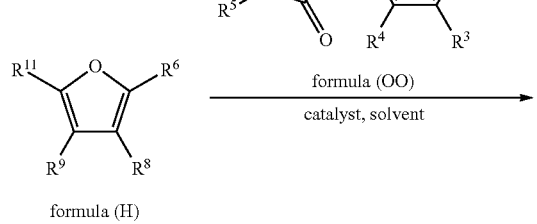

formula (H)

formula (OO)
catalyst, solvent formula (A) wherein
$R^7$ and $R^{10}$ form a bond Preferably the catalyst is a Lewis acid catalyst such as aluminium chloride, bismuth (III) chloride, bismuth (III) trifluoromethanesulfonate, boron trifluoride, cerium (III) chloride, copper (I) trifluoromethanesulfonate, diethylaluminium chloride, hafnium (IV) chloride, iron (III) chloride, lithium perchlorate, lithium trifluoromethanesulfonate, magnesium bromide, magnesium iodide, scandium (III) trifluoromethanesulfonate, tin (IV) chloride, titanium (IV) chloride, titanium (IV) isopropoxide, trimethyl aluminium, N-trimethylsilyl-bis(trifluoromethanesulfonyl)imide, trimethylsilyl trifluoromethanesulfonate, ytterbium (III) trifluoromethanesulfonate, zinc iodide and zirconium (IV) chloride. Magnesium iodide is particularly preferred. Suitable solvents include dichloromethane and chloroform; dichloromethane is particularly preferred.

A compound of formula (OO), may be prepared by oxidising a compound of formula (PP) in a suitable solvent such as toluene, acetone, chloroform, dichloromethane or 1,4-dioxane. A wide range of oxidants are suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1,-tris(acetyloxy)-1,1-dihydro-1,2-benziodoxol-3-(11-1)-one (Dess-Martin periodinane). Suitable procedures for effecting this oxidation are described, for example, by K. Saito and H. Yamchika, U.S. Pat. No. 4,371,711, and by G. Piancatelli et al., Tetrahedron (1978), 34 (18), 2775.

formula (PP)

oxidation formula (OO)

The compounds of formula (OO) are novel and have been specifically designed as intermediates for the synthesis of the compounds of formula (I).

A compound of formula (PP) may be prepared from a compound of formula (QQ) by treatment with a suitable acid catalyst in the presence of water and optionally in the presence of a suitable co-solvent.

formula (QQ)

aqueous acid formula (PP)

For example, a compound of formula (QQ) may be converted to a compound of formula (PP) in the presence of an aqueous solution of an acid such as formic acid, dichloroacetic acid, trichloroacetic acid, phosphoric acid, polyphosphoric acid and pyrophosphoric acid, optionally in the presence of a co-solvent such as acetone, butanone, dioxane or tetrahydrofuran by methods similar to those described, for example, by K. Saito and H. Yamchika, U.S. Pat. No. 4,371,711. Preferably the acid is polyphosphoric acid or phosphoric acid. Alternatively a compound of formula (PP) may be prepared from a compound of formula (QQ) by rearrangement in the presence of a Lewis acid catalyst such as zinc chloride in a suitable solvent such as water, optionally in the presence of a suitable co-solvent such as optionally in the presence of a co-solvent such as acetone, butanone, dioxane or tetrahydrofuran by procedures similar to that described by G. Piancatelli et al., Tetrahedron, (1978), 34 (18), 2775.

A compound of formula (QQ) may be prepared by the reduction of a compound of formula (RR) by known conditions (see, for example R. Silvestri et al., J. Med. Chem., (2005), 48, 4378).

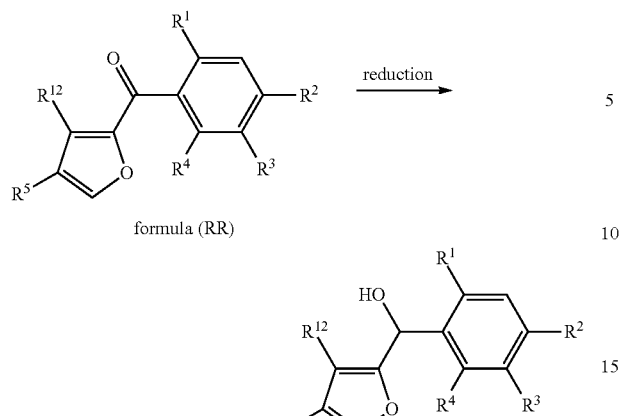

formula (RR) → formula (QQ) (reduction)

Compounds of formula (RR) may be made by acylating a furan of formula (SS) with a suitable carboxylic acid or acid chloride of formula (TT) (wherein Y is OH, or chlorine) or a similar reagent (such as a carboxylic acid anhydride, or a suitable thioester), optionally in the presence of a suitable catalyst (such as a Lewis acid catalyst such as aluminium chloride, aluminium dodecatungstophosphate, bismuth (III) trifluoromethanesulfonate, indium (III) trifluoromethanesulfonate or scandium (III) trifluoromethanesulfonate), and optionally in a suitable solvent (such as dichloromethane, chloroform, acetonitrile, nitromethane and hexane), under known conditions (see, for example, H. Firouzabadi, N. Iranpoor and F Nowrouzi, Tetrahedron, (2004), 60,10843, R. Silvestri et al., J. Med. Chem., (2005), 48 (13), 4378 and references therein).

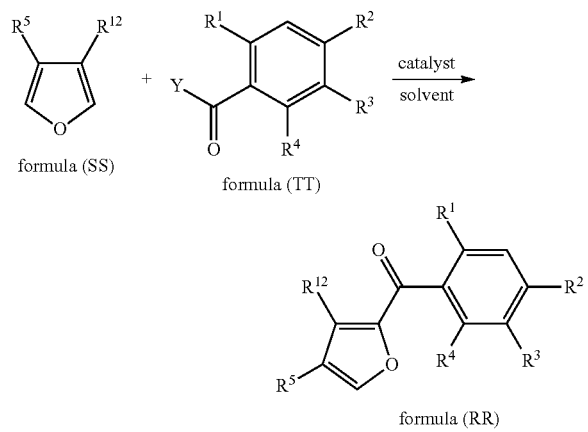

formula (SS) + formula (TT) → formula (RR)

Alternatively a compound of formula (QQ) may be prepared by the addition of a suitable organometallic reagent such as an arylmagnesium halide of formula (UU) wherein Hal is a halide such as chloride, bromide or iodide, or an aryllithium reagent of formula (VV) or diarylzinc reagent of formula (WW) to a furan-2-carboxaldehyde of formula (XX) in a suitable solvent such as diethyl ether or tetrahydrofuran according to known procedures (see, for example G. Panda et al., Tetrahedron Lett., (2005), 46, 3097).

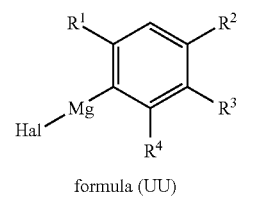

formula (UU)

or

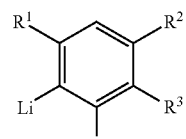

formula (VV)

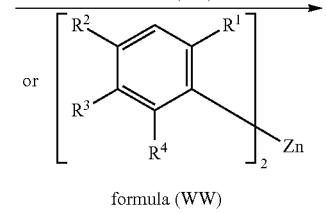

formula (XX)   or   formula (WW)

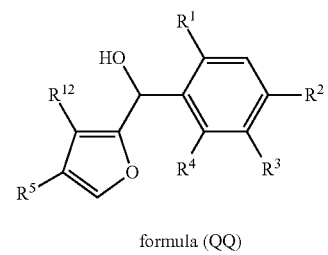

formula (QQ)

Additional compounds of formula (QQ) may be prepared from compounds of formula (YY) by reaction with an alkyl lithium reagent, such as n-butyllithium, optionally in the presence of an additive such as tetramethylethylenediamine, and in a suitable solvent such as diethyl ether or tetrahydrofuran, followed by reaction with a benzaldehyde of formula (ZZ) as described, for example by I. Gupta and M. Ravikanth, J. Org. Chem., (2004), 69, 6796; A. Echavarren et al., J. Am. Chem. Soc., (2003), 125 (19), 5757 and by T. Chandrashekar et al., J. Org. Chem., (2002), 67, 6309.

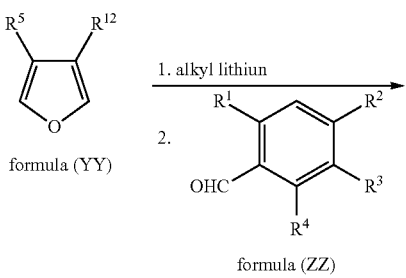

formula (YY)   formula (ZZ)

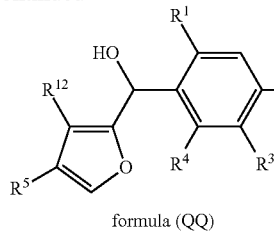

formula (QQ)

Compounds of formula (YY) and formula (ZZ) are known, or may be made by known methods form known compounds. Compounds of formula (ZZ) may be prepared from compounds of formula (V) by known methods. For example, a compound of formula (V) may be treated with an alkyl lithium or alkyl magnesium halide, or with lithium or magnesium, in a suitable solvent, preferably diethyl ether or tetrahydrofuran, at a temperature of between −80° C. and 30° C., and the resulting aryl magnesium or aryl lithium species may be reacted with a suitable formylating reagent such as N,N-dimethylformamide, N-formylmorpholine, N-formylpiperidine, or a trialkyl orthoformate such as triethyl orthoformate according to known procedures (see, for example J. Einhorn and J. Luche, Tetrahedron Lett., (1986); 27 (16) 1793; G. Olah, L. Ohannesian and M. Arvanaghi, J. Org. Chem., (1984), 49 (20), 3856; D. Nelson and E. Uschak, J. Org. Chem., (1977), 42 (20), 3308; C. Dornfeld and G. Colman, Org. Synth. Coll. Vol. 3, (1955), 701; L. Smith and M. Bayliss, J. Org. Chem., (1941), 6, 437). Alternatively, a compound of formula (ZZ) may be prepared by reaction of a compound of formula (V) with carbon monoxide and a suitable hydrogen donor (such as poly(methylhydro-siloxane), hydrogen, formic acid or sodium formate) in the presence of a suitable catalyst (especially a palladium catalyst such as tetrakis(triphenylphosphine)palladium(0), bis(triphenylphosphine)palladium(II) dibromide, bis(triphenylphosphine)palladium(II) dichloride and palladium(II) acetate), according to known methods (see, for example, M-Z. Cai, H. Zhao, J. Zhou and C-S. Song., Synth. Commun., (2002), 32 (6), 923; T. Okano, N. Harada and J. Kiji, Bull. Chem. Soc. Jpn., (1994), 67 (8), 2329; I. Pri-Bar and O. Buchman, J. Org. Chem., (1984), 49 (21), 4009; A. Schoenberg and R. Heck., J. Am. Chem. Soc., (1974), 96 (25), 7761).

In a further approach, a compound of formula (A) may be prepared by cross-coupling an aryl halide of formula (AAA), wherein Hal is chlorine, bromine or iodine, or a pseudohalide such as a trifluoromethanesulfonyl moiety, with a suitable coupling partner such as an aryl- or heteroarylboronic acid, $R^3$—$B(OH)_2$, or a suitable ester, $R^3$—$B(OR'''')_2$, thereof, or a metal (especially potassium) aryl-, or heteroaryltrifluoroborate salt, $M^+[R^3$—$BF_3]^-$ in the presence of a suitable palladium catalyst, a suitable ligand and a suitable base in the presence of a suitable solvent, under Suzuki-Miyaura conditions.

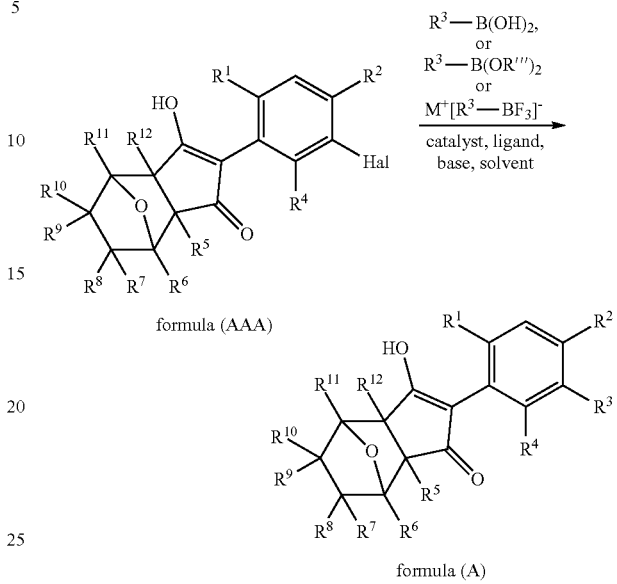

formula (AAA)

formula (A)

Alternatively, a compound of formula (AAA) may be converted into a compound of formula (A), by first converting it into an arylboronic acid, of formula (BBB), or a suitable salt thereof, or into a boronate ester of formula (CCC), followed by cross-coupling with an aryl- or heteroaryl halide, $R^3$—Hal (wherein Hal is chlorine, bromine or iodine or a pseudohalide such as a trifluoromethanesulfonyl moiety) under Suzuki-Miyaura conditions. The conversion of a compound of formula (AAA) to a compound of formula (BBB) may be effected by treatment with at least two equivalents of a suitable metallating agent such as an alkyl lithium or an alkyl magnesium halide in a solvent such as tetrahydrofuran or diethyl ether, or by treatment with at least one equivalent of a suitable base (such as sodium hydride) followed by treatment of the resulting anion with at least one equivalent of a suitable metallating agent in a suitable solvent such as tetrahydrofuran or diethyl ether, and reacting the resulting organometallic species with trimethyl borate, to give an aryl boronate of formula (DDD). An aryl boronate of formula (DDD) may be hydrolysed under acidic conditions to give an arylboronic acid of formula (BBB) for coupling under Suzuki-Miyaura conditions to give a compound of formula (A).

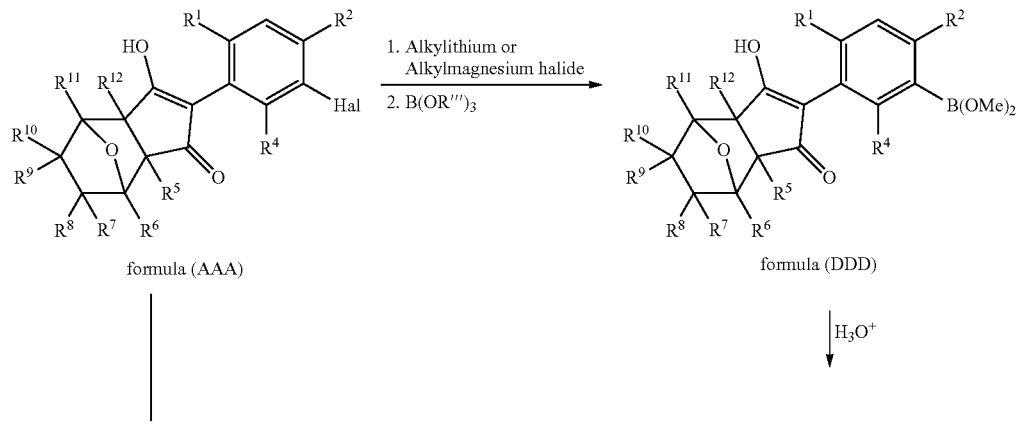

-continued

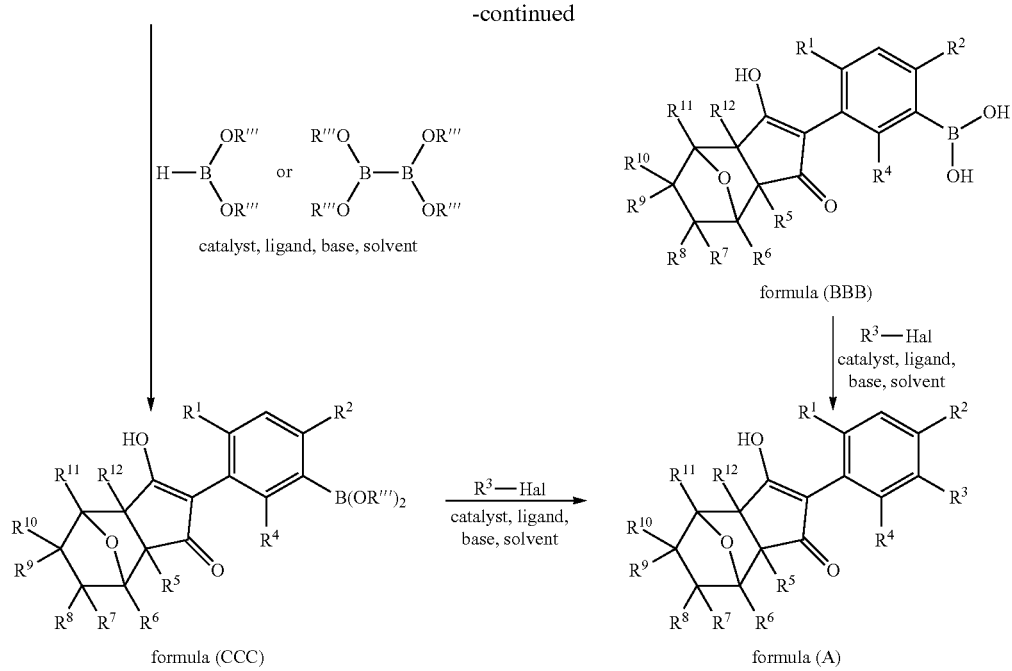

formula (BBB)

formula (CCC)

formula (A)

Similarly, further compounds of formula (A) may be prepared by cross-coupling an aryl halide of formula (EEE), wherein Hal is chlorine, bromine or iodine, or a pseudohalide such as a trifluoromethanesulfonyl moiety, with a suitable coupling partner such as an aryl- or heteroarylboronic acid, $R^2$—$B(OH)_2$, or a suitable ester, $R^2$—$B(OR'''')_2$, thereof, or a metal (especially potassium) aryl-, or heteroaryltrifluoroborate salt, $M^+[R^2$—$BF_3]^-$ in the presence of a suitable palladium catalyst, a suitable ligand and a suitable base in the presence of a suitable solvent, under Suzuki-Miyaura conditions.

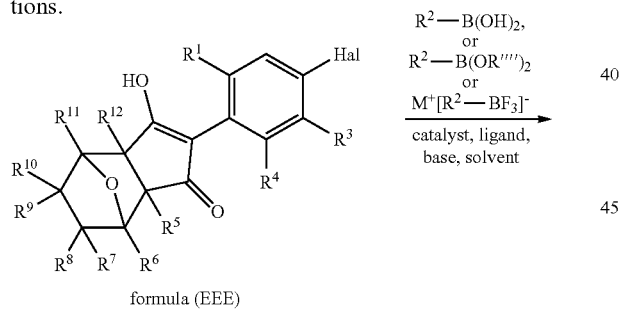

formula (EEE)

-continued

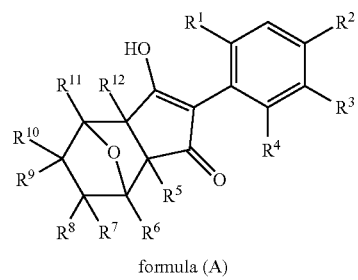

formula (A)

Alternatively, a compound of formula (A) may be prepared from a compound of formula (EEE) via a compound of formula (FFF) or a compound of formula (HHH) using methods similar to those described previously for the synthesis of a compound of formula (A) from a compound of formula (BBB) or a compound of formula (DDD).

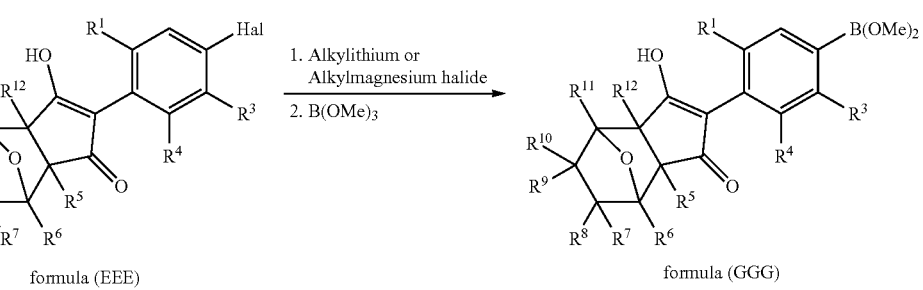

formula (EEE)      formula (GGG)

$\downarrow H_3O^+$

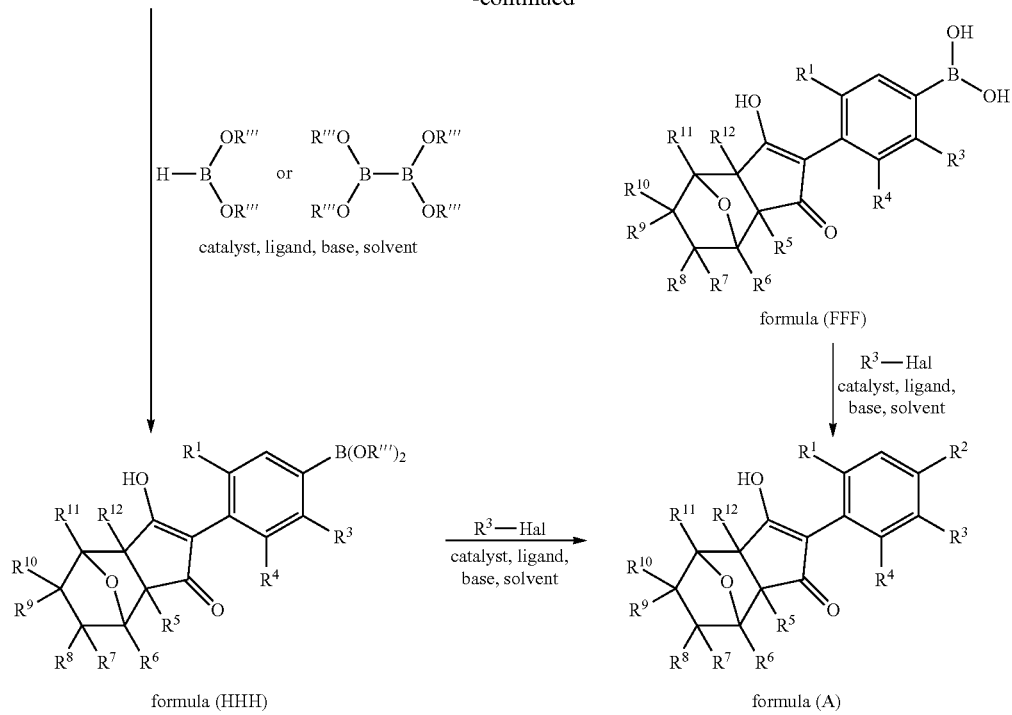
Compounds of formula (AAA) and formula (EEE) may be prepared by similar procedures to those previously described to prepare compounds of formula (A), using appropriate starting materials. For example, a compound of formula (AAA) may be prepared from a compound of formula (JJJ) by procedures analogous to those described previously.
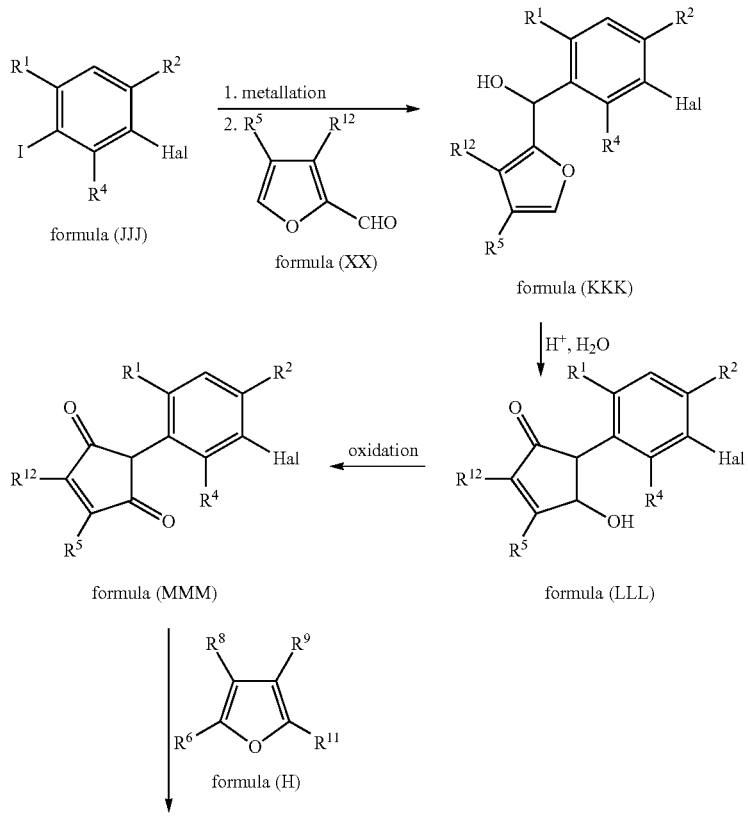

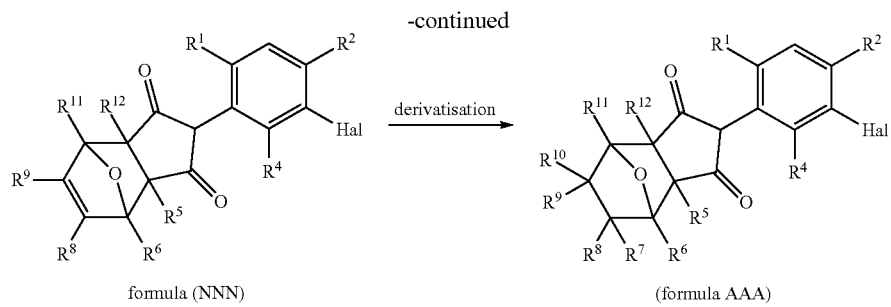

formula (NNN) → (formula AAA)

In a similar way, a compound of formula (EEE) may be prepared from a compound of formula (OOO).

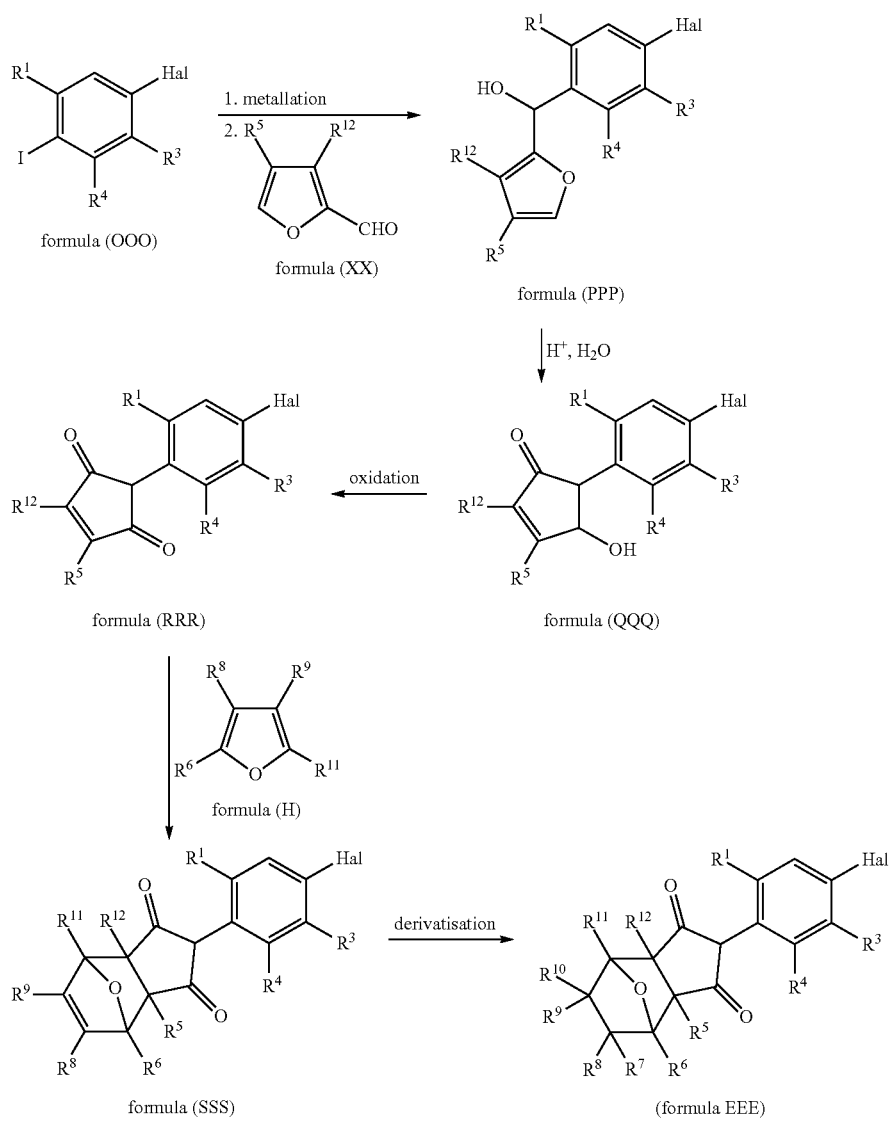

Compounds of formula (JJJ) and of formula (OOO) are known compounds (see, for example, K. Okano et al., J. Am. Chem. Soc., (2006), 128 (48), 15368; M. Gubler et al., WO 2007/137962; E. Priestley et al., WO 2007/076431; M. Lautens et al., J. Org. Chem., (2001), 66, 8127) or may be made by known methods from known compounds.

Additional compounds of formula (AAA) and formula (EEE) may be prepared by reacting a compound of formula (P) with a suitable aryl lead tricarboxylate, under suitable conditions, as described, for example, for the preparation of a compound of formula (A) from a compound of formula (P) and a compound of formula (FF).

hydrolysis of the resulting arylborates to arylboronic acids are also known processes (see, for example, S. Coutts et al., Tetrahedron Lett., (1994), 35 (29), 5109; C. Hutton et al., Tetrahedron Lett., (2004), 45, 6657). An aryl iodide of for-

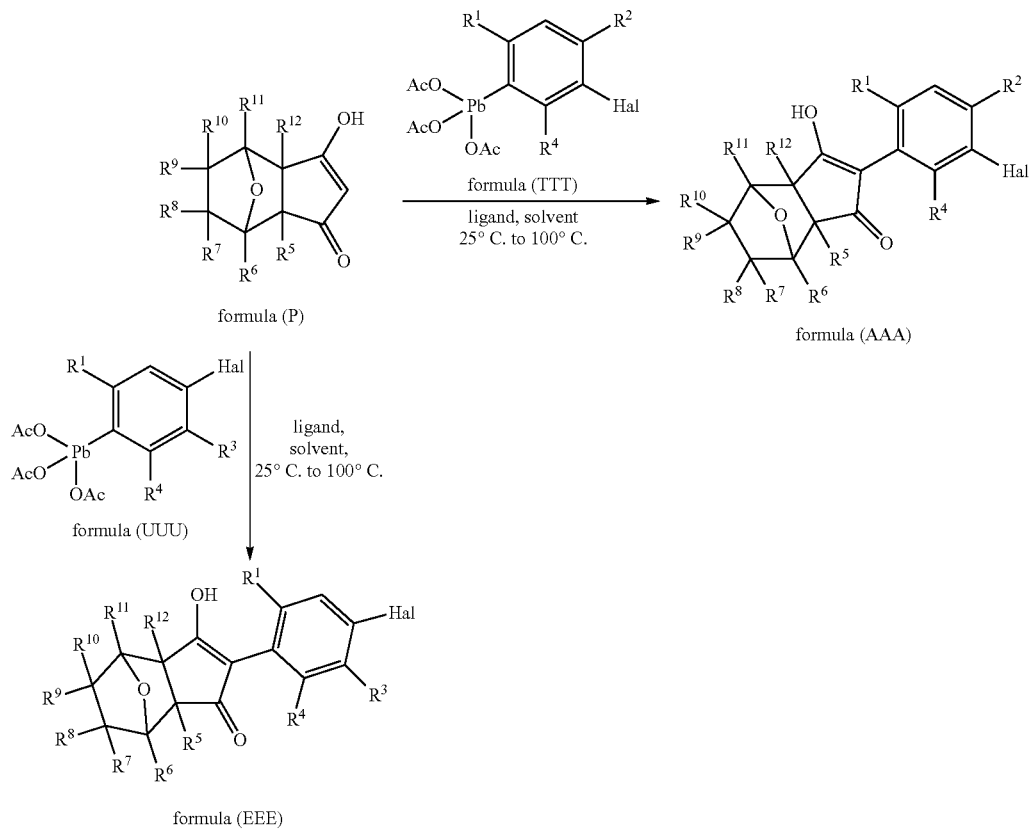

A compound of formula (TTT) may be prepared from an arylboronic acid of formula (VVV) by similar conditions to those used to prepare a compound of formula (FF) from a compound of formula (O).

mula (WWW) may be prepared from an aniline of formula (RR), under Sandmeyer, or related, conditions (see, for example, P. Knochel et al., Synthesis, (2007), No. 1, 81 and references therein).

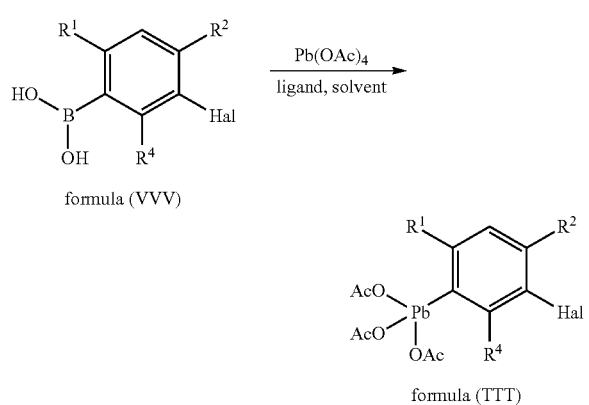

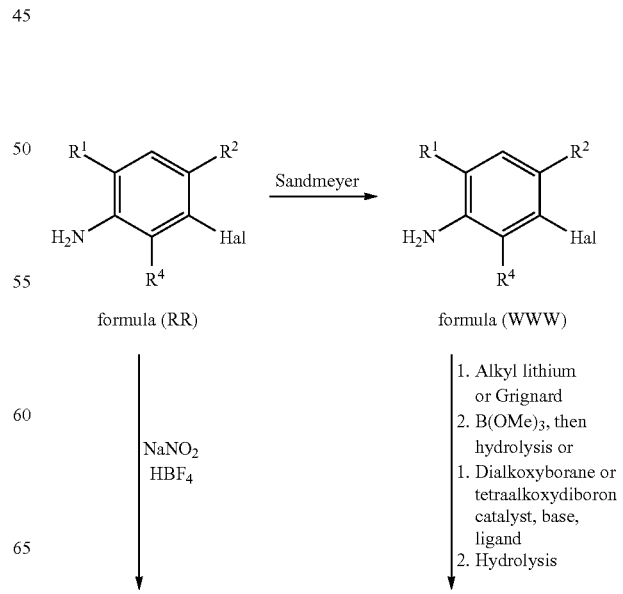

A compound of formula (VVV) may be prepared from an aryl iodide of formula (WWW) by known methods. Boration of aryl iodides may be effected under a variety of known conditions (see, for example W. Zhu and D. Ma, Org. Lett., (2006), 6 (2), 261; M. Murata et al., Synthesis, (2007), No. 3, 351; K-T Wong et al., J. Org. Chem., (2002) 67, 1041),

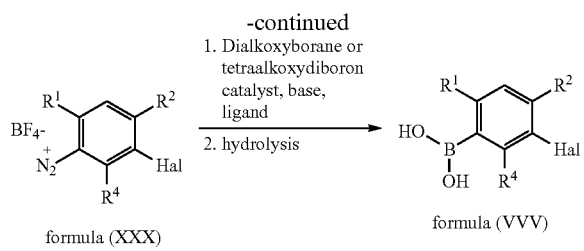

Alternatively a compound of formula (VVV) may be prepared from an aniline of formula (RR) by diazotisation to give an aryldiazonium salt of formula (XXX), followed by boration of the resulting diazonium salt according to procedures described, for example by D. Willis and R. Strongin, (Tetrahedron Lett., (2000), 41, 8683) and hydrolysis of the resulting boronate ester to the boronic acid of formula (VVV) as before.

Similar procedures may be used to prepare a compound of formula (UUU) from an aniline of formula (PP).

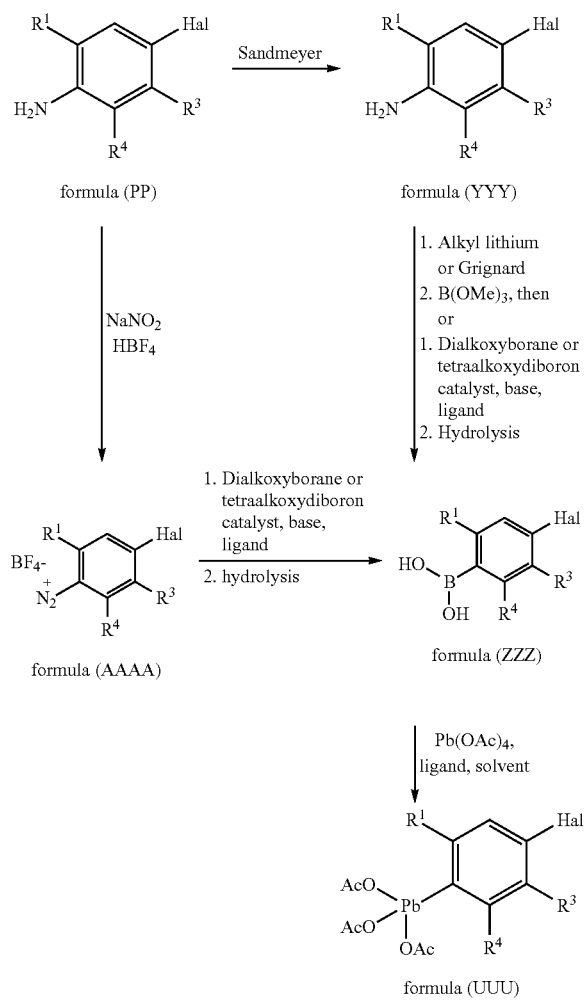

Anilines of formula (PP) and formula (RR) are known compounds, or may be made from known compounds by known methods.

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifiying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). Further oil additives that are preferred according to the invention are SCORE® (Syngenta Crop Protection Canada) and Adigor® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-Trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following compositions:
(%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| F1. Emulsifiable concentrates | | | | |
| --- | --- | --- | --- | --- |
| | a) | b) | c) | d) |
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture ($C_9$-$C_{12}$) | 85% | 78% | 55% | 16% |

Emulsions of any desired concentration can be prepared from such concentrates by dilution with water.

| F2. Solutions | | | | |
| --- | --- | --- | --- | --- |
| | a) | b) | c) | d) |
| active ingredient | 5% | 10% | 50% | 90% |
| 1-methoxy-3-(3-methoxy-propoxy)propane | — | 20% | 20% | — |
| polyethylene glycol MW 400 | 20% | 10% | — | — |
| NMP | — | — | 30% | 10% |
| arom. hydrocarbon mixture ($C_9$-$C_{12}$) | 75% | 60% | — | — |

The solutions are suitable for application in the form of microdrops.

| F3. Wettable powders | | | | |
| --- | --- | --- | --- | --- |
| | a) | b) | c) | d) |
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | | | |
| --- | --- | --- | --- |
| | a) | b) | c) |
| active ingredient | 0.1% | 5% | 15% |
| highly dispersed silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated under reduced pressure.

| F5. Coated granules | | | |
| --- | --- | --- | --- |
| | a) | b) | c) |
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | | | | |
| --- | --- | --- | --- | --- |
| | a) | b) | c) | d) |
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

F7. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F8. Suspension concentrates

|  | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, and for non-selective weed control, which comprises treating the useful plants or the area under cultivation or the locus thereof with a compound of formula I.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important. Preferably, in these mixtures, the compound of the formula I is one of those compounds listed in Tables 1 to 192 below:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIN-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula I+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]bicyclo[3.2.1]oct-3-en-2-one.

The mixing partners for the compound of formula I may also be in the form of esters or salts, as mentioned e.g. in The Pesticide Manual, 12th Edition (BCPC) 2000.

The compounds of formula (I) according to the invention can also be used in combination with safeners. Preferably, in these mixtures, the compound of the formula (I) is one of those compounds listed in Tables 1 to 192 below. The following mixtures with safeners, especially, come into consideration:

compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecoprop and compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula I, optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10000 ppm, preferably from 100 to 1000 ppm.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds are shown in Table T1 as a single enol tautomer, but it should be inferred that this description covers both the diketone form and any possible enols which could arise through tautomerism. Furthermore, some of the compounds in Table T1 and Table P1 are drawn as single enantiomers for the purposes of simplicity, but unless specified as single enantiomers these structures should be construed as representing a mixture of enantiomers. Within the detailed experimental section the diketone tautomer is chosen for naming purposes, even if the predominant tautomer is the enol form.

Where more than one tautomer or other isomer are observed in proton nmr, the data shown are for the mixture of isomers.

Example 1

Preparation of (1RS,2SR,6RS,7SR)-4-(4'-chloro-4-methylbiphen-3-yl)-10-oxatricyclo[5.2.1.0$^{2,6}$]dec-8-ene-3,5-dione

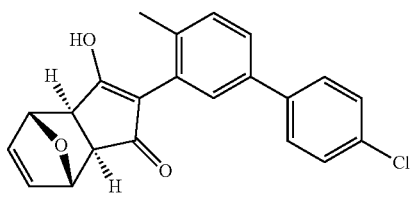 [SMILES: Cc1ccc(-c2ccc(Cl)cc2)cc1C1=C(O)[C@H]2[C@@H](C1=O)[C@@H]1C=C[C@H]2O1]

Step 1: Preparation of 3-amino-4'-chloro-4-methylbiphenyl

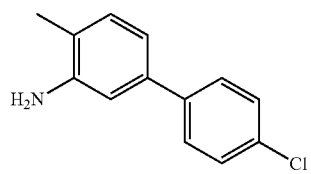

Tetrakis(triphenylphosphine)palladium (0) (3.7 g, 3 mmol) and 4-chlorophenylboronic acid (20.2 g, 0.13 mol) are added to a solution of 5-bromo-2-methylaniline (20 g, 0.1 mol) in 1,2-dimethoxy-ethane (200 ml). After stirring the reaction mixture for 15 minutes at 20° C., a solution of 20% aqueous sodium carbonate (300 ml) is added to the mixture, and the resulting mixture is refluxed for 24 hours. The reaction mixture is cooled to room temperature, diluted with water (600 ml) and extracted using ethyl acetate. The combined organic extracts are dried over anhydrous sodium sulfate, filtered and the filtrate evaporated under reduced pressure. The residue is further purified by column chromatography on silica gel, eluting with 7% ethyl acetate in hexane to give 3-amino-4'-chloro-4-methylbiphenyl.

Step 2: Preparation of 3-bromo-4'-chloro-4-methylbiphenyl

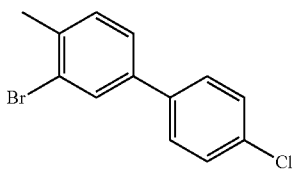

Hydrobromic acid (48% wt. in water, 120 ml) is added dropwise to a suspension of 5-(4-chlorophenyl)-2-methylaniline (21 g, 0.09 mol) in water (80 ml), and the mixture is stirred until the solid is dissolved. The mixture is cooled to −5° C. and a solution of sodium nitrite (10.12 g, 0.14 mol) in water (50 ml) is added dropwise, maintaining the temperature at 0-5° C. The reaction mixture is stirred for 1 hour, then added to a pre-cooled solution of cuprous bromide (17.9 g, 0.12 mol) in hydrobromic acid (48% wt. in water, 120 ml) at 0° C. The reaction mixture is stirred and allowed to warm to room temperature overnight. The mixture is extracted with ethyl acetate, and the organic extracts are combined, dried over anhydrous sodium sulfate, filtered and the filtrate is concentrated under reduced pressure. The residue is further purified by column chromatography on silica gel, eluting with 2% ethyl acetate in hexane to give 3-bromo-4'-chloro-4-methylbiphenyl.

Step 3: Preparation of 4'-chloro-4-methylbiphen-3-ylboronic acid

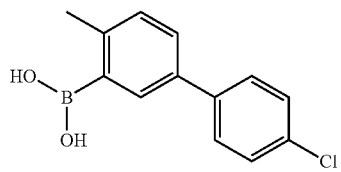 [SMILES: Cc1ccc(-c2ccc(Cl)cc2)cc1B(O)O]

5-(4-chlorophenyl)-2-methyl-1-bromobenzene (5.0 g, 0.02 mol) is dissolved in tetrahydrofuran (125 ml), and the temperature is brought to −78° C. n-Butyllithium (1.33 molar solution in hexanes, 17.3 ml,) is added dropwise over 30 minutes, maintaining the temperature at approximately −78° C. The reaction mixture is stirred for one and a half hours at −78° C., then trimethylborate (2.58 g, 0.024 mol) is added dropwise and the reaction mixture stirred for three and a half hours, allowing it to warm to 0° C. A solution of 2N aqueous hydrochloric acid (50 ml) is then added dropwise, and once the addition is complete the mixture is stirred for 2 hours. The mixture is concentrated under reduced pressure to remove most of the tetrahydrofuran, then diluted with water (~80 ml) and extracted with diethyl ether. The organic extracts are combined, dried over anhydrous sodium sulfate, filtered and the filtrate is evaporated under reduced pressure. The residue is further purified by column chromatography on silica gel, eluting with 7% ethyl acetate in hexane to give 4'-chloro-4-methylbiphen-3-ylboronic acid.

Step 4: Preparation of 4'-chloro-4-methylbiphen-3-yllead triacetate

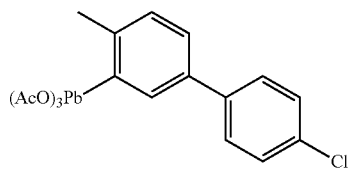

Step 4a

To a mixture of lead tetraacetate (2.44 g, 5.50 mmol) and mercuric diacetate (0.16 g, 0.50 mmol), thoroughly flushed with nitrogen, is added anhydrous chloroform (6 ml). This mixture is warmed to 40° C., and 4'-chloro-4-methylbiphen-3-ylboronic acid (1.23 g, 5.00 mmol) is added in one portion, and the suspension is heated at this temperature for 5 hours. After cooling to room temperature the mixture is concentrated to a small volume, then triturated with hexanes and filtered to yield crude 4'-chloro-4-methylbiphen-3-yllead triacetate.

Step 4b

Crude 4'-chloro-4-methylbiphen-3-yllead triacetate (1.50 g) is dissolved in anhydrous chloroform (20 ml), to which is added powdered anhydrous potassium carbonate (0.59 g, 4.24 mmol) followed by rapid stirring for 5 minutes. Solids are removed by filtration, and the organic solution is concentrated to afford pure 4'-chloro-4-methylbiphen-3-yllead triacetate.

Step 5: Preparation of (1RS,2SR,6RS,7SR)-10-oxatricyclo[5.2.1.0$^{2,6}$]dec-8-ene-3,5-dione

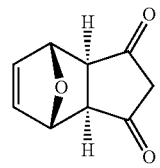 [SMILES: O=C1CC(=O)[C@H]2[C@@H]1[C@@H]1C=C[C@H]2O1]

Furan (13.9 ml, 0.19 mol) is added to cyclopentene-1,4-dione (18.4 g, 0.19 mol) and the reaction mixture is stirred at room temperature for 5 days. The mixture is diluted with methanol and (1RS,2SR,6RS,7SR)-10-oxatricyclo[5.2.1.0$^{2,6}$]dec-8-ene-3,5-dione is collected by filtration, and used without further purification in the next step.

Step 6: Preparation of (1RS,2SR,6RS,7SR)-4-(4'-chloro-4-methylbiphenyl-3-yl)-10-oxatricyclo[5.2.1.0$^{2,6}$]dec-8-ene-3,5-dione

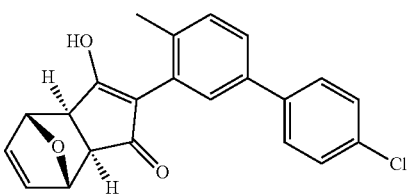 [SMILES: Cc1ccc(-c2ccc(Cl)cc2)cc1C1=C(O)[C@H]2[C@@H](C1=O)[C@@H]1C=C[C@H]2O1]

To a mixture of (1RS,2SR,6RS,7SR)-10-oxatricyclo[5.2.1.0$^{2,6}$]dec-8-ene-3,5-dione (374 mg, 2.3 mmol) and phenanthroline (610 mg, 5 mmol) under an atmosphere of nitrogen is added dry toluene (20 ml) and 4'-chloro-4-methylbiphen-3-yllead triacetate (2.0 g, 3.4 mmol). The reaction mixture is heated at reflux for 3.5 hours, then cooled to room temperature, acidified to pH1 with 2N aqueous hydrochloric acid (20 ml), ethyl acetate (20 ml) added and the mixture is filtered to remove solids. The filtrate is poured into a separating funnel and extracted with ethyl acetate. The organic extracts are combined, dried over anhydrous magnesium sulfate, filtered and the filtrate is evaporated under reduced pressure. The crude product is purified by column chromatography on silica gel to give (1RS,2SR,6RS,7SR)-4-(4'-chloro-4-methylbiphenyl-3-yl)-10-oxatricyclo[5.2.1.0$^{2,6}$]dec-8-ene-3,5-dione.

1H NMR (CDCl$_3$) $\delta_H$ 7.31-7.10 (7H, m), 6.54-6.49 (2H, m), 5.17 (1H, s), 5.13 (1H, s), 3.16 (1H, d), 2.77 (1H, d), 2.26 (3H, s).

Example 2

Preparation of (1RS,2SR,6RS, 7SR)-4-(4'-chloro-4-ethylbiphen-3-yl)-10-oxatricyclo[5.2.1.0$^{2,6}$]dec-8-ene-3.5 dione

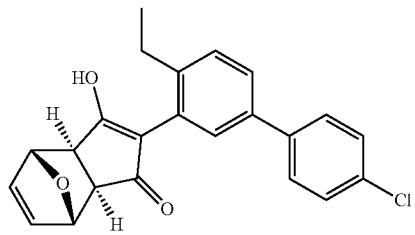 [SMILES: CCc1ccc(-c2ccc(Cl)cc2)cc1C1=C(O)[C@H]2[C@@H](C1=O)[C@@H]1C=C[C@H]2O1]

Step 1: Preparation of 4-ethyl-3-nitroaniline

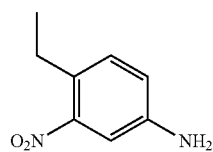

Ammonium nitrate (39.6 g, 0.49 mol) is added portionwise to a chilled (ice-bath) solution of 4-ethylaniline (20 g, 0.16 mol) in concentrated sulfuric acid (100 ml), maintaining the temperature at −10° C. to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and extracted with ethyl acetate. The organic extracts are combined, dried over anhydrous sodium sulfate, filtered and the filtrate is evaporated under reduced pressure to give 4-ethyl-3-nitroaniline.

Step 2: Preparation of 4-bromo-1-ethyl-2-nitrobenzene

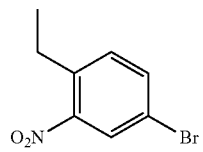

Hydrobromic acid (48% wt. in water, 240 ml) is added dropwise to a suspension of 4-ethyl-3-nitroaniline (20 g, 0.12 mol) in water (80 ml), and the mixture is stirred until the solid dissolves. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate is concentrated under reduced pressure. The residue is further purified by column chromatography on silica gel, eluting with hexane to give 4-bromo-1-ethyl-2-nitrobenzene.

Step 3: Preparation of 4'-chloro-4-ethyl-3-nitrobiphenyl

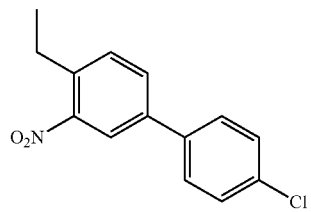 [SMILES: CCc1ccc(-c2ccc(Cl)cc2)cc1[N+](=O)[O-]]

To 4-bromo-1-ethyl-2-nitrobenzene (20.0 g, 87 mmol) in 1,2-dimethoxyethane (150 ml) is added, at room temperature, 4-chlorophenylboronic acid (14.98 g, 96 mmol) and tetrakis-(triphenylphosphine)palladium(0) (2.0 g, 1.74 mmol) and nitrogen gas is bubbled through the mixture. After stirring for 10 minutes at 20° C., a solution of sodium carbonate (73.8 g, 0.696 mol) in water (350 ml) is added and mixture is refluxed for 16 hours. The reaction mixture is cooled to room temperature, filtered through diatomaceous earth, washing with ethyl acetate (200 ml). The mixture is poured into a separating funnel and the two phases are separated. The aqueous phase is extracted with ethyl acetate. The organic extracts are combined, dried over anhydrous magnesium sulfate, filtered and the filtrate is evaporated under reduced pressure to give 4'-chloro-4-ethyl-3-nitrobiphenyl (23.84 g) as a brown oil used without further purification in the next step.

Step 4: Preparation of 3-amino-4'-chloro-4-ethylbiphenyl

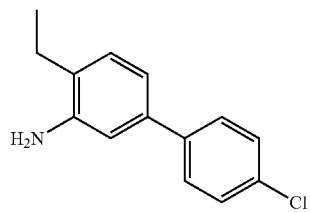

4-(4-chlorophenyl)-1-ethyl-2-nitrobenzene (22.6 g, 86 mmol) is suspended in methanol (250 ml) and the reaction mixture is stirred at room temperature. Water (100 ml) is added, followed by zinc dust (39.0 g, 0.60 mol) and ammonium chloride (13.8 g, 0.26 mol) and the mixture is heated to reflux for 1 hour. The reaction mixture is cooled to room temperature, filtered through diatomaceous earth and the filtrate is evaporated under reduced pressure to remove most of the methanol. The residue is partitioned between ethyl acetate and water and the aqueous phase is re-extracted with ethyl acetate. The organic extracts are combined, washed with water and brine, dried over anhydrous magnesium sulfate, filtered and the filtrate is evaporated under reduced pressure to give 3-amino-4'-chloro-4-ethylbiphenyl (15.0 g) as a colourless solid. The product is used directly without further purification in Step 5.

Step 5: Preparation of 3-bromo-4'-chloro-4-ethylbiphenyl

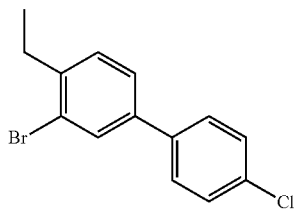 [SMILES: CCc1ccc(-c2ccc(Cl)cc2)cc1Br]

Step 5a

3-Amino-4'-chloro-4-ethylbiphenyl (60.0 g, 0.26 mol) is added portionwise to a mixture of hydrobromic acid (48% wt. in water, 350 ml) and water (250 ml), and once the addition is complete the mixture is heated to 40° C. and stirred for 20 minutes, before being cooled to 5° C. in an ice bath. A solution of sodium nitrite (20.65 g, 0.30 mol) in water (100 ml) is added dropwise over 45 minutes, and once the addition is complete the mixture is stirred at 5° C. for a further 45 minutes.

Step 5b

Meanwhile, hydrobromic acid (48% wt. in water, 400 ml) is heated and stirred at 70° C. and copper sulfate pentahydrate (74.75 g, 0.30 mol) is added in one portion and the mixture is stirred at 70° C. for two minutes to give a dark purple solution, and then copper powder (26.44 g, 0.42 mol) is added in one portion, resulting in a pink suspension.

Step 5c

The mixture containing the diazonium salt (prepared in step 5a) is added portionwise over 70 minutes to the stirred mixture prepared in Step 5b at 70° C. (in between additions the mixture containing the diazonium salt is kept cold in an ice bath). Once the addition is complete the mixture is stirred at 70° C. for a further 30 minutes and then allowed to cool to room temperature, and extracted with ethyl acetate. The organic extracts are combined, washed with water and brine, dried over anhydrous magnesium sulfate, filtered and the filtrate is evaporated under reduced pressure. Purification by column chromatography on silica gel affords 3-bromo-4'-chloro-4-ethylbiphenyl.

Step 6: Preparation of 4'-chloro-4-ethylbiphen-3-ylboronic acid

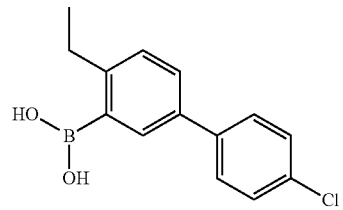 [SMILES: CCc1ccc(-c2ccc(Cl)cc2)cc1B(O)O]

3-Bromo-4'-chloro-4-ethylbiphenyl (10 g, 0.03 mol) is dissolved in tetrahydrofuran (250 ml), and the temperature is brought to −78° C. n-Butyllithium (1.33 molar solution in hexanes, 34.6 ml) is added dropwise over 30 minutes, maintaining the temperature at around −78° C. The reaction mixture is stirred for one and a half hours, then trimethylborate (4.9 g, 0.05 mol) is added dropwise and the reaction mixture is stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate is evaporated under reduced pressure. The residue is further purified by column chromatography on silica gel, eluting with 7% ethyl acetate in hexane to give 4'-chloro-4-ethylbiphen-3-ylboronic acid.

Step 7: Preparation of 4'-chloro-4-ethylbiphen-3-yllead triacetate

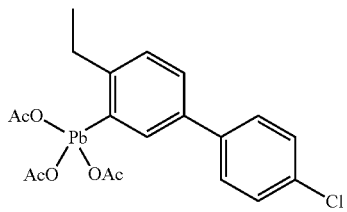

Step 7a

To a mixture of lead tetraacetate (2.15 g, 4.85 mmol) and mercuric diacetate (0.15 g, 0.47 mmol), thoroughly flushed with nitrogen, is added anhydrous chloroform (6 ml). This mixture is warmed to 40° C., and 4'-chloro-4-ethylbiphen-3-ylboronic acid (1.17 g, 4.50 mmol) is added in one portion and the suspension is heated at this temperature for 5 hours. The mixture is then cooled to room temperature, concentrated to a small volume and triturated with hexanes and filtered to yield crude 4'-chloro-4-ethylbiphen-3-yllead triacetate.

Step 7b

Crude 4'-chloro-4-ethylbiphen-3-yllead triacetate (1.50 g) is dissolved in anhydrous chloroform (20 ml), to which is added powdered anhydrous potassium carbonate (0.58 g, 4.16 mmol) followed by rapid stirring for 5 minutes. The solids are removed by filtration, and the organic solution is concentrated to afford pure 4'-chloro-4-ethylbiphen-3-yllead triacetate.

Step 8: Preparation of (1RS,2SR,6RS,7SR)-4-(4'-chloro-4-ethylbiphen-3-yl)-10-oxatricyclo[5.2.1.0$^{2,6}$] dec-8-ene-3,5-dione

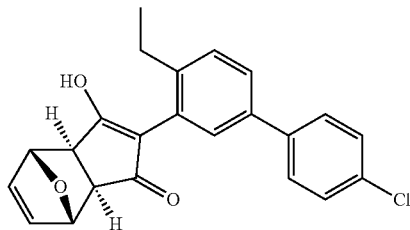 [SMILES: CCc1ccc(-c2ccc(Cl)cc2)cc1C1=C(O)[C@H]2[C@@H](C1=O)[C@@H]1C=C[C@H]2O1]

To a mixture of (1RS,2SR,6RS,7SR)-10-oxatricyclo [5.2.1.0$^{2,6}$]dec-8-ene-3,5-dione (1.7 g, 0.01 mol), 4-dimethylaminopyridine (5.0 g, 0.04 mol) and 4'-chloro-4-ethylbiphen-3-yllead triacetate (9.2 g, 0.015 mol) under an atmosphere of nitrogen is added dry chloroform (50 ml)). The reaction mixture is heated at 40° C. for 5 hours, then cooled to room temperature. The mixture is diluted with ethyl acetate (50 ml), acidified with 2N aqueous hydrochloric acid (50 ml), and the mixture is filtered to remove solids. The filtrate is poured into a separating funnel and extracted with ethyl acetate. The organic extracts are combined, dried over anhydrous magnesium sulfate, filtered and the filtrate is evaporated under reduced pressure. The crude product is purified by column chromatography on silica gel to give (1RS,2SR,6RS, 7SR)-4-(4'-chloro-4-ethylbiphen-3-yl)-10-oxatricyclo [5.2.1.0$^{2,6}$]dec-8-ene-3,5-dione.

1H NMR (CDCl$_3$) δ$_H$ 7.52-7.47 (3H, m), 7.40-7.37 (3H, m), 7.25 (1H, m), 6.51 (2H, s), 5.10 (2H, br. s), 2.81 (2H, br. s), 2.53 (2H, q), 1.15-1.12 (3H, m).

Example 3

Preparation of (1RS,2SR,6RS,7SR)-4-(3.5 dimethyl-biphen-4-yl)-10-oxatricyclo[5.2.1.0$^{2,6}$]decane-3,5-dione

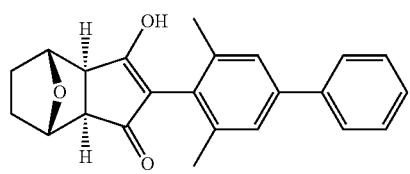 [SMILES: Cc1cc(-c2ccccc2)cc(C)c1C1=C(O)[C@H]2[C@@H](C1=O)[C@@H]1CC[C@H]2O1]

Step 1: Preparation of (1RS,2SR,6RS,7SR)-10-oxatricyclo[5.2.1.0$^{2,6}$]decane-3,5-dione

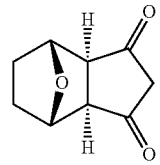 [SMILES: O=C1CC(=O)[C@H]2[C@@H]1[C@@H]1CC[C@H]2O1]

(1RS,2SR,6RS,7SR)-10-oxatricyclo[5.2.1.0$^{2,6}$]dec-8-ene-3,5-dione (2.1 g, 12.8 mmol), prepared in Example 1, Step 5, is dissolved in warm methanol (180 ml) and the mixture is allowed to cool to room temperature. The mixture is then hydrogenated in the presence of 5% palladium on carbon (approx. 50 mg) at 3.5 bar for 4 hours. The catalyst is removed by filtration through diatomaceous earth and the filtrate is concentrated under reduced pressure to afford (1RS, 2SR,6RS,7SR)-10-oxatricyclo[5.2.1.0$^{2,6}$]decane-3,5-dione.

Step 2: Preparation of 3,5-dimethylbiphen-4-ylboronic acid

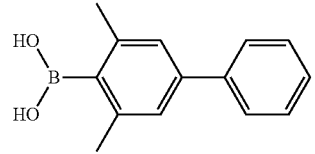 [SMILES: Cc1cc(-c2ccccc2)cc(C)c1B(O)O]

t-Butyllithium (1.7 M solution in hexane, 36.2 ml, 61.6 mmol) is added dropwise to a solution of 3,5-dimethylbiphenyl (7.27 g, 28 mmol) in dry tetrahydrofuran (150 ml) at −78° C. under an atmosphere of nitrogen. The reaction mixture is stirred at −78° C. for 30 minutes, then trimethylborate (9.54 ml, 84 mmol) is added. The resulting mixture is stirred at −78° C. for 30 minutes and then allowed to warm to room temperature. The reaction mixture is acidified with 10% aqueous hydrochloric acid solution and extracted with diethyl ether. The organic layers are combined, dried over anhydrous magnesium sulfate, filtered and the filtrate is evaporated to dryness to give a yellow solid. The crude product is triturated with isohexane and filtered to give 3,5-dimethylbiphen-4-ylboronic acid.

Step 3: Preparation of 3,5-dimethylbiphen-4-yllead triacetate

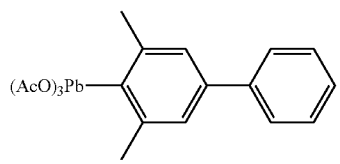

To a solution of lead tetraacetate (4.3 g, 9.7 mmol) in dry chloroform (15 ml) at 40° C. is added 3,5-dimethylbiphen-4-ylboronic acid (2.0 g, 8.8 mmol) in one portion under an atmosphere of nitrogen. The reaction mixture is stirred at 40° C. for 4 hours, and then is cooled to room temperature and filtered, washing the residual solid with chloroform (50 ml). The filtrate is filtered through a plug of potassium carbonate on diatomaceous earth and the filtrate is evaporated to afford 3,5-dimethylbiphen-4-yllead triacetate. The reagent is diluted in chloroform and used as a standard solution.

Step 4: Preparation of (1RS, 2SR,6RS,7SR)-4-(3,5-dimethylbiphen-4-yl)-10-oxa-tricyclo[5.2.1.0²,⁶]decane-3,5-dione

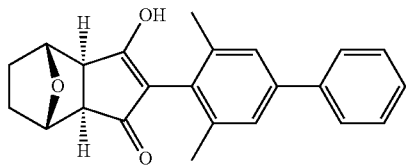

To a mixture of (1RS,2SR,6RS,7SR)-10-oxatricyclo[5.2.1.0²,⁶]decane-3,5-dione (166 mg, 1 mmol) and 4-dimethylaminopyridine (610 mg, 5 mmol) under an atmosphere of nitrogen is added dry chloroform (5.6 ml), and the mixture is stirred at room temperature until all the solids are dissolved. To this solution is then added dry toluene (2 ml), and 3,5-dimethylbiphen-4-yllead triacetate (0.5 M solution in dry chloroform, 2.4 ml, 1.2 mmol). The reaction mixture is heated at reflux for 1 hour, then cooled to room temperature, acidified to pH1 with 2N aqueous hydrochloric acid, filtered and extracted with dichloromethane. The organic extracts are combined, dried over anhydrous magnesium sulfate, filtered and the filtrate evaporated under reduced pressure. The crude product is purified by column chromatography on silica gel to give (1RS,2SR,6RS,7SR)-4-(3,5-dimethylbiphen-4-yl)-10-oxa-tricyclo[5.2.1.0²,⁶]decane-3,5-dione.

¹H NMR (400 MHz, d₄-MeOH) $\delta_H$ 7.60 (2H, d), 7.43 (2H, t), 7.39-7.31 (3H, m), 4.64 (2H, m), 2.90 (2H, s), 2.19 (6H, s), 1.88-1.82 (2H, m), 1.73-1.67 (2H, m).

Example 4

Preparation of (1RS,2SR,6RS,7SR)-4-(2',4'-dichloro-4-ethylbiphen-3-yl)-10-oxa-tricyclo[5.2.1.0²,⁶]decane-3,5-dione

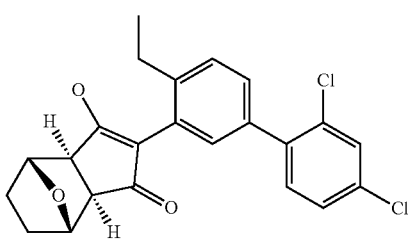 [SMILES: CCc1ccc(-c2ccc(Cl)cc2Cl)cc1C1=C(O)[C@H]2[C@@H](C1=O)[C@@H]1CC[C@H]2O1]

Step 1: Preparation of (5-bromo-2-ethylphenyl)furan-2-ylmethanol

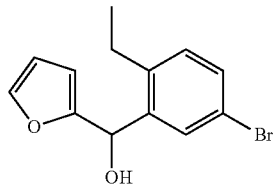 [SMILES: CCc1ccc(Br)cc1C(O)c1ccco1]

4-Bromo-2-iodoethyl benzene (50.0 g, 0.161 mol) is dissolved in anhydrous tetrahydrofuran (250 ml) and cooled to −70° C. under an atmosphere of nitrogen. Isopropylmagnesium chloride (2 M solution in tetrahydrofuran, 100 ml, 0.200 mmol) is added dropwise with vigorous stirring over 40 minutes, maintaining the internal temp below −60° C. by external cooling. When the addition is complete, the reaction is stirred at −70° C. for 20 minutes then allowed to warm to room temperature over 1 hour and 20 minutes. The reaction mixture is then cooled to −70° C. and a solution of 2-furaldehyde (16 ml, 18.6 g, 190 mmol) in tetrahydrofuran (50 ml) is added dropwise over 40 minutes. On completion of the addition, the reaction is allowed to warm to room temperature and stirred at room temperature for 3 hours. Saturated aqueous ammonium chloride solution (~500 ml) is added and the mixture is extracted into ethyl acetate. The organic solutions are combined, washed with brine, dried over anhydrous magnesium sulfate and concentrated under reduced pressure. The residue is further purified by column chromatography on silica gel to give (5-bromo-2-ethylphenyl)furan-2-ylmethanol.

Step 2: Preparation of 5-(5-bromo-2-ethylphenyl)-4-hydroxycyclopent-2-enone

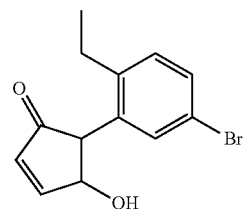 [SMILES: CCc1ccc(Br)cc1C1C(=O)C=CC1O]

A solution of (5-bromo-2-ethylphenyl)furan-2-ylmethanol (40.73 g, 0.145 mol) in acetone (1150 ml) and water (170 ml) is heated to 55° C. and 30 drops of polyphosphoric acid are added. The mixture is stirred at 55° C. for 44 hours, then cooled to room temperature. The reaction mixture is concentrated under reduced pressure to remove most of the acetone then ethyl acetate (500 ml) is added, and the reaction mixture is partitioned. The aqueous phase is extracted into ethyl acetate and the organic solutions are combined, washed with saturated aqueous sodium bicarbonate solution and brine, dried over anhydrous magnesium sulfate, filtered and the filtrate is concentrated under reduced pressure. The residue is purified by column chromatography on silica gel to give 5-(5-bromo-2-ethylphenyl)-4-hydroxycyclopent-2-enone.

Step 3: Preparation of 2-(5-bromo-2-ethylphenyl)cyclopent-4-ene-1,3-dione

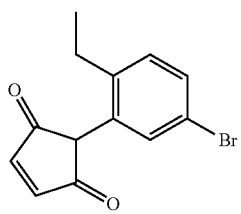 [SMILES: CCc1ccc(Br)cc1C1C(=O)C=CC1=O]

Jones' reagent (75 ml of 1.67 M solution, 125 mmol) is added dropwise over 30 minutes to a cooled (ice-bath) solution of 5-(5-bromo-4-ethylphenyl)-4-hydroxycyclopent-2-enone (33 g, 117 mmol) in acetone (400 ml). The mixture is stirred for 20 minutes, then the cooling bath is removed and the mixture is stirred for 1 hour at room temperature. Isopropanol (150 ml) is added to the yellow slurry and the mixture is stirred at room temperature for 2 hours. The mixture is diluted with ethyl acetate and washed with brine, dried over anhydrous magnesium sulfate, filtered and the filtrate is evaporated under reduced pressure to give 2-(5-bromo-2-ethylphenyl)cyclopent-4-ene-1,3-dione.

Step 4: Preparation of (1RS,2SR,6RS,7SR)-4-(5-bromo-2-ethylphenyl)-10-oxatricyclo-[5.2.1.0$^{2,6}$]dec-8-en-3,5-dione

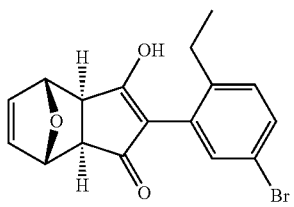 [SMILES: CCc1ccc(Br)cc1C1=C(O)[C@H]2[C@@H](C1=O)[C@@H]1C=C[C@H]2O1]

Furan (4.0 ml, 55.0 mmol) and magnesium iodide (1.00 g, 3.6 mmol) are added to a solution of 2-(5-bromo-2-ethylphenyl)cyclopent-4-ene-1,3-dione (5.0 g, 17.9 mmol) in dichloromethane (20 ml) and the mixture is stirred at room temperature for 3 days. A further quantity of furan (1.3 ml, 17.8 mmol) is added and stirring continued for 18 hours, and then a further quantity of furan (1.3 ml, 17.8 mmol) is added and the mixture is stirred for 48 hours, and then allowed to stand at room temperature for 5 days. The reaction mixture is dissolved in methanol and concentrated under reduced pressure. The residue is purified by column chromatography on silica gel to give (1RS,2SR,6RS,7SR)-4-(5-bromo-2-ethylphenyl)-10-oxatricyclo[5.2.1.0$^{2,6}$]dec-8-en-3,5-dione.

Step 5: Preparation of (1RS,2SR,6RS,7SR)-4-(5-bromo-2-ethylphenyl)-10-oxatricyclo[5.2.1.0$^{2,6}$]decane-3,5-dione

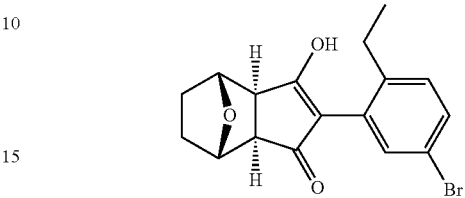

A solution of (1RS,2SR,6RS,7SR)-4-(5-bromo-2-ethylphenyl)-10-oxatricyclo[5.2.1.0$^{2,6}$]dec-8-en-3,5-dione (3.00 g, 8.6 mmol) in methanol (250 ml) is hydrogenated at 3.5 bar over 5% palladium on carbon for 2 hours at room temperature. The catalyst is removed by filtration through diatomaceous earth and the solvent is evaporated under reduced pressure to give (1RS,2SR,6RS,7SR)-4-(5-bromo-2-ethylphenyl)-10-oxatricyclo-[5.2.1.0$^{2,6}$]decane-3,5-dione.

Step 6: Preparation of (1RS,2SR,6RS,7SR)-4-(2',4'-dichloro-4-ethylbiphen-3-yl)-10-oxatricyclo[5.2.1.0$^{2,6}$]decane-3,5-dione

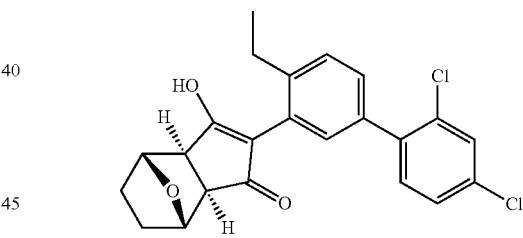

A mixture of (1RS,2SR,6RS,7SR)-4-(5-bromo-2-ethylphenyl)-10-oxatricyclo-[5.2.1.0$^{2,6}$]dec-8-en-3,5-dione (104 mg, 0.3 mmol), 2,4-dichlorophenylboronic acid (114 mg, 0.6 mmol) and cesium fluoride (449 mg, 3.0 mmol) in degassed 1,2-dimethoxyethane (1.5 ml) are stirred under nitrogen at room temperature for 40 minutes. [1,1'-bis(diphenylphosphino)ferrocene]dichloropalladium(II) complex with dichloromethane (39 mg, 0.06 mmol) is added, followed by a further quantity of 1,2-dimethoxyethane (1 ml) and reaction mixture is heated to 80° C. for 16 hours. The mixture is cooled to room temperature, then diluted with dichloromethane and filtered through a small plug of diatomaceous earth. The filtrate is concentrated under reduced pressure and the residue is purified by column chromatography on silica gel to give (1RS,2SR,6RS,7SR)-4-(2',4'-dichloro-4-ethylbiphen-3-yl)-1,7-dimethyl-10-oxatricyclo[5.2.1.0$^{2,6}$]decane-3,5-dione.

$^1$H NMR (400 MHz, d$_4$-MeOH) δ$_H$ 7.52-7.51 (1H, m), 7.35-7.32 (4H, m), 7.03 (1H, s), 4.61-4.60 (2H, m), 2.84 (2H, s), 2.52 (2H, q), 1.82-1.79 (2H, m), 1.67-1.64 (2H, m), 1.12 (3H, t)

Example 5

Preparation of (1RS,2SR,6RS,7SR)-4-(4'-chloro-4-ethyl-2'-fluorobiphen-3-yl)-1,7-dimethyl-10-oxatricyclo[5.2.1.0$^{2,6}$]decane-3,5-dione

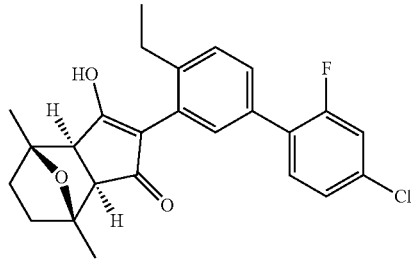 [SMILES: CCc1ccc(-c2ccc(Cl)cc2F)cc1C1=C(O)[C@H]2[C@@H](C1=O)[C@]1(C)CC[C@@]2(C)O1]

Step 1: Preparation of (1RS,2SR,6RS,7SR)-4-(5-bromo-2-ethylphenyl)-1,7-dimethyl-10-oxatricyclo[5.2.1.0$^{2,6}$]dec-8-en-3,5-dione

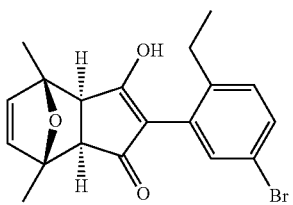 [SMILES: CCc1ccc(Br)cc1C1=C(O)[C@H]2[C@@H](C1=O)[C@]1(C)C=C[C@@]2(C)O1]

2,5-Dimethylfuran (2.3 ml, 21.6 mmol) and magnesium iodide (0.40 g, 1.4 mmol) are added to a solution of 2-(5-bromo-2-ethylphenyl)cyclopent-4-ene-1,3-dione (2.0 g, 7.2 mmol) in dichloromethane (10 ml) and the mixture is stirred at room temperature for 3 days. The reaction mixture is concentrated under reduced pressure and the residue is purified by column chromatography on silica gel to give (1RS,2SR,6RS,7SR)-4-(5-bromo-2-ethylphenyl)-1,7-dimethyl-10-oxatricyclo[5.2.1.0$^{2,6}$]dec-8-en-3,5-dione.

Step 2: Preparation of (1RS,2SR,6RS,7SR)-4-(5-bromo-2-ethylphenyl)-1,7-dimethyl-10-oxatricyclo[5.2.1.0$^{2,6}$]decane-3,5-dione

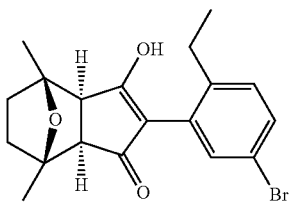 [SMILES: CCc1ccc(Br)cc1C1=C(O)[C@H]2[C@@H](C1=O)[C@]1(C)CC[C@@]2(C)O1]

A solution of (1RS,2SR,6RS,7SR)-4-(5-bromo-2-ethylphenyl)-1,7-dimethyl-10-oxatricyclo[5.2.1.0$^{2,6}$]dec-8-en-3,5-dione (1.63 g, 4.3 mmol) in methanol (200 ml) is hydrogenated at 3.5 bar over 5% palladium on carbon for 1 hour and 30 minutes at room temperature. The catalyst is removed by filtration through diatomaceous earth and the solvent is evaporated under reduced pressure. Trituration with diethyl ether gives (1RS,2SR,6RS,7SR)-4-(5-bromo-2-ethylphenyl)-1,7-dimethyl-10-oxatricyclo[5.2.1.0$^{2,6}$]decane-3,5-dione.

Step 3: Preparation of (1RS,2SR,6RS,7SR)-4-(4'-chloro-4-ethyl-2'-fluorobiphen-3-yl)-1,7-dimethyl-10-oxatricyclo[5.2.1.0$^{2,6}$]decane-3,5-dione

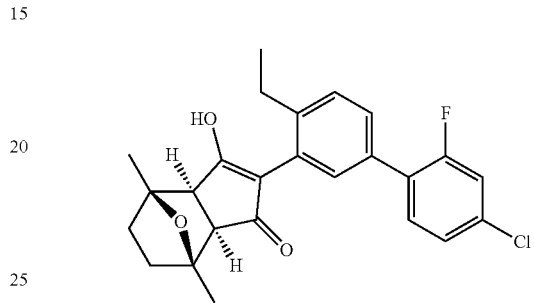

A mixture of (1RS,2SR,6RS,7SR)-4-(5-bromo-2-ethylphenyl)-1,7-dimethyl-10-oxatricyclo[5.2.1.0$^{2,6}$]dec-8-en-3,5-dione (113 mg, 0.3 mmol), 4-chloro-2-fluorophenylboronic acid (103 mg, 0.6 mmol) and cesium fluoride (449 mg, 3.0 mmol) in degassed 1,2-dimethoxyethane (1.5 ml) are stirred under nitrogen at room temperature for 40 minutes. [1,1'-bis(diphenylphosphino) ferrocene]dichloropalladium (II) complex with dichloromethane (48 mg, 0.06 mmol) is added, followed by a further quantity of 1,2-dimethoxyethane (1 ml) and reaction mixture is heated to 80° C. for 18 hours. The mixture is cooled to room temperature, then diluted with dichloromethane and filtered through a small plug of diatomaceous earth. The filtrate is evaporated and the residue is purified by column chromatography on silica gel, to give (1RS,2SR,6RS,7SR)-4-(4'-chloro-4-ethyl-2'-fluorobiphen-3-yl)-1,7-dimethyl-10-oxatricyclo-[5.2.1.0$^{2,6}$]decane-3,5-dione.

$^1$H NMR (400 MHz, d$_4$-MeOH) 7.45-7.43 (1H, m), 7.38-7.31 (2H, m), 7.16-7.13 (3H, m), 2.78 (2H, br. s), 2.54 (2H, br. m), 1.75-1.70 (4H, m), 1.56 (6H, s), 1.15 (3H, t)

Example 6

Preparation of (1RS,2SR,6RS,7SR)-4-(3-ethyl-4'-fluorobiphen-4-yl)-10-oxatricyclo-[5.2.1.0$^{2,6}$]decane-3,5-dione

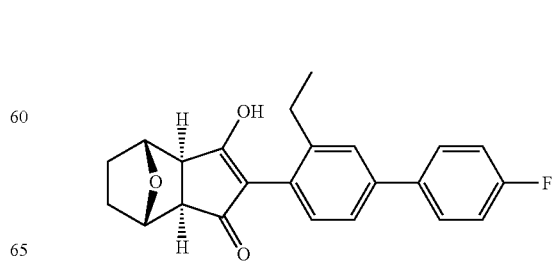

Step 1: Preparation of 4-bromo-2-ethylphenyllead triacetate

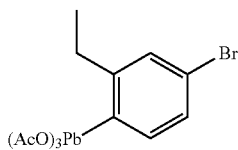

Dry chloroform (30 ml) is added to a mixture of lead tetraacetate (8.52 g, 19.3 mmol) and mercuric diacetate (0.28 g, 0.875 mmol) under an atmosphere of nitrogen, and the reaction mixture is stirred and heated to 40° C. 4-Bromo-2-ethylphenylboronic acid (4.0 g, 17.5 mmol) is added in one portion and the mixture is stirred at 40° C. for 4 hours. The reaction mixture is cooled to 0° C., and potassium carbonate (2.66 g, 19.3 mmol) is added portionwise. The mixture is stirred for 5 minutes, then filtered through a small plug of diatomaceous earth, washing with chloroform. The filtrate concentrated under reduced pressure to give 4-bromo-2-ethylphenyllead triacetate.

Step 2: Preparation of (1RS,2SR,6RS,7SR)-4-(4-bromo-2-ethylphenyl)-10-oxatricyclo-[5.2.1.0$^{2,6}$]decane-3,5-dione

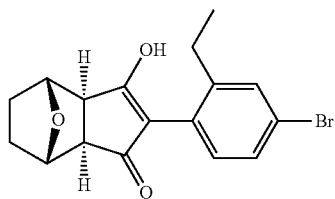 [SMILES: CCc1cc(Br)ccc1C1=C(O)[C@H]2[C@@H](C1=O)[C@@H]1CC[C@H]2O1]

4-Dimethylaminopyridine (3.67 g, 30.0 mmol) and toluene (10 ml) are added to a solution of (1RS,2SR,6RS,7SR)-10-oxatricyclo[5.2.1.0$^{2,6}$]decane-3,5-dione (1.0 g, 6.0 mmol) in chloroform (40 ml) and the reaction mixture is heated to 80° C. 4-Bromo-2-ethylphenyllead triacetate (5.13 g, 9.04 mmol) is added portionwise over 20 minutes, and once the addition is complete the reaction mixture is stirred at 80° C. for a further 4 hours. The mixture is cooled to room temperature, 2M aqueous hydrochloric acid (40 ml) is added, and the mixture is stirred vigorously for 15 minutes, then filtered through a small plug of diatomaceous earth, washing with dichloromethane (40 ml). The organic phase is separated, and the aqueous phase is extracted with dichloromethane. The organic solutions are combined, dried over anhydrous magnesium sulfate, filtered and the filtrate is concentrated under reduced pressure. The residue is purified by column chromatography on silica gel to give (1RS,2SR,6RS,7SR)-4-(4-bromo-2-ethylphenyl)-10-oxatricyclo[5.2.1.0$^{2,6}$]-decane-3,5-dione.

Step 3: Preparation of (1RS,2SR,6RS,7SR)-4-(3-ethyl-4'-fluorobiphen-4-yl)-10-oxatricyclo-[5.2.1.0$^{2,6}$]decane-3,5-dione

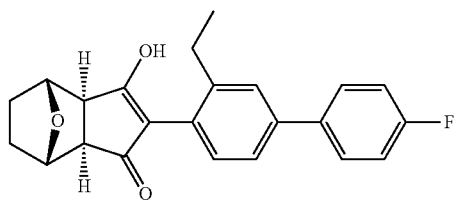 [SMILES: CCc1cc(-c2ccc(F)cc2)ccc1C1=C(O)[C@H]2[C@@H](C1=O)[C@@H]1CC[C@H]2O1]

A mixture of (1RS,2SR,6RS,7SR)-4-(4-bromo-2-ethylphenyl)-10-oxatricyclo-[5.2.1.0$^{2,6}$]decane-3,5-dione (200 mg, 0.57 mmol), 4-fluorophenylboronic acid (112 mg, 0.80 mmol) and cesium fluoride (260 mg, 1.71 mmol) are stirred together in degassed 1,2-dimethoxyethane (5 ml) at room temperature under an atmosphere of nitrogen for 40 minutes at room temperature. [1,1-bis(diphenylphosphino)ferrocene]dichloropalladium(II) complex with dichloromethane (74 mg, 0.09 mmol) is added, and the reaction mixture is heated to 80° C. for 20 hours. The mixture is cooled to room temperature, filtered through a plug of diatomaceous earth, washing with 2M aqueous hydrochloric acid and dichloromethane. The organic phase is collected, and the aqueous phase is extracted with dichloromethane. The organic solutions are combined, dried over anhydrous magnesium sulfate, filtered and the filtrate is concentrated under reduced pressure. The residue is purified by column choramtography on silica gel to give (1RS,2SR,6RS,7SR)-4-(3-ethyl-4'-fluorobiphen-4-yl)-10-oxatricyclo[5.2.1.0$^{2,6}$]decane-3,5-dione.

$^1$H NMR (400 MHz, d$_4$-MeOH) δ$_H$ 7.62 (2H, m), 7.46 (1H, m), 7.39 (1H, dd), 7.15 (2H, m), 7.06° (1H, d), 4.61 (2H, m), 2.85 (2H, s), 2.53 (2H, q), 1.78-1.86 (2H, m) 1.63-1.70 (2H, m), 1.12 (3H, t)

Additional compounds in Table T1 below are prepared by similar methods using appropriate starting materials.

Where more than one tautomer or rotational conformer is observed in the proton NMR spectrum, the data shown below are for the mixture of isomers and conformers.

TABLE T1

| Compound Number | Structure | $^1$H nmr (CDCl$_3$ unless stated) or other physical data |
|---|---|---|
| T1 | 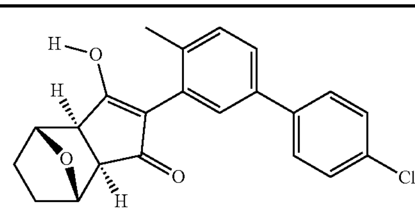 | δ$_H$ 7.52-7.19 (7H, m), 4.62-4.58 (2H, m), 2.69-2.67 (2H, m), 2.12 (3H, s), 1.76-1.73 (2H, m), 1.47-1.41 (2H, m). |

TABLE T1-continued

| Compound Number | Structure | ¹H nmr (CDCl₃ unless stated) or other physical data |
|---|---|---|
| T2 | 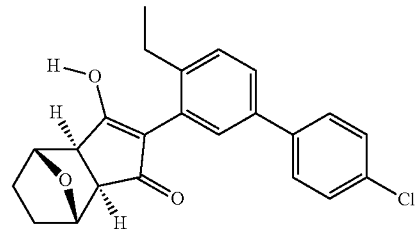 [SMILES: CCc1ccc(-c2ccc(Cl)cc2)cc1C1=C(O)[C@H]2[C@@H](C1=O)[C@@H]1CC[C@H]2O1] | $\delta_H$ 7.61-7.18 (7H, m), 4.62 (2H, br. s), 2.85 (2H, br. s), 2.52 (2H, q), 1.86-1.78 (2H, m), 1.68-1.63 (2H, m), 1.11 (3H, t). |
| T3 | 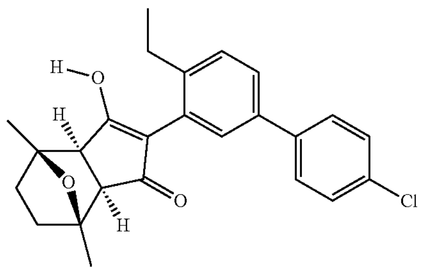 [SMILES: CCc1ccc(-c2ccc(Cl)cc2)cc1C1=C(O)[C@H]2[C@@H](C1=O)[C@]1(C)CC[C@@]2(C)O1] | $\delta_H$ 7.51-7.47 (3H, m), 7.40-7.37 (3H, m), 7.23 (1H, apparent s), 2.81 (2H, br. s), 2.60-2.53 (2H, m), 1.75-1.72 (4H, m), 1.58 (6H, s), 1.16 (3H, t). |
| T4 | 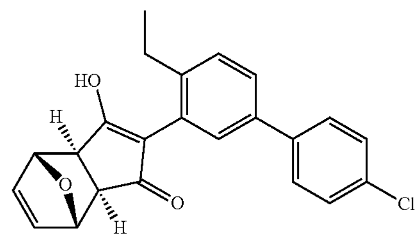 [SMILES: CCc1ccc(-c2ccc(Cl)cc2)cc1C1=C(O)[C@H]2[C@@H](C1=O)[C@@H]1C=C[C@H]2O1] | $\delta_H$ 7.52-7.47 (3H, m), 7.40-7.37 (3H, m), 7.25 (1H, m), 6.51 (2H, s), 5.10 (2H, br. s), 2.81 (2H, br. s), 2.53 (2H, q), 1.15-1.12 (3H, m). |
| T5 | 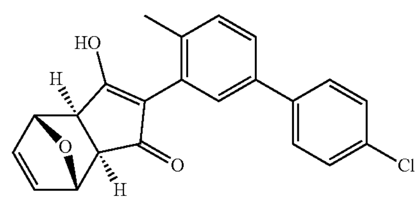 [SMILES: Cc1ccc(-c2ccc(Cl)cc2)cc1C1=C(O)[C@H]2[C@@H](C1=O)[C@@H]1C=C[C@H]2O1] | $\delta_H$ 7.31-7.10 (7H, m), 6.54-6.49 (2H, m), 5.17 (1H, s), 5.13 (1H, s), 3.16 (1H, d), 2.77 (1H, d), 2.26 (3H, s). |
| T6 | 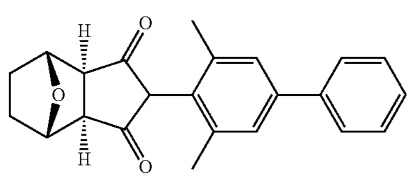 [SMILES: Cc1cc(-c2ccccc2)cc(C)c1C1C(=O)[C@@H]2[C@H](C1=O)[C@H]1CC[C@@H]2O1] | (d₄-MeOH) $\delta_H$ 7.60 (2H, d), 7.43 (2H, t), 7.39-7.31 (3H, m), 4.64 (2H, m), 2.90 (2H, s), 2.19 (6H, s), 1.88-1.82 (2H, m), 1.73-1.67 (2H, m). |
| T7 | 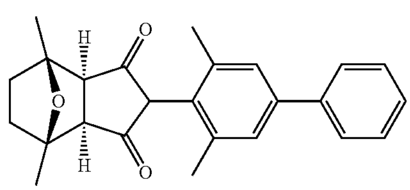 [SMILES: Cc1cc(-c2ccccc2)cc(C)c1C1C(=O)[C@@H]2[C@H](C1=O)[C@@]1(C)CC[C@]2(C)O1] | $\delta_H$ 7.55 (2H, d), 7.43 (2H, t), 7.36-7.30 (3H, m), 3.03 (1H, d), 2.69 (1H, d), 2.24 (3H, s), 2.18 (3H, s), 1.80-1.70 (4H, m), 1.57 (d, 6H). |
| T8 | 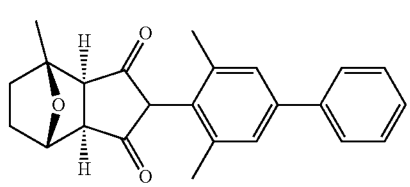 [SMILES: Cc1cc(-c2ccccc2)cc(C)c1C1C(=O)[C@H]2[C@@H]3CC[C@@](C)(O3)[C@H]2C1=O] | $\delta_H$ 7.56 (2H, d), 7.43 (2H, t), 7.36-7.31 (3H, m), 4.70 (0.5H, d), 4.66 (0.5H, d), 3.08 (0.5H, d), 2.94 (0.5H, d), 2.83 (0.5H, d), 2.62 (0.5H, d), 2.23 (3H, d), 2.18 (H, s), 2.04-1.94 (1H, m), 1.69-1.59 (6H, m). |

TABLE T1-continued

| Compound Number | Structure | ¹H nmr (CDCl₃ unless stated) or other physical data |
|---|---|---|
| T9 | 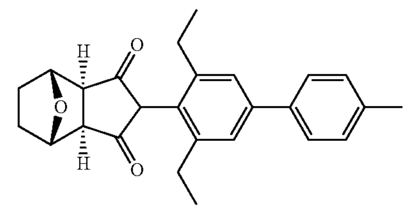 [SMILES: CCc1cc(-c2ccc(C)cc2)cc(CC)c1C1C(=O)[C@@H]2[C@H](C1=O)[C@H]1CC[C@@H]2O1] | δ$_H$ 7.47 (2H, d), 7.32 (2H, d), 7.24 (2H, d), 6.99 (1H, br s), 4.72 (2H, s), 2.96 (1H, br s), 2.73 (1H, br s), 2.47 (4H, br m), 2.39 (3H, s), 1.84 (2H, br s), 1.58 (2H, d), 1.1 (6H, m). |
| T10 | 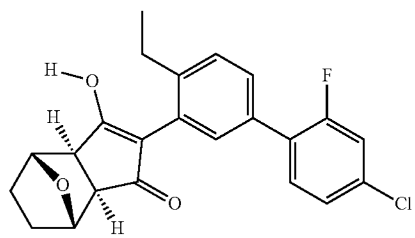 | (d₄-MeOH) δ$_H$ 7.48-7.41 (2H, m), 7.34 (1H, d), 7.26-7.24 (2H, m), 7.15 (1H, s), 4.61 (2H, s), 2.85 (2H, s), 2.51 (2H, q), 1.82-1.80 (2H, m), 1.65 (2H, d), 1.11 (3H, t). |
| T11 | 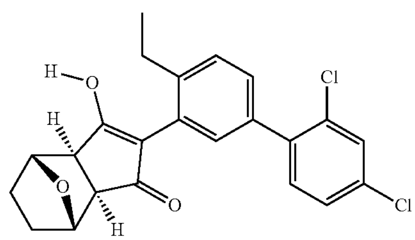 [SMILES: CCc1ccc(-c2ccc(Cl)cc2Cl)cc1C1=C(O)[C@H]2[C@@H](C1=O)[C@@H]1CC[C@H]2O1] | (d₄-MeOH) δ$_H$ 7.52-7.51 (1H, m), 7.35-7.32 (4H, m), 7.03 (1H, s), 4.61-4.60 (2H, m), 2.84 (2H, s), 2.52 (2H, q), 1.82-1.79 (2H, m), 1.67-1.64 (2H, m), 1.12 (3H, t). |
| T12 | 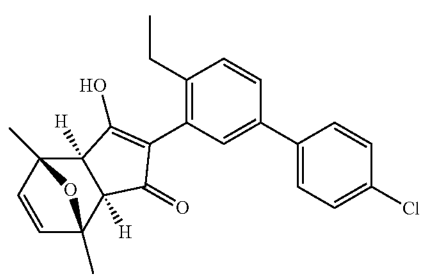 [SMILES: CCc1ccc(-c2ccc(Cl)cc2)cc1C1=C(O)[C@H]2[C@@H](C1=O)[C@]1(C)C=C[C@@]2(C)O1] | (d₄-MeOH) δ$_H$ 7.59-7.56 (2H, m), 7.51 (1H, dd), 7.42-7.39 (2H, m), 7.35 (1H, d), 7.26 (1H, d), 6.36 (2H, s), 2.80 (2H, s), 2.54 (2H, q), 1.63 (6H, s), 1.12 (3H, t). |
| T13 | 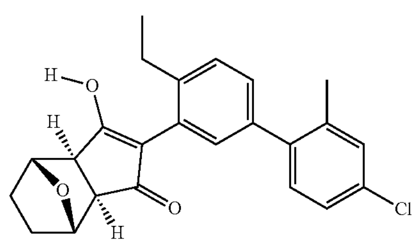 [SMILES: CCc1ccc(-c2ccc(Cl)cc2C)cc1C1=C(O)[C@H]2[C@@H](C1=O)[C@@H]1CC[C@H]2O1] | δ$_H$ 7.28 (1H, s), 7.17-7.11 (4H, m), 6.96 (1H, s), 4.63 (2H, s), 2.73 (2H, s), 2.51-2.46 (2H, m), 2.22 (3H, s), 1.79 (2H, br. m), 1.55 (2H, d), 1.10 (3H, t). |
| T14 | 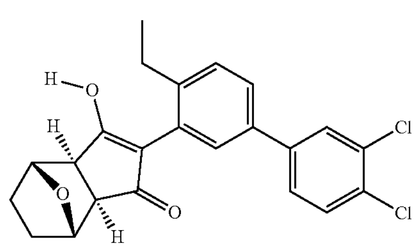 [SMILES: CCc1ccc(-c2ccc(Cl)c(Cl)c2)cc1C1=C(O)[C@H]2[C@@H](C1=O)[C@@H]1CC[C@H]2O1] | δ$_H$ 7.60 (1H, s), 7.38-7.36 (3H, br. m), 7.29-7.27 (1H, br. m), 7.20 (1H, br. s), 4.65 (2H, s), 2.70 (2H, br. s), 2.50-2.40 (2H, br. m), 1.77 (2H, br. s), 1.49 (2H, br. s), 1.09 (3H, br. s). |

TABLE T1-continued

| Compound Number | Structure | $^1$H nmr (CDCl$_3$ unless stated) or other physical data |
|---|---|---|
| T15 | 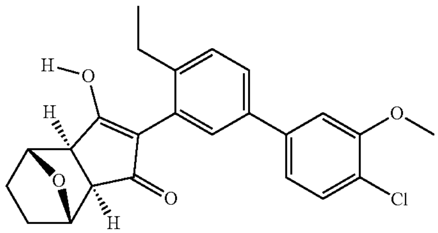 [SMILES: CCc1ccc(-c2ccc(Cl)c(OC)c2)cc1C1=C(O)[C@H]2[C@@H](C1=O)[C@@H]1CC[C@H]2O1] | $\delta_H$ 7.41 (1H, d), 7.31 (2H, t), 7.22 (1H, br. s), 7.09-7.04 (2H, m), 4.66 (2H, s), 3.91 (3H, s), 2.75 (2H, s), 2.50-2.45 (2H, q), 1.82-1.80 (2H, m), 1.56 (2H, d), 1.09 (3H, t). |
| T16 | 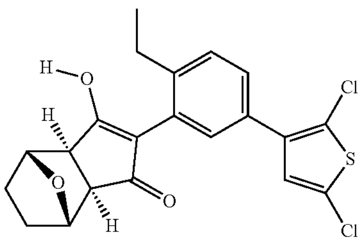 [SMILES: CCc1ccc(-c2cc(Cl)sc2Cl)cc1C1=C(O)[C@H]2[C@@H](C1=O)[C@@H]1CC[C@H]2O1] | $\delta_H$ 7.42 (1H, d), 7.28 (1H, d), 7.15 (1H, s), 6.87 (1H, s), 4.65 (2H, s), 2.71 (2H, s), 2.50-2.48 (2H, m), 1.77 (2H, br. s), 1.50 (2H, br. s), 1.13-1.08 (3H, br. m). |
| T17 | 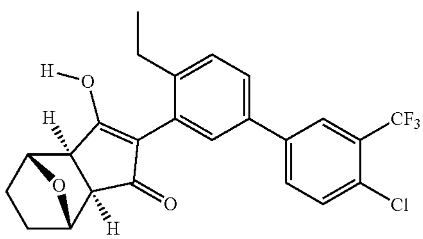 [SMILES: CCc1ccc(-c2ccc(Cl)c(C(F)(F)F)c2)cc1C1=C(O)[C@H]2[C@@H](C1=O)[C@@H]1CC[C@H]2O1] | $\delta_H$ 7.86 (1H, s), 7.65 (1H, s), 7.51-7.30 (4H, m), 4.70 (2H, s), 2.77-2.55 (4H, m), 1.82 (2H, br. s), 1.55 (2H, br. s), 1.15 (3H, br. apparent s). |
| T18 | 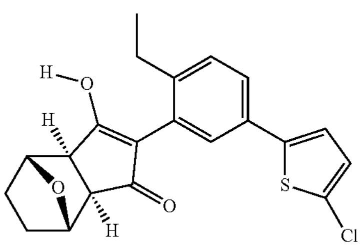 [SMILES: CCc1ccc(-c2ccc(Cl)s2)cc1C1=C(O)[C@H]2[C@@H](C1=O)[C@@H]1CC[C@H]2O1] | $\delta_H$ 7.56-7.54 (1H, br. m), 7.36-7.34 (1H, m), 7.22-7.18 (1H, m), 6.98 (1H, s), 6.82 (1H, s), 4.67 (2H, s), 2.73 (2H, s), 2.47-2.40 (2H, m), 1.79 (2H, s), 1.52 (2H, s), 1.09 (3H, br. apparent s). |
| T19 | 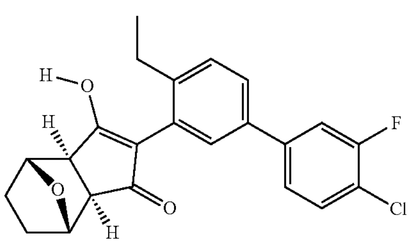 [SMILES: CCc1ccc(-c2ccc(Cl)c(F)c2)cc1C1=C(O)[C@H]2[C@@H](C1=O)[C@@H]1CC[C@H]2O1] | $\delta_H$ 7.41-7.38 (1H, m), 7.35 (1H, d), 7.30 (2H, d), 7.24-7.21 (2H, br. m), 4.66 (2H, s), 2.73 (2H, s), 2.51-2.46 (2H, m), 1.80-1.78 (2H, m), 1.52 (2H, d), 1.10 (3H, t). |
| T20 | 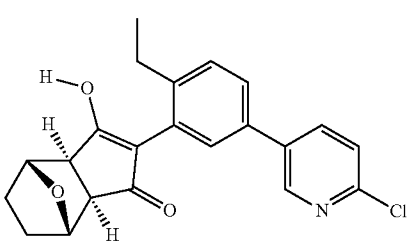 [SMILES: CCc1ccc(-c2ccc(Cl)nc2)cc1C1=C(O)[C@H]2[C@@H](C1=O)[C@@H]1CC[C@H]2O1] | $\delta_H$ 7.79-7.71 (2H, m), 7.22-7.20 (2H, m), 7.08-7.02 (2H, br. m), 4.75 (2H, s), 2.58-2.53 (4H, m), 1.85-1.84 (2H, br. m), 1.58 (2H, d), 1.08 (3H, t). |

TABLE T1-continued

| Compound Number | Structure | ¹H nmr (CDCl₃ unless stated) or other physical data |
|---|---|---|
| T21 | 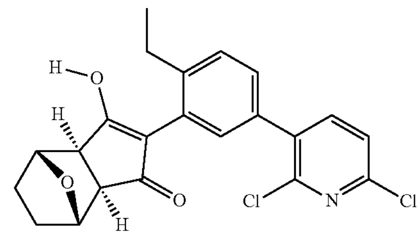 [SMILES: CCc1ccc(-c2ccc(Cl)nc2Cl)cc1C1=C(O)[C@H]2[C@@H](C1=O)[C@@H]1CC[C@H]2O1] | $\delta_H$ 7.65-7.63 (1H, m), 7.32-7.26 (3H, m), 7.06 (1H, s), 4.64 (2H, s), 2.73 (2H, s), 2.50-2.48 (2H, m), 1.80-1.79 (2H, m), 1.54-1.53 (2H, m), 1.12-1.07 (3H, m). |
| T22 | 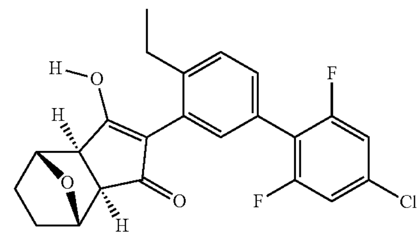 [SMILES: CCc1ccc(-c2c(F)cc(Cl)cc2F)cc1C1=C(O)[C@H]2[C@@H](C1=O)[C@@H]1CC[C@H]2O1] | $\delta_H$ 7.37-7.32 (2H, m), 7.13 (1H, br. s), 6.98 (2H, d), 4.69 (2H, s), 2.75-2.53 (4H, m), 1.81 (2H, br. s), 1.55 (2H, br. s), 1.14 (3H, t). |
| T23 | 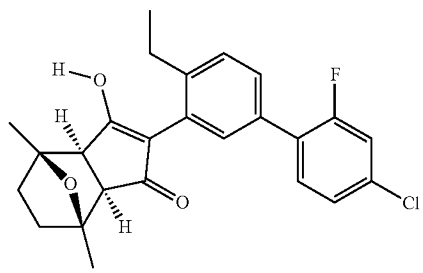 [SMILES: CCc1ccc(-c2ccc(Cl)cc2F)cc1C1=C(O)[C@H]2[C@@H](C1=O)[C@]1(C)CC[C@@]2(C)O1] | (d₄-MeOH) $\delta_H$ 7.45-7.43 (1H, m), 7.38-7.31 (2H, m), 7.16-7.13 (3H, m), 2.78 (2H, br. s), 2.54 (2H, br. m), 1.75-1.70 (4H, m), 1.56 (6H, s), 1.15 (3H, t) |
| T24 | 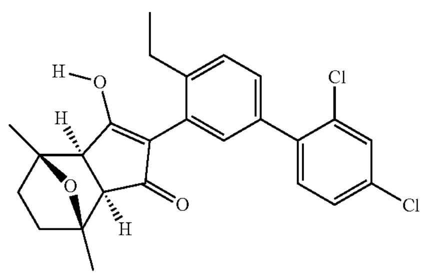 [SMILES: CCc1ccc(-c2ccc(Cl)cc2Cl)cc1C1=C(O)[C@H]2[C@@H](C1=O)[C@]1(C)CC[C@@]2(C)O1] | (d₄-MeOH) $\delta_H$ 7.52 (1H), 7.37-7.34 (4H, m), 7.05 (1H, s), 2.85 (2H, s), 2.56-2.54 (2H, m), 1.85-1.81 (2H, m), 1.69-1.66 (2H, m), 1.52 (6H, s), 1.14 (3H, t) |
| T25 | 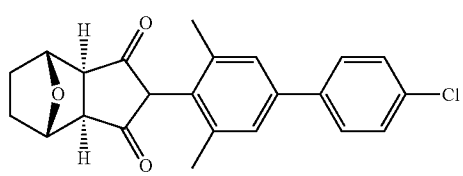 [SMILES: Cc1cc(-c2ccc(Cl)cc2)cc(C)c1C1C(=O)[C@@H]2[C@H](C1=O)[C@H]1CC[C@@H]2O1] | (d₄-MeOH) $\delta_H$ 7.58 (2H, d), 7.40 (2H, d), 7.28 (2H, s), 4.61 (2H, m), 2.87 (2H, s), 2.15 (6H, s), 1.82 (2H, m), 1.67 (2H, m) |
| T26 | 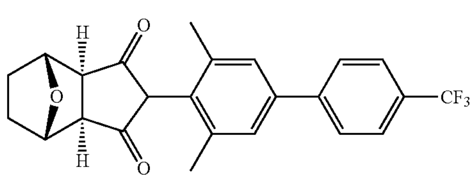 [SMILES: Cc1cc(-c2ccc(C(F)(F)F)cc2)cc(C)c1C1C(=O)[C@@H]2[C@H](C1=O)[C@H]1CC[C@@H]2O1] | (d₆-DMSO) $\delta_H$ 7.80 (2H, d), 7.74 (2H, d), 7.31 (2H, s), 4.46 (2H, s), 2.73 (2H, s), 2.04 (6H, s), 1.61 (2H, m), 1.51 (2H, m) |
| T27 | 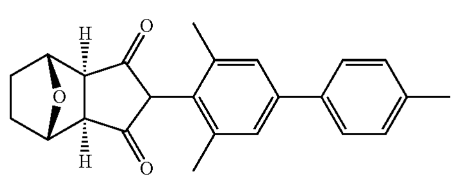 [SMILES: Cc1ccc(-c2cc(C)c(C3C(=O)[C@@H]4[C@H](C3=O)[C@H]3CC[C@@H]4O3)c(C)c2)cc1] | (d₃-Acetonitrile) $\delta_H$ 7.55 (2H, d), 7.33 (2H, s), 7.28 (2H, d), 4.60 (2H, d), 2.85 (2H, s), 2.16 (6H, d), 1.80 (2H, m), 1.65 (2H, m) |

TABLE T1-continued

| Compound Number | Structure | ¹H nmr (CDCl₃ unless stated) or other physical data |
|---|---|---|
| T28 | 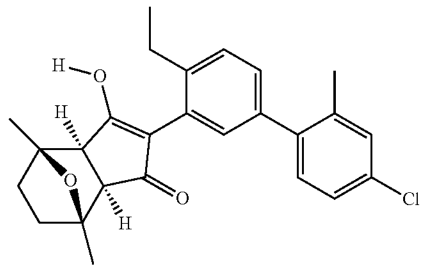 [SMILES: CCc1ccc(-c2ccc(Cl)cc2C)cc1C1=C(O)[C@H]2[C@@H](C1=O)[C@]1(C)CC[C@@]2(C)O1] | δ$_H$ 7.29 (1H, d), 7.20-7.07 (4H, m), 6.91 (1H, s), 2.73 (2H, br. s), 2.52 (2H, br. m), 2.22 (3H, s), 1.68 (4H, s), 1.53 (6H, s), 1.13 (3H, t). |
| T29 | 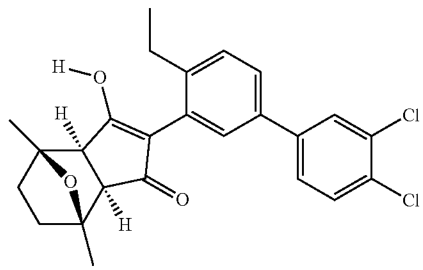 [SMILES: CCc1ccc(-c2ccc(Cl)c(Cl)c2)cc1C1=C(O)[C@H]2[C@@H](C1=O)[C@]1(C)CC[C@@]2(C)O1] | δ$_H$ 7.59 (1H, s), 7.43 (2H, d), 7.34 (2H, d), 7.17 (1H, s), 2.76 (2H, br. s), 2.52 (2H, br. m), 1.71 (4H, s), 1.54 (6H, s), 1.12 (3H, t). |
| T30 | 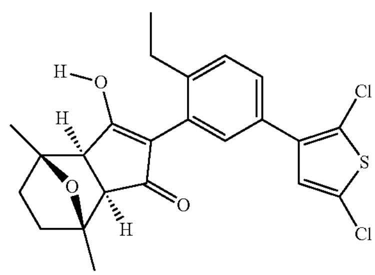 [SMILES: CCc1ccc(-c2cc(Cl)sc2Cl)cc1C1=C(O)[C@H]2[C@@H](C1=O)[C@]1(C)CC[C@@]2(C)O1] | δ$_H$ 7.45 (1H, d), 7.35 (1H, d), 7.17 (1H, d), 6.87 (1H, s), 2.78 (2H, br. s), 2.57-2.53 (2H, br. m), 1.75-1.70 (4H, m), 1.56 (6H, s), 1.14 (3H, t). |
| T31 | 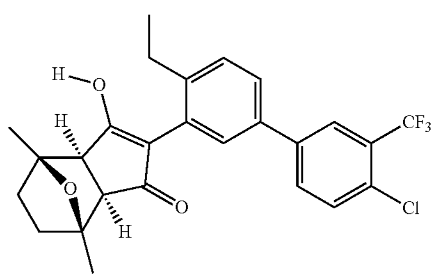 [SMILES: CCc1ccc(-c2ccc(Cl)c(C(F)(F)F)c2)cc1C1=C(O)[C@H]2[C@@H](C1=O)[C@]1(C)CC[C@@]2(C)O1] | δ$_H$ 7.80 (1H, s), 7.59 (1H, d), 7.46 (2H, dd), 7.35 (1H, d), 7.18 (1H, s), 2.76 (2H, br. s), 2.50 (2H, br. apparent s), 1.69 (4H, s), 1.54 (6H, s), 1.12 (3H, t). |
| T32 | 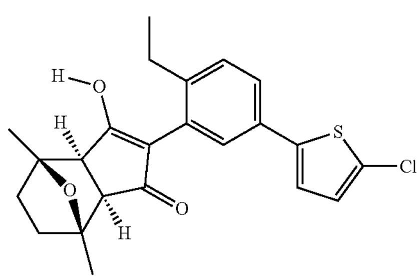 [SMILES: CCc1ccc(-c2ccc(Cl)s2)cc1C1=C(O)[C@H]2[C@@H](C1=O)[C@]1(C)CC[C@@]2(C)O1] | δ$_H$ 7.35 (1H, d), 7.22 (1H, d), 7.11 (1H, s), 6.96 (1H, d), 6.82 (1H, d), 2.68 (2H, s), 2.44 (2H, br. apparent s), 1.64 (4H, s), 1.51 (6H, s), 1.07 (3H, t). |

TABLE T1-continued

| Compound Number | Structure | ¹H nmr (CDCl₃ unless stated) or other physical data |
|---|---|---|
| T33 | 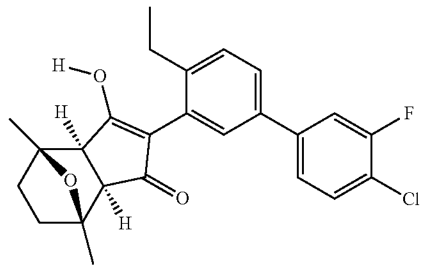 [SMILES: CCc1ccc(-c2ccc(Cl)c(F)c2)cc1C1=C(O)[C@H]2[C@@H](C1=O)[C@]1(C)CC[C@@]2(C)O1] | δ_H 7.42-7.21 (5H, m), 7.14 (1H, s), 2.71 (2H, br. s), 2.49-2.47 (2H, br. m), 1.68 (4H, s), 1.52 (6H, s), 1.10 (3H, t). |
| T34 | 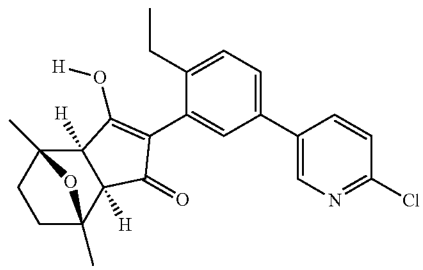 [SMILES: CCc1ccc(-c2ccc(Cl)nc2)cc1C1=C(O)[C@H]2[C@@H](C1=O)[C@]1(C)CC[C@@]2(C)O1] | δ_H 7.67 (1H, d), 7.51 (1H, s), 7.15 (2H, br. s), 6.94-6.88 (2H, m), 2.57 (4H, br. m), 1.76-1.72 (4H, br. m), 1.63 (6H, br. s), 1.09 (3H, t). |
| T35 | 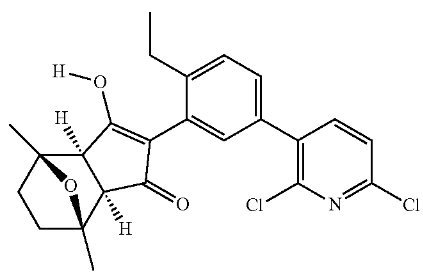 [SMILES: CCc1ccc(-c2ccc(Cl)nc2Cl)cc1C1=C(O)[C@H]2[C@@H](C1=O)[C@]1(C)CC[C@@]2(C)O1] | δ_H 7.63 (1H, d), 7.38 (2H, s), 7.29 (1H, d), 7.12 (1H, s), 2.81 (2H, br. s), 2.57 (2H, br. m), 1.76-1.71 (4H, m), 1.57 (6H, s), 1.17 (3H, t). |
| T36 | 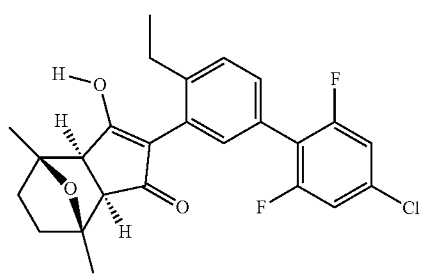 [SMILES: CCc1ccc(-c2c(F)cc(Cl)cc2F)cc1C1=C(O)[C@H]2[C@@H](C1=O)[C@]1(C)CC[C@@]2(C)O1] | δ_H 7.42-7.37 (2H, m), 7.11 (1H, s), 7.01-6.99 (2H, m), 2.60-2.53 (3H, m), 2.00 (1H, s), 1.76-1.71 (4H, m), 1.57 (6H, s), 1.17 (3H, t). |
| T37 | 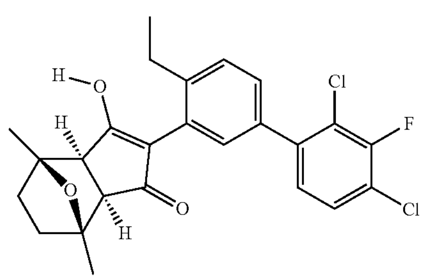 [SMILES: CCc1ccc(-c2ccc(Cl)c(F)c2Cl)cc1C1=C(O)[C@H]2[C@@H](C1=O)[C@]1(C)CC[C@@]2(C)O1] | δ_H 7.40 (1H, d), 7.35-7.33 (1H, m), 7.16-7.13 (2H, m), 7.10-7.06 (1H, m), 2.72 (2H, br. s), 2.50-2.49 (2H, br. m), 1.68 (4H, s), 1.53 (6H, s), 1.12 (3H, t). |

TABLE T1-continued

| Compound Number | Structure | ¹H nmr (CDCl₃ unless stated) or other physical data |
|---|---|---|
| T38 | 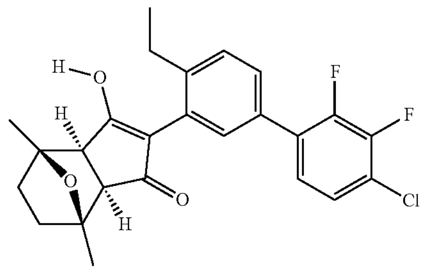 [SMILES: CCc1ccc(-c2ccc(Cl)c(F)c2F)cc1C1=C(O)[C@H]2[C@@H](C1=O)[C@]1(C)CC[C@@]2(C)O1] | $\delta_H$ 7.32-7.27 (2H, br. m), 7.04-7.02 (3H, br. m), 2.82-2.67 (2H, br. m), 2.51 (2H, s), 1.69 (4H, s), 1.53 (6H, s), 1.13 (3H, t). |
| T39 | 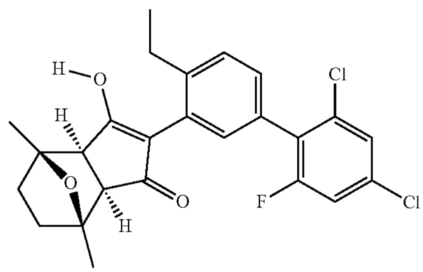 [SMILES: CCc1ccc(-c2c(F)cc(Cl)cc2Cl)cc1C1=C(O)[C@H]2[C@@H](C1=O)[C@]1(C)CC[C@@]2(C)O1] | $\delta_H$ 7.41 (1H, d), 7.31-7.29 (2H, m), 7.10 (1H, dd), 7.01 (1H, br. s), 2.79 (2H, br. s), 2.61-2.53 (2H, m), 1.76-1.71 (4H, m), 1.57 (6H, s), 1.18 (3H, t). |
| T40 | 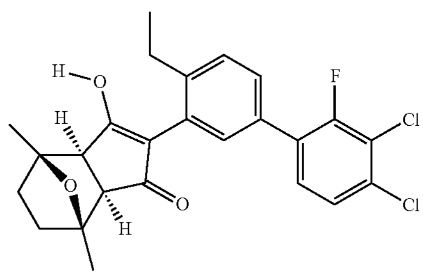 [SMILES: CCc1ccc(-c2ccc(Cl)c(Cl)c2F)cc1C1=C(O)[C@H]2[C@@H](C1=O)[C@]1(C)CC[C@@]2(C)O1] | (d₆-acetone) $\delta_H$ 7.50-7.43 (3H, m), 7.36 (1H, d), 7.19 (1H, s), 2.83 (2H, br. s), 2.58 (2H, q), 1.81-1.77 (2H, m), 1.63-1.60 (2H, m), 1.50 (6H, s), 1.13 (3H, t). |
| T41 | 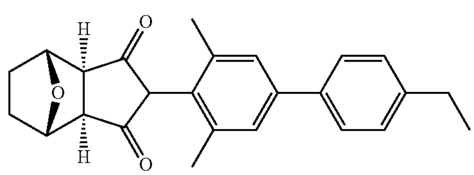 [SMILES: CCc1ccc(-c2cc(C)c(C3C(=O)[C@@H]4[C@H](C3=O)[C@H]3CC[C@@H]4O3)c(C)c2)cc1] | (d₆-DMSO) $\delta_H$ 7.55 (2H, d), 7.28 (2H, d), 7.26 (2H, s), 4.52 (2H, s), 2.80 (2H, s), 2.64 (2H, q), 2.07 (6H, d), 1.68 (2H, m), 1.57 (2H, m), 1.21 (3H, t). |
| T42 | 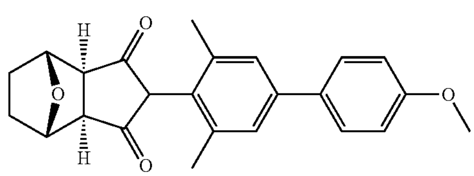 | (d₆-DMSO) $\delta_H$ 7.57 (2H, d), 7.24 (2H, s), 7.01 (2H, d), 4.52 (2H, s), 3.79 (3H, s), 2.80 (2H, s), 2.08 (6H, d), 1.67 (2H, m), 1.57 (2H, m). |
| T43 | 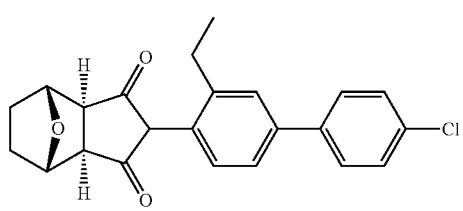 [SMILES: CCc1cc(-c2ccc(Cl)cc2)ccc1C1C(=O)[C@@H]2[C@H](C1=O)[C@H]1CC[C@@H]2O1] | (d₄-methanol) $\delta_H$ 7.61 (2H, dd), 7.49 (1H, d), 7.39-7.45 (3H, m), 7.08 (1H, dd), 4.62 (2H, s), 2.85 (2H, s), 2.54 (2H, q), 1.79-1.86 (2H, m), 1.67 (2H, m), 1.13 (3H, t). |
| T44 | 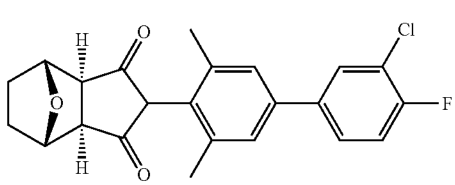 [SMILES: Cc1cc(-c2ccc(F)c(Cl)c2)cc(C)c1C1C(=O)[C@@H]2[C@H](C1=O)[C@H]1CC[C@@H]2O1] | $\delta_H$ 7.50 (2H, d), 7.40 (1H, m), 7.10 (2H, d), 4.50 (2H, s), 2.80 (2H, s), 2.10 (6H, d), 1.70 (2H, m), 1.40 (2H, d). |

TABLE T1-continued
| Compound Number | Structure | $^1$H nmr (CDCl$_3$ unless stated) or other physical data |
|---|---|---|
| T45 | 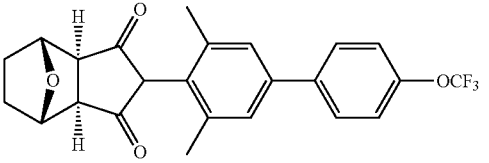 [SMILES: Cc1cc(-c2ccc(OC(F)(F)F)cc2)cc(C)c1C1C(=O)[C@@H]2[C@H](C1=O)[C@H]1CC[C@@H]2O1] | δ$_H$ 7.50 (2H, d), 7.20 (4H, m), 4.40 (2H, m), 2.80 (2H, m), 2.00 (6H, d), 1.60 (2H, m), 1.50 (2H, d). |
| T46 | 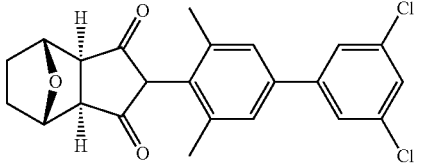 [SMILES: Cc1cc(-c2cc(Cl)cc(Cl)c2)cc(C)c1C1C(=O)[C@@H]2[C@H](C1=O)[C@H]1CC[C@@H]2O1] | δ$_H$ 7.50 (1H, d), 7.40 (1H, s), 7.35 (1H, d), 7.10 (2H, d), 4.50 (2H, s), 2.80 (2H, s), 2.10 (6H, s), 1.70 (2H, m), 1.40 (2H, d). |
| T47 | 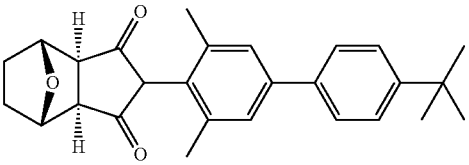 [SMILES: Cc1cc(-c2ccc(C(C)(C)C)cc2)cc(C)c1C1C(=O)[C@@H]2[C@H](C1=O)[C@H]1CC[C@@H]2O1] | δ$_H$ 7.50 (2H, d), 7.40 (2H, s), 7.20 (2H, s), 4.50 (2H, s), 2.80 (2H, m), 2.00 (6H, d), 1.65 (2H, m), 1.50 (2H, d), 1.20 (9H, s). |
| T48 | 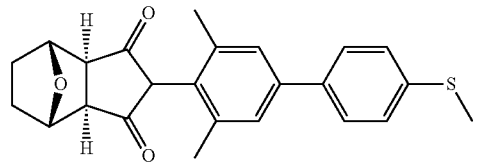 [SMILES: CSc1ccc(-c2cc(C)c(C3C(=O)[C@@H]4[C@H](C3=O)[C@H]3CC[C@@H]4O3)c(C)c2)cc1] | δ$_H$ 7.60 (2H, d), 7.30 (2H, d), 7.20 (2H, s), 4.50 (2H, s), 2.80 (2H, m), 2.50 (3H, s), 2.00 (6H, d), 1.65 (2H, m), 1.50 (2H, d). |
| T49 | 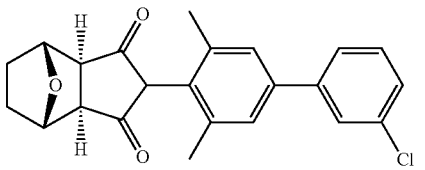 [SMILES: Cc1cc(-c2cccc(Cl)c2)cc(C)c1C1C(=O)[C@@H]2[C@H](C1=O)[C@H]1CC[C@@H]2O1] | δ$_H$ 7.60 (1H, s), 7.50 (1H, d), 7.40 (1H, m), 7.35 (1H, m), 7.30 (2H, s), 4.50 (2H, m), 2.70 (2H, m), 2.00 (6H, d), 1.60 (2H, m), 1.50 (2H, d). |
| T50 | 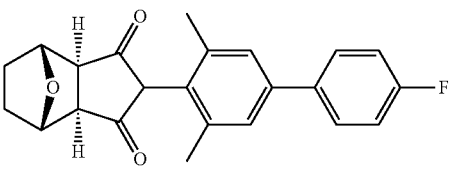 [SMILES: Cc1cc(-c2ccc(F)cc2)cc(C)c1C1C(=O)[C@@H]2[C@H](C1=O)[C@H]1CC[C@@H]2O1] | δ$_H$ 7.60 (2H, m), 7.20 (4H, m), 4.40 (2H, m), 2.80 (2H, m), 2.00 (6H, d), 1.60 (2H, m), 1.50 (2H, d). |
| T51 | 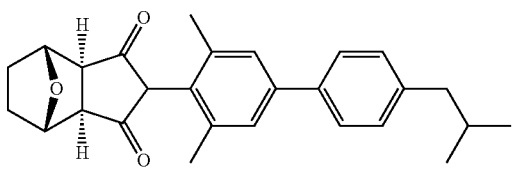 [SMILES: Cc1cc(-c2ccc(CC(C)C)cc2)cc(C)c1C1C(=O)[C@@H]2[C@H](C1=O)[C@H]1CC[C@@H]2O1] | δ$_H$ 7.50 (2H, m), 7.20 (2H, s), 7.15 (2H, d), 4.40 (2H, m), 3.70 (2H, m), 2.40 (2H, m), 2.00 (6H, d), 1.80 (1H, m), 1.60 (2H, m), 1.50 (2H, d), 1.08 (6H, d). |
| T52 | 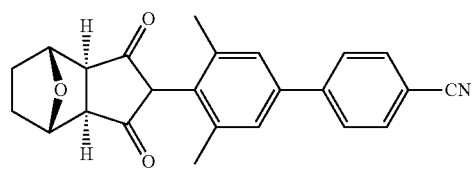 [SMILES: Cc1cc(-c2ccc(C#N)cc2)cc(C)c1C1C(=O)[C@@H]2[C@H](C1=O)[C@H]1CC[C@@H]2O1] | δ$_H$ 7.70 (2H, m), 7.30 (4H, m), 4.40 (2H, m), 2.80 (2H, m), 2.00 (6H, d), 1.60 (2H, m), 1.50 (2H, d). |

TABLE T1-continued

| Compound Number | Structure | $^1$H nmr (CDCl$_3$ unless stated) or other physical data |
|---|---|---|
| T53 | 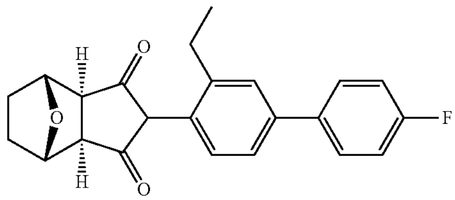 [SMILES: CCc1cc(-c2ccc(F)cc2)ccc1C1C(=O)[C@@H]2[C@H](C1=O)[C@H]1CC[C@@H]2O1] | (d$_4$-methanol) $\delta_H$ 7.62 (2H, m), 7.46 (1H, m), 7.39 (1H, dd), 7.15 (2H, m), 7.06 (1H, d), 4.61 (2H, m), 2.85 (2H, s), 2.53 (2H, q), 1.78-1.86 (2H, m), 1.63-1.70 (2H, m), 1.12 (3H, t). |

The compounds of the following Tables 1 to 192 can be obtained in an analogous manner.

Table 1 covers 252 compounds of the type T-1

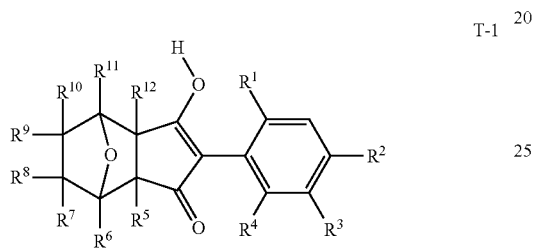

T-1 wherein $R^1$ is methyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

| Compound Number | $R^2$ | $R^3$ |
|---|---|---|
| 1.001 | phenyl | H |
| 1.002 | 2-fluorophenyl | H |
| 1.003 | 3-fluorophenyl | H |
| 1.004 | 4-fluorophenyl | H |
| 1.005 | 2-chlorophenyl | H |
| 1.006 | 3-chlorophenyl | H |
| 1.007 | 4-chlorophenyl | H |
| 1.008 | 2-bromophenyl | H |
| 1.009 | 3-bromophenyl | H |
| 1.010 | 4-bromophenyl | H |
| 1.011 | 2-methylphenyl | H |
| 1.012 | 3-methylphenyl | H |
| 1.013 | 4-methylphenyl | H |
| 1.014 | 4-ethylphenyl | H |
| 1.015 | 4-isopropylphenyl | H |
| 1.016 | 4-isobutylphenyl | H |
| 1.017 | 4-tert-butylphenyl | H |
| 1.018 | 2-cyanophenyl | H |
| 1.019 | 3-cyanophenyl | H |
| 1.020 | 4-cyanophenyl | H |
| 1.021 | 2-methoxyphenyl | H |
| 1.022 | 3-methoxyphenyl | H |
| 1.023 | 4-methoxyphenyl | H |
| 1.024 | 2-trifluoromethylphenyl | H |
| 1.025 | 3-trifluoromethylphenyl | H |
| 1.026 | 4-trifluoromethylphenyl | H |
| 1.027 | 4-trifluoromethoxyphenyl | H |
| 1.028 | 4-difluoromethoxyphenyl | H |
| 1.029 | 4-methylthiophenyl | H |
| 1.030 | 4-methylsulfinylphenyl | H |
| 1.031 | 4-methylsulfonylphenyl | H |
| 1.032 | 4-trifluoromethylthiophenyl | H |
| 1.033 | 4-trifluoromethylsulfinylphenyl | H |
| 1.034 | 4-trifluoromethylsulfonylphenyl | H |
| 1.035 | 2,3-difluorophenyl | H |

-continued

| Compound Number | R² | R³ |
|---|---|---|
| 1.036 | 2,4-difluorophenyl | H |
| 1.037 | 2,5-difluorophenyl | H |
| 1.038 | 2,6-difluorophenyl | H |
| 1.039 | 3,4-difluorophenyl | H |
| 1.040 | 3,5-difluorophenyl | H |
| 1.041 | 2,3-dichlorophenyl | H |
| 1.042 | 2,4-dichlorophenyl | H |
| 1.043 | 2,5-dichlorophenyl | H |
| 1.044 | 2,6-dichlorophenyl | H |
| 1.045 | 3,4-dichlorophenyl | H |
| 1.046 | 3,5-dichlorophenyl | H |
| 1.047 | 2,3,4-trichlorophenyl | H |
| 1.048 | 2,3,5-trichlorophenyl | H |
| 1.049 | 2,3,6-trichlorophenyl | H |
| 1.050 | 2,4,5-trichlorophenyl | H |
| 1.051 | 2,4,6-trichlorophenyl | H |
| 1.052 | 3,4,5-trichlorophenyl | H |
| 1.053 | 2-chloro-3-fluorophenyl | H |
| 1.054 | 2-chloro-4-fluorophenyl | H |
| 1.055 | 2-chloro-4-fluorophenyl | H |
| 1.056 | 2-chloro-4-fluorophenyl | H |
| 1.057 | 3-chloro-2-fluorophenyl | H |
| 1.058 | 3-chloro-4-fluorophenyl | H |
| 1.059 | 3-chloro-5-fluorophenyl | H |
| 1.060 | 4-chloro-2-fluorophenyl | H |
| 1.061 | 4-chloro-3-fluorophenyl | H |
| 1.062 | 5-chloro-2-fluorophenyl | H |
| 1.063 | 4-chloro-2-methylphenyl | H |
| 1.064 | 4-chloro-3-methylphenyl | H |
| 1.065 | 4-chloro-2-trifluoromethylphenyl | H |
| 1.066 | 4-chloro-3-trifluoromethylphenyl | H |
| 1.067 | 4-chloro-2-cyanophenyl | H |
| 1.068 | 4-chloro-3-cyanophenyl | H |
| 1.069 | 4-chloro-2-methoxyphenyl | H |
| 1.070 | 4-chloro-3-methoxyphenyl | H |
| 1.071 | 4-fluoro-2-methylphenyl | H |
| 1.072 | 4-fluoro-3-methylphenyl | H |
| 1.073 | 4-fluoro-2-trifluoromethylphenyl | H |
| 1.074 | 4-fluoro-3-trifluoromethylphenyl | H |
| 1.075 | 2-fluoro-4-trifluoromethylphenyl | H |
| 1.076 | 3-fluoro-4-trifluoromethylphenyl | H |
| 1.077 | 2,3,4-trifluorophenyl | H |
| 1.078 | 2,3,5-trifluorophenyl | H |
| 1.079 | 2,3,6-trifluorophenyl | H |
| 1.080 | 2,4,5-trifluorophenyl | H |
| 1.081 | 2,4,6-trifluorophenyl | H |
| 1.082 | 3,4,5-trifluorophenyl | H |
| 1.083 | 3,4-dichloro-2-fluorophenyl | H |
| 1.084 | 3,4-dichoro-5-fluorophenyl | H |
| 1.085 | 4,5-dichloro-2-fluorophenyl | H |
| 1.086 | 2-chloro-3,4-difluorophenyl | H |
| 1.087 | 2-chloro-4,5-difluorophenyl | H |
| 1.088 | 2-chloro-4,6-difluorophenyl | H |
| 1.089 | 3-chloro-4,5-difluorophenyl | H |
| 1.090 | 3,4-methylenedioxyphenyl | H |
| 1.091 | benzo[1,3]diox-5-yl | H |
| 1.092 | 2,3-dihydrobenzo[1,4]dioxin-6-yl | H |
| 1.093 | 2-naphthyl | H |
| 1.094 | 2-pyridyl | H |
| 1.095 | 3-pyridyl | H |
| 1.096 | 4-pyridyl | H |
| 1.097 | 3-chloropyridin-2-yl | H |
| 1.098 | 4-chloropyridin-2-yl | H |
| 1.099 | 5-chloropyridin-2-yl | H |
| 1.100 | 6-chloropyridin-2-yl | H |
| 1.101 | 2-chloropyridin-3-yl | H |
| 1.102 | 4-chloropyridin-3-yl | H |
| 1.103 | 2-chloropyridin-4-yl | H |
| 1.104 | 3-chloropyridin-4-yl | H |
| 1.105 | 2-chloropyridin-5-yl | H |
| 1.106 | 3-chloropyridin-5-yl | H |
| 1.107 | 3-methylpyridin-2-yl | H |
| 1.108 | 4-methylpyridin-2-yl | H |
| 1.109 | 5-methylpyridin-2-yl | H |
| 1.110 | 6-methylpyridin-2-yl | H |
| 1.111 | 2-methylpyridin-3-yl | H |

-continued

| Compound Number | R² | R³ |
|---|---|---|
| 1.112 | 4-methylpyridin-3-yl | H |
| 1.113 | 2-methylpyridin-4-yl | H |
| 1.114 | 3-methylpyridin-4-yl | H |
| 1.115 | 2-methylpyridin-5-yl | H |
| 1.116 | 3-methylpyridinyl-5-yl | H |
| 1.117 | 2-trifluoromethylpyridin-5-yl | H |
| 1.118 | 3-trifluoromethylpyridin-5-yl | H |
| 1.119 | 2,6-dichloropyridin-3-yl | H |
| 1.120 | 2-chloro-4-methylpyridin-5-yl | H |
| 1.121 | 6-chloro-2-methylpyridin-3-yl | H |
| 1.122 | 5-chlorothiophen-2-yl | H |
| 1.123 | 2-chlorothiophen-3-yl | H |
| 1.124 | 2,5-dichlorothiophen-3-yl | H |
| 1.125 | 1-methylpyrazol-4-yl | H |
| 1.126 | 4-chloropyrazol-1-yl | H |
| 1.127 | H | phenyl |
| 1.128 | H | 2-fluorophenyl |
| 1.129 | H | 3-fluorophenyl |
| 1.130 | H | 4-fluorophenyl |
| 1.131 | H | 2-chlorophenyl |
| 1.132 | H | 3-chlorophenyl |
| 1.133 | H | 4-chlorophenyl |
| 1.134 | H | 2-bromophenyl |
| 1.135 | H | 3-bromophenyl |
| 1.136 | H | 4-bromophenyl |
| 1.137 | H | 2-methylphenyl |
| 1.138 | H | 3-methylphenyl |
| 1.139 | H | 4-methylphenyl |
| 1.140 | H | 4-ethylphenyl |
| 1.141 | H | 4-isopropylphenyl |
| 1.142 | H | 4-isobutylphenyl |
| 1.143 | H | 4-tert-butylphenyl |
| 1.144 | H | 2-cyanophenyl |
| 1.145 | H | 3-cyanophenyl |
| 1.146 | H | 4-cyanophenyl |
| 1.147 | H | 2-methoxyphenyl |
| 1.148 | H | 3-methoxyphenyl |
| 1.149 | H | 4-methoxyphenyl |
| 1.150 | H | 2-trifluoromethylphenyl |
| 1.151 | H | 3-trifluoromethylphenyl |
| 1.152 | H | 4-trifluoromethylphenyl |
| 1.153 | H | 4-trifluoromethoxyphenyl |
| 1.154 | H | 4-difluoromethoxyphenyl |
| 1.155 | H | 4-methylthiophenyl |
| 1.156 | H | 4-methylsulfinylphenyl |
| 1.157 | H | 4-methylsulfonylphenyl |
| 1.158 | H | 4-trifluoromethylthiophenyl |
| 1.159 | H | 4-trifluoromethylsulfinylphenyl |
| 1.160 | H | 4-trifluoromethylsulfonylphenyl |
| 1.161 | H | 2,3-difluorophenyl |
| 1.162 | H | 2,4-difluorophenyl |
| 1.163 | H | 2,5-difluorophenyl |
| 1.164 | H | 2,6-difluorophenyl |
| 1.165 | H | 3,4-difluorophenyl |
| 1.166 | H | 3,5-difluorophenyl |
| 1.167 | H | 2,3-dichlorophenyl |
| 1.168 | H | 2,4-dichlorophenyl |
| 1.169 | H | 2,5-dichlorophenyl |
| 1.170 | H | 2,6-dichlorophenyl |
| 1.171 | H | 3,4-dichlorophenyl |
| 1.172 | H | 3,5-dichlorophenyl |
| 1.173 | H | 2,3,4-trichlorophenyl |
| 1.174 | H | 2,3,5-trichlorophenyl |
| 1.175 | H | 2,3,6-trichlorophenyl |
| 1.176 | H | 2,4,5-trichlorophenyl |
| 1.177 | H | 2,4,6-trichlorophenyl |
| 1.178 | H | 3,4,5-trichlorophenyl |
| 1.179 | H | 2-chloro-3-fluorophenyl |
| 1.180 | H | 2-chloro-4-fluorophenyl |
| 1.181 | H | 2-chloro-4-fluorophenyl |
| 1.182 | H | 2-chloro-4-fluorophenyl |
| 1.183 | H | 3-chloro-2-fluorophenyl |
| 1.184 | H | 3-chloro-4-fluorophenyl |
| 1.185 | H | 3-chloro-5-fluorophenyl |
| 1.186 | H | 4-chloro-2-fluorophenyl |
| 1.187 | H | 4-chloro-3-fluorophenyl |

-continued

| Compound Number | R² | R³ |
|---|---|---|
| 1.188 | H | 5-chloro-2-fluorophenyl |
| 1.189 | H | 4-chloro-2-methylphenyl |
| 1.190 | H | 4-chloro-3-methylphenyl |
| 1.191 | H | 4-chloro-2-trifluoromethylphenyl |
| 1.192 | H | 4-chloro-3-trifluoromethylphenyl |
| 1.193 | H | 4-chloro-2-cyanophenyl |
| 1.194 | H | 4-chloro-3-cyanophenyl |
| 1.195 | H | 4-chloro-2-methoxyphenyl |
| 1.196 | H | 4-chloro-3-methoxyphenyl |
| 1.197 | H | 4-fluoro-2-methylphenyl |
| 1.198 | H | 4-fluoro-3-methylphenyl |
| 1.199 | H | 4-fluoro-2-trifluoromethylphenyl |
| 1.200 | H | 4-fluoro-3-trifluoromethylphenyl |
| 1.201 | H | 2-fluoro-4-trifluoromethylphenyl |
| 1.202 | H | 3-fluoro-4-trifluoromethylphenyl |
| 1.203 | H | 2,3,4-trifluorophenyl |
| 1.204 | H | 2,3,5-trifluorophenyl |
| 1.205 | H | 2,3,6-trifluorophenyl |
| 1.206 | H | 2,4,5-trifluorophenyl |
| 1.207 | H | 2,4,6-trifluorophenyl |
| 1.208 | H | 3,4,5-trifluorophenyl |
| 1.209 | H | 3,4-dichloro-2-fluorophenyl |
| 1.210 | H | 3,4-dichoro-5-fluorophenyl |
| 1.211 | H | 4,5-dichloro-2-fluorophenyl |
| 1.212 | H | 2-chloro-3,4-difluorophenyl |
| 1.213 | H | 2-chloro-4,5-difluorophenyl |
| 1.214 | H | 2-chloro-4,6-difluorophenyl |
| 1.215 | H | 3-chloro-4,5-difluorophenyl |
| 1.216 | H | 3,4-methylenedioxyphenyl |
| 1.217 | H | benzo[1,3]diox-5-yl |
| 1.218 | H | 2,3-dihydrobenzo[1,4]dioxin-6-yl |
| 1.219 | H | 2-naphthyl |
| 1.220 | H | 2-pyridyl |
| 1.221 | H | 3-pyridyl |
| 1.222 | H | 4-pyridyl |
| 1.223 | H | 3-chloropyridin-2-yl |
| 1.224 | H | 4-chloropyridin-2-yl |
| 1.225 | H | 5-chloropyridin-2-yl |
| 1.226 | H | 6-chloropyridin-2-yl |
| 1.227 | H | 2-chloropyridin-3-yl |
| 1.228 | H | 4-chloropyridin-3-yl |
| 1.229 | H | 2-chloropyridin-4-yl |
| 1.230 | H | 3-chloropyridin-4-yl |
| 1.231 | H | 2-chloropyridin-5-yl |
| 1.232 | H | 3-chloropyridin-5-yl |
| 1.233 | H | 3-methylpyridin-2-yl |
| 1.234 | H | 4-methylpyridin-2-yl |
| 1.235 | H | 5-methylpyridin-2-yl |
| 1.236 | H | 6-methylpyridin-2-yl |
| 1.237 | H | 2-methylpyridin-3-yl |
| 1.238 | H | 4-methylpyridin-3-yl |
| 1.239 | H | 2-methylpyridin-4-yl |
| 1.240 | H | 3-methylpyridin-4-yl |
| 1.241 | H | 2-methylpyridin-5-yl |
| 1.242 | H | 3-methylpyridinyl-5-yl |
| 1.243 | H | 2-trifluoromethylpyridin-5-yl |
| 1.244 | H | 3-trifluoromethylpyridin-5-yl |
| 1.245 | H | 2,6-dichloropyridin-3-yl |
| 1.246 | H | 2-chloro-4-methylpyridin-5-yl |
| 1.247 | H | 6-chloro-2-methylpyridin-3-yl |
| 1.248 | H | 5-chlorothiophen-2-yl |
| 1.249 | H | 2-chlorothiophen-3-yl |
| 1.250 | H | 2,5-dichlorothiophen-3-yl |
| 1.251 | H | 1-methylpyrazol-4-yl |
| 1.252 | H | 4-chloropyrazol-1-yl |

Table 2 covers 252 compounds of the type T-1 wherein $R^1$ is methyl, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 3 covers 252 compounds of the type T-1 wherein $R^1$ is methyl, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 4 covers 252 compounds of the type T-1 wherein $R^1$ is methyl, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 5 covers 252 compounds of the type T-1 wherein $R^1$ is methyl, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 6 covers 252 compounds of the type T-1 wherein $R^1$ is methyl, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 7 covers 252 compounds of the type T-1 wherein $R^1$ is methyl, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 8 covers 252 compounds of the type T-1 wherein $R^1$ is methyl, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 9 covers 252 compounds of the type T-1 wherein $R^1$ is methyl, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 10 covers 252 compounds of the type T-1 wherein $R^1$ is methyl, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 11 covers 252 compounds of the type T-1 wherein $R^1$ is methyl, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 12 covers 252 compounds of the type T-1 wherein $R^1$ is methyl, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 13 covers 252 compounds of the type T-1 wherein $R^1$ is ethyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

Table 14 covers 252 compounds of the type T-1 wherein $R^1$ is ethyl, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 15 covers 252 compounds of the type T-1 wherein $R^1$ is ethyl, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 16 covers 252 compounds of the type T-1 wherein $R^1$ is ethyl, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 17 covers 252 compounds of the type T-1 wherein $R^1$ is ethyl, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 18 covers 252 compounds of the type T-1 wherein $R^1$ is ethyl, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 19 covers 252 compounds of the type T-1 wherein $R^1$ is ethyl, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 20 covers 252 compounds of the type T-1 wherein $R^1$ is ethyl, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 21 covers 252 compounds of the type T-1 wherein $R^1$ is ethyl, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 22 covers 252 compounds of the type T-1 wherein $R^1$ is ethyl, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 23 covers 252 compounds of the type T-1 wherein $R^1$ is ethyl, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 24 covers 252 compounds of the type T-1 wherein $R^1$ is ethyl, $R^4$ is hydrogen, $R^5$ is hydrogen, $R^6$ is methyl, $R^7$, $R^8$, $R^9$, $R^{16}$ are hydrogen, $R^{11}$ is methyl, $R^{12}$ is hydrogen and $R^2$ and $R^3$ are as defined in Table 1.

Table 25 covers 252 compounds of the type T-1 wherein $R^1$ and $R^4$ are methyl, $R^5$, $R^6$, $R^7$, $R^8$, $R^9$, $R^{10}$, $R^{11}$ and $R^{12}$ are hydrogen and $R^2$ and $R^3$ are as defined in Table 1.

Table 26 covers 252 compounds of the type T-1 wherein $R^1$ and $R^4$ are methyl, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 27 covers 252 compounds of the type T-1 wherein $R^1$ and $R^4$ are methyl, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 28 covers 252 compounds of the type T-1 wherein $R^1$ and $R^4$ are methyl, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 29 covers 252 compounds of the type T-1 wherein $R^1$ and $R^4$ are methyl, $R^5$ is hydrogen, $R^8$ is ethoxymethyl, $R^7$, $R^8$, $R^9$, $R^{10}$, $R^{11}$ and $R^{12}$ are hydrogen and $R^2$ and $R^3$ are as defined in Table 1.

Table 30 covers 252 compounds of the type T-1 wherein W and $R^4$ are methyl, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 31 covers 252 compounds of the type T-1 wherein $R^1$ and $R^4$ are methyl, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 32 covers 252 compounds of the type T-1 wherein $R^1$ and $R^4$ are methyl, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 33 covers 252 compounds of the type T-1 wherein $R^1$ and $R^4$ are methyl, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 34 covers 252 compounds of the type T-1 wherein $R^1$ and $R^4$ are methyl, $R^5$, $R^6$ and $R^7$ are hydrogen, $R^e$ is ethoxymethyl, $R^9$, $R^{10}$, $R^{11}$ and $R^{12}$ are hydrogen and $R^2$ and $R^3$ are as defined in Table 1.

Table 35 covers 252 compounds of the type T-1 wherein $R^1$ and $R^4$ are methyl, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 36 covers 252 compounds of the type T-1 wherein $R^1$ and $R^4$ are methyl, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 37 covers 252 compounds of the type T-1 wherein $R^1$ and $R^4$ are ethyl, $R^5$, $R^6$, $R^7$, $R^8$, $R^9$, $R^{10}$, $R^{11}$ and $R^{12}$ are hydrogen and $R^2$ and $R^3$ are as defined in Table 1.

Table 38 covers 252 compounds of the type T-1 wherein $R^1$ and $R^4$ are ethyl, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 39 covers 252 compounds of the type T-1 wherein $R^1$ and $R^4$ are ethyl, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 40 covers 252 compounds of the type T-1 wherein $R^1$ and $R^4$ are ethyl, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 41 covers 252 compounds of the type T-1 wherein $R^1$ and $R^4$ are ethyl, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 42 covers 252 compounds of the type T-1 wherein $R^1$ and $R^4$ are ethyl, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 43 covers 252 compounds of the type T-1 wherein $R^1$ and $R^4$ are ethyl, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 44 covers 252 compounds of the type T-1 wherein $R^1$ and $R^4$ are ethyl, $R^5$, $R^8$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 45 covers 252 compounds of the type T-1 wherein $R^1$ and $R^4$ are ethyl, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 46 covers 252 compounds of the type T-1 wherein $R^1$ and $R^4$ are ethyl, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 47 covers 252 compounds of the type T-1 wherein $R^1$ and $R^4$ are ethyl, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 48 covers 252 compounds of the type T-1 wherein $R^1$ and $R^4$ are ethyl, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 49 covers 252 compounds of the type T-1 wherein $R^1$ is difluoromethoxy, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1

Table 50 covers 252 compounds of the type T-1 wherein $R^1$ is difluoromethoxy, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 51 covers 252 compounds of the type T-1 wherein $R^1$ is difluoromethoxy, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 52 covers 252 compounds of the type T-1 wherein $R^1$ is difluoromethoxy, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 53 covers 252 compounds of the type T-1 wherein $R^1$ is difluoromethoxy, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 54 covers 252 compounds of the type T-1 wherein $R^1$ is difluoromethoxy, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 55 covers 252 compounds of the type T-1 wherein $R^1$ is difluoromethoxy, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 56 covers 252 compounds of the type T-1 wherein $R^1$ is difluoromethoxy, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 57 covers 252 compounds of the type T-1 wherein $R^1$ is difluoromethoxy, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 58 covers 252 compounds of the type T-1 wherein $R^1$ is difluoromethoxy, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 59 covers 252 compounds of the type T-1 wherein $R^1$ is difluoromethoxy, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 60 covers 252 compounds of the type T-1 wherein $R^1$ is difluoromethoxy, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 61 covers 252 compounds of the type T-1 wherein $R^1$ is trifluoromethoxy, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1

Table 62 covers 252 compounds of the type T-1 wherein $R^1$ is trifluoromethoxy, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 63 covers 252 compounds of the type T-1 wherein $R^1$ is trifluoromethoxy, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 64 covers 252 compounds of the type T-1 wherein $R^1$ is trifluoromethoxy, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 65 covers 252 compounds of the type T-1 wherein $R^1$ is trifluoromethoxy, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 66 covers 252 compounds of the type T-1 wherein $R^1$ is trifluoromethoxy, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 67 covers 252 compounds of the type T-1 wherein $R^1$ is trifluoromethoxy, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 68 covers 252 compounds of the type T-1 wherein $R^1$ is trifluoromethoxy, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 69 covers 252 compounds of the type T-1 wherein $R^1$ is trifluoromethoxy, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 70 covers 252 compounds of the type T-1 wherein $R^1$ is trifluoromethoxy, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 71 covers 252 compounds of the type T-1 wherein $R^1$ is trifluoromethoxy, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 72 covers 252 compounds of the type T-1 wherein $R^1$ is trifluoromethoxy, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 73 covers 252 compounds of the type T-1 wherein $R^1$ is cyclopropyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1

Table 74 covers 252 compounds of the type T-1 wherein $R^1$ is cyclopropyl, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 75 covers 252 compounds of the type T-1 wherein $R^1$ is cyclopropyl, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 76 covers 252 compounds of the type T-1 wherein $R^1$ is cyclopropyl, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 77 covers 252 compounds of the type T-1 wherein $R^1$ is cyclopropyl, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 78 covers 252 compounds of the type T-1 wherein $R^1$ is cyclopropyl, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 79 covers 252 compounds of the type T-1 wherein $R^1$ is cyclopropyl, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 80 covers 252 compounds of the type T-1 wherein $R^1$ is cyclopropyl, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 81 covers 252 compounds of the type T-1 wherein $R^1$ is cyclopropyl, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 82 covers 252 compounds of the type T-1 wherein $R^1$ is cyclopropyl, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 83 covers 252 compounds of the type T-1 wherein $R^1$ is cyclopropyl, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 84 covers 252 compounds of the type T-1 wherein $R^1$ is cyclopropyl, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 85 covers 252 compounds of the type T-1 wherein $R^1$ is chlorine, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1

Table 86 covers 252 compounds of the type T-1 wherein $R^1$ is chlorine, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 87 covers 252 compounds of the type T-1 wherein $R^1$ is chlorine, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 88 covers 252 compounds of the type T-1 wherein $R^1$ is chlorine, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 89 covers 252 compounds of the type T-1 wherein $R^1$ is chlorine, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 90 covers 252 compounds of the type T-1 wherein $R^1$ is chlorine, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 91 covers 252 compounds of the type T-1 wherein $R^1$ is chlorine, $R^4$ is hydrogen, $R^5$, $R^8$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 92 covers 252 compounds of the type T-1 wherein $R^1$ is chlorine, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 93 covers 252 compounds of the type T-1 wherein $R^1$ is chlorine, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 94 covers 252 compounds of the type T-1 wherein $R^1$ is chlorine, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 95 covers 252 compounds of the type T-1 wherein $R^1$ is chlorine, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 96 covers 252 compounds of the type T-1 wherein $R^1$ is chlorine, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 97 covers 252 compounds of the type T-2

T-2 wherein $R^1$ is methyl, $R^4$ is hydrogen, $R^5$, $R^6$, $R^8$, $R^9$, $R^{11}$ and $R^{12}$ are hydrogen and $R^2$ and $R^3$ are as defined in Table 1.

Table 98 covers 252 compounds of the type T-2 wherein $R^1$ is methyl, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 99 covers 252 compounds of the type T-2 wherein $R^1$ is methyl, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 100 covers 252 compounds of the type T-2 wherein $R^1$ is methyl, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 101 covers 252 compounds of the type T-2 wherein $R^1$ is methyl, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 102 covers 252 compounds of the type T-2 wherein $R^1$ is methyl, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 103 covers 252 compounds of the type T-2 wherein $R^1$ is methyl, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 104 covers 252 compounds of the type T-2 wherein $R^1$ is methyl, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 105 covers 252 compounds of the type T-2 wherein $R^1$ is methyl, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 106 covers 252 compounds of the type T-2 wherein $R^1$ is methyl, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 107 covers 252 compounds of the type T-2 wherein $R^1$ is methyl, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 108 covers 252 compounds of the type T-2 wherein $R^1$ is methyl, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 109 covers 252 compounds of the type T-2 wherein $R^1$ is ethyl, $R^4$ is hydrogen, $R^5$, $R^6$, $R^8$, $R^9$, $R^{11}$ and $R^{12}$ are hydrogen and $R^2$ and $R^3$ are as defined in Table 1.

Table 110 covers 252 compounds of the type T-2 wherein $R^1$ is ethyl, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 111 covers 252 compounds of the type T-2 wherein $R^1$ is ethyl, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 112 covers 252 compounds of the type T-2 wherein $R^1$ is ethyl, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 113 covers 252 compounds of the type T-2 wherein $R^1$ is ethyl, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 114 covers 252 compounds of the type T-2 wherein $R^1$ is ethyl, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 115 covers 252 compounds of the type T-2 wherein $R^1$ is ethyl, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 116 covers 252 compounds of the type T-2 wherein $R^1$ is ethyl, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 117 covers 252 compounds of the type T-2 wherein $R^1$ is ethyl, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 118 covers 252 compounds of the type T-2 wherein $R^1$ is ethyl, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 119 covers 252 compounds of the type T-2 wherein $R^1$ is ethyl, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 120 covers 252 compounds of the type T-2 wherein $R^1$ is ethyl, $R^4$ is hydrogen, $R^5$ is hydrogen, $R^6$ is methyl, $R^7$ and $R^9$ are hydrogen, $R^{11}$ is methyl, $R^{12}$ is hydrogen and $R^2$ and $R^3$ are as defined in Table 1.

Table 121 covers 252 compounds of the type T-2 wherein $R^1$ and $R^4$ are methyl, $R^5$, $R^6$, $R^8$, $R^9$, $R^{11}$ and $R^{12}$ are hydrogen and $R^2$ and $R^3$ are as defined in Table 1.

Table 122 covers 252 compounds of the type T-2 wherein $R^1$ and $R^4$ are methyl, $R^5$ is hydrogen, $R^6$ is methyl, $R^8$, $R^9$, $R^{11}$ and $R^{12}$ are hydrogen and $R^2$ and $R^3$ are as defined in Table 1.

Table 123 covers 252 compounds of the type T-2 wherein $R^1$ and $R^4$ are methyl, $R^5$ is hydrogen, $R^6$ is ethyl, $R^8$, $R^9$, $R^{11}$ and $R^{12}$ are hydrogen and $R^2$ and $R^3$ are as defined in Table 1.

Table 124 covers 252 compounds of the type T-2 wherein $R^1$ and $R^4$ are methyl, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 125 covers 252 compounds of the type T-2 wherein $R^1$ and $R^4$ are methyl, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 126 covers 252 compounds of the type T-2 wherein $R^1$ and $R^4$ are methyl, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 127 covers 252 compounds of the type T-2 wherein $R^1$ and $R^4$ are methyl, $R^5$ and $R^6$ are hydrogen, $R^8$ is methyl, $R^9$, $R^{11}$ and $R^{12}$ are hydrogen and $R^2$ and $R^3$ are as defined in Table 1.

Table 128 covers 252 compounds of the type T-2 wherein $R^1$ and $R^4$ are methyl, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 129 covers 252 compounds of the type T-2 wherein $R^1$ and $R^4$ are methyl, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 130 covers 252 compounds of the type T-2 wherein $R^1$ and $R^4$ are methyl, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 131 covers 252 compounds of the type T-2 wherein $R^1$ and $R^4$ are methyl, $R^5$ and $R^8$ are hydrogen, $R^8$ is methoxyethyl, $R^9$, $R^{11}$ and $R^{12}$ are hydrogen and $R^2$ and $R^3$ are as defined in Table 1.

Table 132 covers 252 compounds of the type T-2 wherein $R^1$ and $R^4$ are methyl, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 133 covers 252 compounds of the type T-2 wherein $R^1$ and $R^4$ are ethyl, $R^5$, $R^6$, $R^8$, $R^9$, $R^{11}$ and $R^{12}$ are hydrogen and $R^2$ and $R^3$ are as defined in Table 1.

Table 134 covers 252 compounds of the type T-2 wherein $R^1$ and $R^4$ are ethyl, $R^5$ is hydrogen, $R^8$ is methyl, $R^8$, $R^9$, $R^{11}$ and $R^{12}$ are hydrogen and $R^2$ and $R^3$ are as defined in Table 1.

Table 135 covers 252 compounds of the type T-2 wherein $R^1$ and $R^4$ are ethyl, $R^5$ is hydrogen, $R^6$ is ethyl, $R^8$, $R^9$, $R^{11}$ and $R^{12}$ are hydrogen and $R^2$ and $R^3$ are as defined in Table 1.

Table 136 covers 252 compounds of the type T-2 wherein $R^1$ and $R^4$ are ethyl, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 137 covers 252 compounds of the type T-2 wherein $R^1$ and $R^4$ are ethyl, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 138 covers 252 compounds of the type T-2 wherein $R^1$ and $R^4$ are ethyl, $R^5$ is hydrogen, $R^8$ is methoxyethyl, $R^8$, $R^9$, $R^{11}$ and $R^{12}$ are hydrogen and $R^2$ and $R^3$ are as defined in Table 1.

Table 139 covers 252 compounds of the type T-2 wherein $R^1$ and $R^4$ are ethyl, $R^5$ and $R^6$ are hydrogen, $R^8$ is methyl, $R^9$, $R^{11}$ and $R^{12}$ are hydrogen and $R^2$ and $R^3$ are as defined in Table 1.

Table 140 covers 252 compounds of the type T-2 wherein $R^1$ and $R^4$ are ethyl, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 141 covers 252 compounds of the type T-2 wherein $R^1$ and $R^4$ are ethyl, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 142 covers 252 compounds of the type T-2 wherein $R^1$ and $R^4$ are ethyl, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 143 covers 252 compounds of the type T-2 wherein $R^1$ and $R^4$ are ethyl, $R^5$ and $R^6$ and are hydrogen, $R^8$ is methoxyethyl, $R^9$, $R^{11}$ and $R^{12}$ are hydrogen and $R^2$ and $R^3$ are as defined in Table 1.

Table 144 covers 252 compounds of the type T-2 wherein $R^1$ and $R^4$ are ethyl, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 145 covers 252 compounds of the type T-2 wherein $R^1$ is difluoromethoxy, $R^4$ is hydrogen, $R^5$, $R^6$, $R^8$, $R^9$, $R^{11}$ and $R^{12}$ are hydrogen and $R^2$ and $R^3$ are as defined in Table 1

Table 146 covers 252 compounds of the type T-2 wherein $R^1$ is difluoromethoxy, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 147 covers 252 compounds of the type T-2 wherein $R^1$ is difluoromethoxy, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 148 covers 252 compounds of the type T-2 wherein $R^1$ is difluoromethoxy, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 149 covers 252 compounds of the type T-2 wherein $R^1$ is difluoromethoxy, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 150 covers 252 compounds of the type T-2 wherein $R^1$ is difluoromethoxy, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 151 covers 252 compounds of the type T-2 wherein $R^1$ is difluoromethoxy, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 152 covers 252 compounds of the type T-2 wherein $R^1$ is difluoromethoxy, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 153 covers 252 compounds of the type 1-2 wherein $R^1$ is difluoromethoxy, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 154 covers 252 compounds of the type T-2 wherein $R^1$ is difluoromethoxy, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 155 covers 252 compounds of the type T-2 wherein $R^1$ is difluoromethoxy, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 156 covers 252 compounds of the type T-2 wherein $R^1$ is difluoromethoxy, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 157 covers 252 compounds of the type T-2 wherein $R^1$ is trifluoromethoxy, $R^4$ is hydrogen, $R^5$, $R^6$, $R^8$, $R^9$, $R^{11}$ and $R^{12}$ are hydrogen and $R^2$ and $R^3$ are as defined in Table 1

Table 158 covers 252 compounds of the type T-2 wherein $R^1$ is trifluoromethoxy, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 159 covers 252 compounds of the type T-2 wherein $R^1$ is trifluoromethoxy, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 160 covers 252 compounds of the type T-2 wherein $R^1$ is trifluoromethoxy, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 161 covers 252 compounds of the type T-2 wherein $R^1$ is trifluoromethoxy, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 162 covers 252 compounds of the type T-2 wherein $R^1$ is trifluoromethoxy, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 163 covers 252 compounds of the type T-2 wherein $R^1$ is trifluoromethoxy, $R^4$ is hydrogen, $R^5$ and $R^6$ are hydrogen, $R^6$ is methyl, $R^9$, $R^{11}$ and $R^{12}$ are hydrogen and $R^2$ and $R^3$ are as defined in Table 1.

Table 164 covers 252 compounds of the type T-2 wherein $R^1$ is trifluoromethoxy, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 165 covers 252 compounds of the type T-2 wherein $R^1$ is trifluoromethoxy, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 166 covers 252 compounds of the type T-2 wherein $R^1$ is trifluoromethoxy, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 167 covers 252 compounds of the type T-2 wherein $R^1$ is trifluoromethoxy, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 168 covers 252 compounds of the type T-2 wherein $R^1$ is trifluoromethoxy, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 169 covers 252 compounds of the type T-2 wherein $R^1$ is cyclopropyl, $R^4$ is hydrogen, $R^5$, $R^6$, $R^8$, $R^9$, $R^{11}$ and $R^{12}$ are hydrogen and $R^2$ and $R^3$ are as defined in Table 1

Table 170 covers 252 compounds of the type T-2 wherein $R^1$ is cyclopropyl, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 171 covers 252 compounds of the type T-2 wherein $R^1$ is cyclopropyl, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 172 covers 252 compounds of the type T-2 wherein $R^1$ is cyclopropyl, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 173 covers 252 compounds of the type T-2 wherein $R^1$ is cyclopropyl, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 174 covers 252 compounds of the type T-2 wherein $R^1$ is cyclopropyl, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 175 covers 252 compounds of the type T-2 wherein $R^1$ is cyclopropyl, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 176 covers 252 compounds of the type T-2 wherein $R^1$ is cyclopropyl, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 177 covers 252 compounds of the type T-2 wherein $R^1$ is cyclopropyl, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 178 covers 252 compounds of the type T-2 wherein $R^1$ is cyclopropyl, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 179 covers 252 compounds of the type T-2 wherein $R^1$ is cyclopropyl, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 180 covers 252 compounds of the type T-2 wherein $R^1$ is cyclopropyl, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 181 covers 252 compounds of the type T-2 wherein $R^1$ is chlorine, $R^4$ is hydrogen, $R^5$, $R^6$, $R^8$, $R^9$, $R^{11}$ and $R^{12}$ are hydrogen and $R^2$ and $R^3$ are as defined in Table 1

Table 182 covers 252 compounds of the type T-2 wherein $R^1$ is chlorine, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 183 covers 252 compounds of the type T-2 wherein $R^1$ is chlorine, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 184 covers 252 compounds of the type T-2 wherein $R^1$ is chlorine, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 185 covers 252 compounds of the type T-2 wherein $R^1$ is chlorine, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 186 covers 252 compounds of the type T-2 wherein $R^1$ is chlorine, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 187 covers 252 compounds of the type T-2 wherein $R^1$ is chlorine, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 188 covers 252 compounds of the type T-2 wherein $R^1$ is chlorine, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 189 covers 252 compounds of the type T-2 wherein $R^1$ is chlorine, $R^4$ is hydrogen, $R^5$ and $R^6$ are hydrogen, $R^8$ ismethoxymethyl, $R^9$, $R^{11}$ and $R^{12}$ are hydrogen and $R^2$ and $R^3$ are as defined in Table 1.

Table 190 covers 252 compounds of the type T-2 wherein $R^1$ is chlorine, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 191 covers 252 compounds of the type T-2 wherein $R^1$ is chlorine, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 192 covers 252 compounds of the type T-2 wherein $R^1$ is chlorine, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Example 7

Preparation of (1RS,2SR,6RS,7SR)-4-(3,5-dimethyl-biphenyl-4-yl)-5-oxo-10-oxa-tricyclo[5.2.1.0$^{2,6}$]dec-3-en-3-yl 2,2-dimethylpropionate

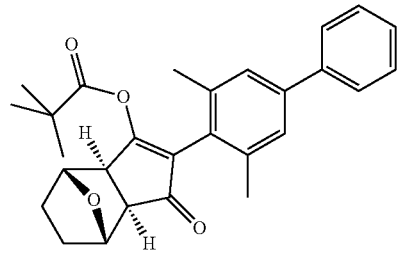 [SMILES: Cc1cc(-c2ccccc2)cc(C)c1C1=C(OC(=O)C(C)(C)C)[C@H]2[C@@H](C1=O)[C@@H]1CC[C@H]2O1]

To a solution of (1RS,2SR,6RS,7SR)-4-(3,5-dimethylbiphenyl-4-yl)-10-oxa-tricyclo-[5.2.1.0$^{2,6}$]decane-3,5-dione (80 mg, 0.23 mmol) in dichloromethane (5 ml) and triethylamine (140 µl, 1 mmol) is added pivaloyl chloride (124 µl, 1 mmol) at room temperature. The reaction mixture is stirred overnight at room temperature. Silica gel is added to the crude reaction mixture, the solvent is evaporated under reduced pressure and the residue is purified by column chromatography on silica gel to give (1RS,2SR,6RS,7SR)-4-(3,5-dimethylbiphenyl-4-yl)-5-oxo-10-oxa-tricyclo[5.2.1.0$^{2,6}$]dec-3-en-3-yl 2,2-dimethylpropionate.

$^1$H NMR (400 MHz) $\delta_H$ 7.62 (2H, d), 7.46 (t, 2H), 7.37 (1H, t), 7.32 (1H, s), 7.30 (1H, s), 4.82 (1H, d), 4.64 (1H, d), 3.53 (1H, d), 2.87 (1H, d), 2.25 (3H, s), 2.19 (3H, s), 2.00-1.86 (2H, m), 1.73-1.63 (2H, m), 1.16 (9H, s).

Additional compounds in Table P1 below are prepared by similar methods using appropriate starting materials.

TABLE P1

| Compound Number | Structure | ¹H nmr (CDCl₃ unless stated) or other physical data |
|---|---|---|
| P1 | 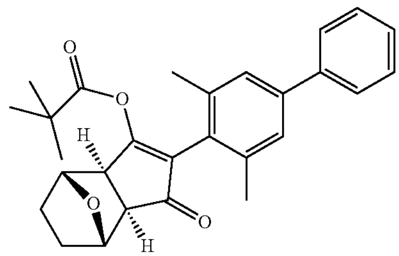 [SMILES: Cc1cc(-c2ccccc2)cc(C)c1C1=C(OC(=O)C(C)(C)C)[C@H]2[C@@H](C1=O)[C@@H]1CC[C@H]2O1] | $\delta_H$ 7.62 (2H, d), 7.46 (t, 2H), 7.37 (1H, t), 7.32 (1H, s), 7.30 (1H, s), 4.82 (1H, d), 4.64 (1H, d), 3.53 (1H, d), 2.87 (1H, d), 2.25 (3H, s), 2.19 (3H, s), 2.00-1.86 (2H, m), 1.73-1.63 (2H, m), 1.16 (9H, s). |
| P2 | 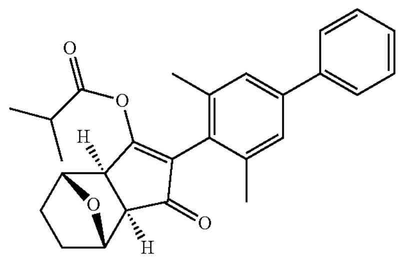 [SMILES: Cc1cc(-c2ccccc2)cc(C)c1C1=C(OC(=O)C(C)C)[C@H]2[C@@H](C1=O)[C@@H]1CC[C@H]2O1] | $\delta_H$ 7.57 (2H, d), 7.41 (2H, t), 7.32 (1H, t), 7.27 (1H, s), 7.25 (1H, s), 4.77 (1H, d), 4.60 (1H, d), 3.52 (1H, d), 2.82 (1H, d), 2.63 (1H, sept.), 2.20 (3H, s), 2.14 (3H, s), 1.95-1.81 (2H, m), 1.67-1.58 (2H, m), 1.13 (3H, d), 1.06 (3H, d). |
| P3 | 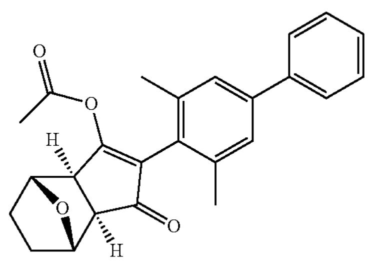 [SMILES: CC(=O)OC1=C(c2c(C)cc(-c3ccccc3)cc2C)C(=O)[C@@H]2[C@H]1[C@H]1CC[C@@H]2O1] | $\delta_H$ 7.57 (2H, d), 7.42 (2H, t), 7.32 (1H, t), 7.28 (1H, s), 7.26 (1H, s), 4.76 (1H, d), 4.61 (1H, d), 3.58 (1H, d), 2.82 (1H, d), 2.20 (3H, s), 2.17 (3H, s), 2.15 (3H, s), 1.95-1.81 (2H, m), 1.67-1.58 (2H, m). |
| P4 | 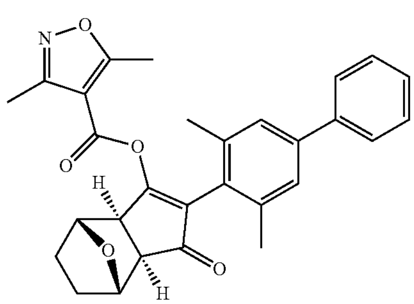 [SMILES: Cc1cc(-c2ccccc2)cc(C)c1C1=C(OC(=O)c2c(C)noc2C)[C@H]2[C@@H](C1=O)[C@@H]1CC[C@H]2O1] | $\delta_H$ 7.55 (2H, d), 7.42 (2H, t), 7.33 (1H, t), 7.29 (1H, s), 7.26 (1H, s), 4.81 (1H, d), 4.67 (1H, d), 3.81 (1H, d), 2.87 (1H, d), 2.36 (3H, s), 2.22 (3H, s), 2.20 (3H, s), 2.15 (3H, s), 1.99-1.84 (2H, m), 1.77-1.62 (1H, m). |
| P5 | 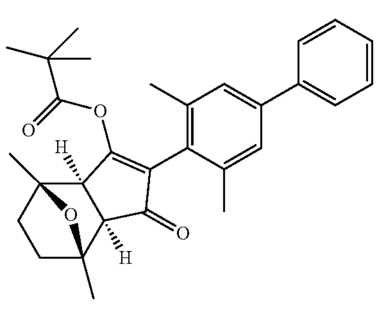 [SMILES: Cc1cc(-c2ccccc2)cc(C)c1C1=C(OC(=O)C(C)(C)C)[C@H]2[C@@H](C1=O)[C@]1(C)CC[C@@]2(C)O1] | $\delta_H$ 7.57 (2H, d), 7.41 (2H, t), 7.32 (1H, t), 7.27 (1H, s), 7.25 (1H, s), 3.48 (1H, d), 2.80 (1H, d), 2.24 (3H, s), 2.12 (3H, s), 1.84-1.67 (4H, m), 1.57 (6H, d), 1.06 (9H, s). |

TABLE P1-continued

| Compound Number | Structure | ¹H nmr (CDCl₃ unless stated) or other physical data |
|---|---|---|
| P6 | 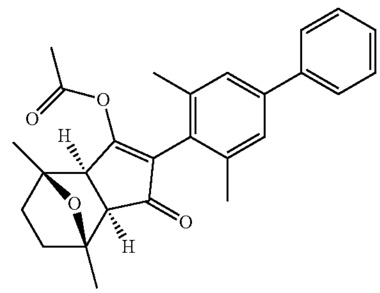 [SMILES: CC(=O)OC1=C(c2c(C)cc(-c3ccccc3)cc2C)C(=O)[C@@H]2[C@H]1[C@@]1(C)CC[C@]2(C)O1] | δ$_H$ 7.57 (2H, d), 7.41 (2H, t), 7.32 (1H, t), 7.29 (1H, s), 7.27 (1H, s), 3.63 (1H, d), 2.79 (1H, d), 2.23 (3H, s), 2.15 (3H, s), 2.13 (3H, s), 1.85-1.69 (4H, m), 1.57 (6H, d). |
| P7 | 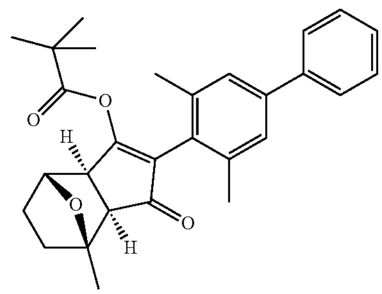 [SMILES: Cc1cc(-c2ccccc2)cc(C)c1C1=C(OC(=O)C(C)(C)C)[C@H]2[C@@H](C1=O)[C@]1(C)CC[C@H]2O1] | δ$_H$ 7.57 (2H, d), 7.41 (2H, t), 7.32 (1H, t), 7.27 (1H, s), 7.25 (1H, s), 4.49 (1H, d), 3.58 (1H, d), 2.70 (1H, d), 2.21 (3H, s), 2.14 (3H, s), 2.03-1.97 (1H, m), 1.72-1.61 (3H, m), 1.58 (3H, s), 1.11 (9H, s). |
| P8 | 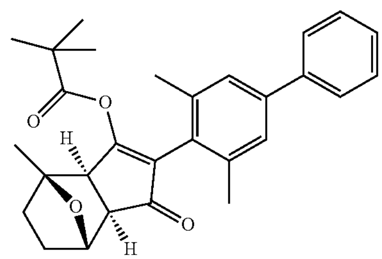 [SMILES: Cc1cc(-c2ccccc2)cc(C)c1C1=C(OC(=O)C(C)(C)C)[C@H]2[C@@H](C1=O)[C@@H]1CC[C@@]2(C)O1] | δ$_H$ 7.57 (2H, d), 7.41 (2H, t), 7.32 (1H, t), 7.27 (1H, s), 7.25 (1H, s), 4.72 (1H, d), 3.38 (1H, d), 2.94 (1H, d), 2.24 (3H, s), 2.12 (3H, s), 1.80-1.61 (4H, m), 1.60 (3H, s), 1.07 (9H, s). |
| P9 | 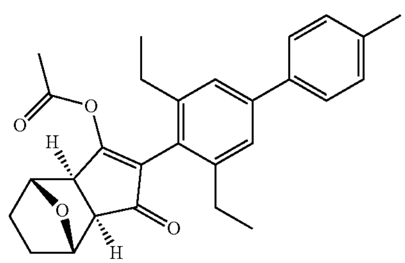 [SMILES: CCc1cc(-c2ccc(C)cc2)cc(CC)c1C1=C(OC(C)=O)[C@H]2[C@@H](C1=O)[C@@H]1CC[C@H]2O1] | δ$_H$ 7.47 (2H, d), 7.30 (2H, dd), 7.20 (2H, d), 4.70 (1H, d), 4.60 (1H, d), 3.60 (1H, d), 2.80 (1H, d), 2.39-2.49 (4H, m), 2.37 (3H, s), 2.17 (3H, s), 1.90-1.84 (2H, m), 1.67-1.60 (2H, m), 1.15-1.08 (6H, m) |
| P10 | 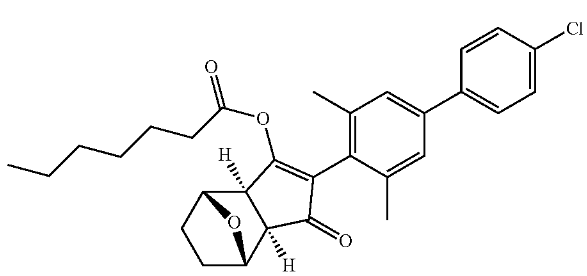 [SMILES: CCCCCCC(=O)OC1=C(c2c(C)cc(-c3ccc(Cl)cc3)cc2C)C(=O)[C@@H]2[C@H]1[C@H]1CC[C@@H]2O1] | δ$_H$ 7.54 (2H, d), 7.42 (2H, d), 7.28 (1H, s), 7.26 (1H, s), 4.80 (1H, d), 4.65 (1H, d), 3.56 (1H, d), 2.85 (1H, d), 2.24 (3H, s), 2.19 (3H, s), 1.99-1.85 (2H, m), 1.72-1.54 (4H, m), 1.40-1.22 (5H, m), 0.94-0.84 (4H, m). |

TABLE P1-continued

| Compound Number | Structure | ¹H nmr (CDCl₃ unless stated) or other physical data |
|---|---|---|
| P11 | 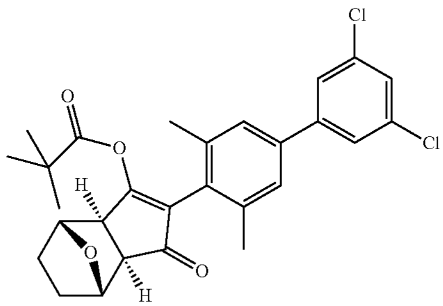 [SMILES: Cc1cc(-c2cc(Cl)cc(Cl)c2)cc(C)c1C1=C(OC(=O)C(C)(C)C)[C@H]2[C@@H](C1=O)[C@@H]1CC[C@H]2O1] | $\delta_H$ 7.50 (1H, d), 7.40 (1H, s), 7.30 (1H, d), 7.20 (2H, d), 4.80 (1H, d), 4.60 (1H, d), 3.50 (1H, d), 2.80 (1H, d), 2.20 (3H, s), 2.10 (3H, s), 1.85 (2H, m), 1.60 (2H, m), 1.10 (9H, s). |

Biological Examples

Monocotyledonous and dicotyledonous test plants were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 15 days later for post-emergence and 20 days for pre-emergence, the test was evaluated (100=total damage to plant; 0=no damage to plant).

Test Plants:

*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

| | | Pre-Emergence Activity | | | | | |
|---|---|---|---|---|---|---|---|
| Compound Number | Rate g/ha | ALOMY | AVEFA | LOLPE | SETFA | DIGSA | ECHCG |
| T2 | 250 | 70 | 40 | 50 | 80 | 70 | 90 |
| T3 | 250 | 70 | 80 | 80 | 100 | 100 | 100 |
| T4 | 250 | 60 | 50 | 60 | 100 | 100 | 100 |
| T6 | 250 | 50 | 0 | 70 | 100 | 80 | 100 |
| T7 | 250 | 90 | 40 | 40 | 100 | 100 | 100 |
| T8 | 250 | 90 | 50 | 80 | 100 | 100 | 100 |
| T9 | 250 | 70 | 50 | 80 | 50 | 60 | 100 |
| T10 | 250 | 70 | 70 | 80 | 100 | 100 | 100 |
| T11 | 250 | 70 | 60 | 80 | 100 | 90 | 100 |
| T12 | 250 | 70 | 20 | 60 | 100 | 100 | 90 |
| T13 | 250 | 40 | 20 | 30 | 80 | 80 | 70 |
| T14 | 250 | 10 | 20 | 40 | 100 | 90 | 90 |
| T15 | 250 | 20 | 10 | 20 | 80 | 90 | 100 |
| T17 | 250 | 0 | 0 | 20 | 80 | 90 | 90 |
| T18 | 250 | 50 | 20 | 80 | 90 | 100 | 90 |
| T19 | 250 | 70 | 70 | 60 | 90 | 100 | 90 |
| T21 | 250 | 50 | 50 | 60 | 100 | 90 | 100 |
| T23 | 250 | 40 | 60 | 70 | 100 | 100 | 100 |
| T24 | 250 | 10 | 30 | 30 | 100 | 100 | 100 |
| T26 | 250 | 0 | 0 | 0 | 70 | 70 | 70 |
| T27 | 250 | 0 | 30 | 30 | 40 | 40 | 60 |
| T28 | 250 | 0 | 30 | 40 | 20 | 30 | 0 |
| T29 | 250 | 10 | 0 | 30 | 50 | 40 | 0 |
| T31 | 250 | 0 | 50 | 20 | 10 | 30 | 60 |
| T32 | 250 | 30 | 0 | 60 | 100 | 30 | 70 |
| T33 | 250 | 20 | 0 | 50 | 80 | 70 | 70 |
| T37 | 250 | 20 | 30 | 50 | 80 | 100 | 80 |
| T38 | 250 | 0 | 30 | 50 | 90 | 30 | 100 |
| T40 | 250 | 10 | 10 | 0 | 70 | 100 | 50 |
| P1 | 250 | 100 | 70 | 100 | 90 | 100 | 100 |
| P2 | 250 | 100 | 70 | 90 | 100 | 100 | 80 |
| P3 | 250 | 100 | 60 | 100 | 100 | 100 | 80 |
| P4 | 250 | 100 | 50 | 90 | 100 | 100 | 100 |
| P5 | 250 | 100 | 0 | 70 | 100 | 100 | 70 |
| P6 | 250 | 80 | 30 | 70 | 100 | 100 | 100 |
| P7 | 250 | 100 | 90 | 100 | 100 | 100 | 90 |
| P8 | 250 | 100 | 90 | 100 | 100 | 100 | 90 |
| P9 | 250 | 50 | 60 | 70 | 60 | 40 | 100 |

| Compound Number | Rate g/ha | ALOMY | AVEFA | LOLPE | SETFA | DIGSA | ECHCG |
|---|---|---|---|---|---|---|---|
| T2 | 125 | 100 | 100 | 80 | 100 | 100 | 100 |
| T3 | 125 | 100 | 90 | 80 | 90 | 90 | 90 |
| T4 | 125 | 80 | 60 | 80 | 100 | 100 | 100 |
| T6 | 125 | 80 | 30 | 50 | 60 | 30 | 70 |
| T7 | 125 | 70 | 60 | 60 | 90 | 80 | 100 |
| T8 | 125 | 100 | 90 | 70 | 100 | 100 | 100 |
| T9 | 125 | 80 | 20 | 80 | 70 | 80 | 100 |
| T10 | 125 | 90 | 90 | 90 | 100 | 100 | 100 |
| T11 | 125 | 100 | 90 | 50 | 100 | 90 | 100 |
| T12 | 125 | 100 | 100 | 80 | 100 | 100 | 100 |
| T13 | 125 | 50 | 30 | 40 | 80 | 10 | 100 |
| T14 | 125 | 90 | 80 | 30 | 100 | 100 | 100 |
| T15 | 125 | 100 | 90 | 40 | 100 | 100 | 100 |
| T17 | 125 | 90 | 90 | 40 | 100 | 100 | 100 |
| T18 | 125 | 100 | 100 | 70 | 100 | 100 | 100 |
| T19 | 125 | 100 | 100 | 90 | 100 | 100 | 100 |
| T21 | 125 | 80 | 80 | 40 | 90 | 100 | 100 |
| T23 | 125 | 100 | 100 | 70 | 90 | 90 | 100 |
| T24 | 125 | 90 | 90 | 60 | 100 | 100 | 100 |
| T26 | 125 | 30 | 20 | 30 | 100 | 90 | 90 |
| T27 | 125 | 70 | 40 | 70 | 70 | 60 | 70 |
| T28 | 125 | 90 | 90 | 50 | 100 | 70 | 100 |
| T29 | 125 | 90 | 90 | 50 | 100 | 100 | 100 |
| T31 | 125 | 90 | 80 | 40 | 100 | 100 | 100 |
| T32 | 125 | 70 | 70 | 60 | 70 | 70 | 100 |
| T33 | 125 | 100 | 100 | 80 | 100 | 100 | 100 |
| T37 | 125 | 90 | 100 | 70 | 100 | 100 | 100 |
| T38 | 125 | 100 | 90 | 50 | 80 | 100 | 100 |
| T40 | 125 | 60 | 40 | 30 | 80 | 100 | 100 |
| P1 | 125 | 100 | 50 | 90 | 80 | 80 | 100 |
| P2 | 125 | 100 | 80 | 90 | 100 | 90 | 100 |
| P3 | 125 | 100 | 80 | 100 | 90 | 80 | 100 |
| P4 | 125 | 100 | 90 | 90 | 80 | 80 | 100 |
| P5 | 125 | 70 | 20 | 40 | 90 | 100 | 100 |
| P6 | 125 | 70 | 50 | 60 | 100 | 90 | 100 |
| P7 | 125 | 100 | 100 | 80 | 100 | 100 | 100 |
| P8 | 125 | 100 | 100 | 80 | 100 | 100 | 100 |
| P9 | 125 | 80 | 80 | 80 | 90 | 100 | 100 |

What is claimed is:

1. A compound of formula I

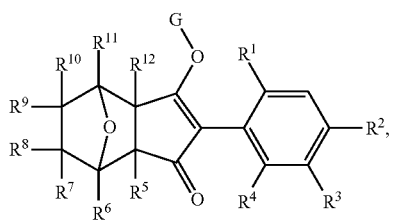

wherein $R^1$ is methyl, ethyl, n-propyl, isopropyl, halomethyl, haloethyl, halogen, vinyl, ethynyl, methoxy, ethoxy, halomethoxy, haloethoxy or cyclopropyl, $R^2$ and $R^3$ are independently of each other hydrogen; phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano; or heteroaryl or heteroaryl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, wherein one of $R^2$ and $R^3$ is optionally substituted phenyl or optionally substituted heteroaryl, $R^4$ is hydrogen, methyl, ethyl, n-propyl, isopropyl, halomethyl, haloethyl, halogen, vinyl, ethynyl, methoxy, ethoxy, halomethoxy or haloethoxy, $R^5$ and $R^{12}$ are independently of each other hydrogen or $C_1$-$C_3$alkyl, and $R^6$ and $R^{11}$ are independently of each other hydrogen, halogen, cyano, $C_1$-$C_6$alkyl, methyl substituted by $C_1$-$C_3$alkoxy, $CF_3$, $CF_2H$, $FCH_2$, $CH_3CHF$, $(CH_3)_2CF$, $CF_3CH_2$, $CHF_2CH_2$, or a group $COR^{13}$, $CO_2R^{14}$ or $CONR^{15}R^{16}$, $CR^{17}=NOR^{18}$ or $CR^{19}=NNR^{20}R^{21}$, wherein $R^{13}$, $R^{14}$, $R^{15}$ and $R^{16}$ are $C_1$-$C_6$alkyl, $R^{17}$ and $R^{19}$ are hydrogen or $C_1$-$C_3$ alkyl, $R^{18}$ is $C_1$-$C_3$ alkyl, and $R^{20}$ and $R^{21}$ are independently of each other hydrogen or $C_1$-$C_3$alkyl, and $R^7$, $R^8$, $R^9$ and $R^{10}$ are independently of each other hydrogen, halogen, hydroxyl, formyl, amino, cyano, nitro, $C_1$-$C_6$alkyl, $C_1$-$C_6$alkoxy$C_1$-$C_6$alkyl, $CF_3$, $CF_2H$, $FCH_2$, $CH_3CHF$, $(CH_3)_2CF$, $CF_3CH_2$, $CHF_2CH_2$, $C_2$-$C_6$alkenyl, $C_2$-$C_6$alkynyl, $C_1$-$C_6$alkoxy, $C_1$-$C_6$alkylthio, $C_1$-$C_6$alkylsulfinyl, $C_1$-$C_6$alkylsulfonyl, $C_3$-$C_7$ cycloalkyl, a 3-7 membered heterocyclyl, optionally substituted phenyl, optionally substituted heteroaryl, $CO_2R^{14}$, $CONR^{14}R^{15}$, or $CR^{17}=NOR^{18}$, wherein $R^{14}$ is hydrogen or $C_1$-$C_6$alkyl and $R^{15}$ is hydrogen or $C_1$-$C_6$alkyl, and wherein $R^{17}$ and $R^{18}$ are as defined above, or $R^7$ and $R^8$ together form a unit =O or =$NR^{27}$, wherein $R^{27}$ is $C_{1-3}$alkoxy, or $R^7$ and $R^{10}$ together form a bond, G is hydrogen, an alkali metal, alkaline earth metal, sulfonium, ammonium or a latentiating group;

and wherein, when G is a latentiating group, then G is selected from the groups —C($X^a$)—$R^a$, C($X^b$)—$X^c$—$R^b$, C($X^d$)—N($R^c$)—$R^d$, —$SO_2$—$R^e$, —P($X^e$)($R^f$)—$R^g$ and $CH_2$—$X^f$—$R^h$;

wherein $X^a$, $X^b$, $X^c$, $X^d$, $X^e$ and $X^f$ are independently of each other oxygen or sulfur; and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$-nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, henyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; ID henylamino or ID henylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, optionally containing one heteroatom selected from O and S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_8$-trialkylsilyl$C_1$-$C_5$alkyl, henyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or ID phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkoxy, $C_1$-$C_{10}$cyanoalkyl, $C_1$-$C_{10}$-nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein:

substituted aryl moieties or substituted heteroaryl groups are, unless otherwise indicated, substituted by one or more substituents independently selected from halogen, cyano, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, nitro and cyano;

and wherein:

"aryl" means phenyl; and

"heteroaryl" means an aromatic ring system containing at least one heteroatom and consisting either of a single ring or of two fused rings.

2. A compound according to claim 1, wherein $R^1$ is methyl, ethyl, vinyl, ethynyl, cyclopropyl, difluoromethoxy or trifluoromethoxy.

3. A compound Compounds according to claim 1, wherein:
$R^2$ is hydrogen, and $R^3$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, or
$R^2$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, and $R^3$ is hydrogen.

4. A compound according to claim 1, wherein $R^4$ is hydrogen, methyl, ethyl, vinyl or ethynyl.

5. A compound according to claim 1, wherein $R^5$ and $R^{12}$ are hydrogen.

6. A compound according to claim 1, wherein $R^6$ and $R^{11}$ are independently of each other hydrogen, methyl or methyl substituted by $C_1$-$C_3$alkoxy.

7. A compound according to claim 1, wherein
$R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, 3-7 membered heterocyclyl or $CR^{17}$=$NOR^{18}$, wherein
$R^{17}$ is hydrogen or $C_1$-$C_3$ alkyl, and
$R^{18}$ is $C_1$-$C_3$ alkyl.

8. A compound according to claim 1, wherein $R^7$, $R^8$, $R^9$ and $R^{10}$ are independently of each other hydrogen, $C_1$-$C_6$alkyl, $C_2$-$C_6$alkenyl, $C_1$-$C_6$alkoxy or $C_1$-$C_6$alkoxy$C_1$-$C_6$alkyl.

9. A compound according to claim 1, wherein $R^1$ is methyl or ethyl.

10. A compound according to claim 1, wherein G denotes hydrogen, an alkali metal or alkaline earth metal, or a latentiating group as defined in claim 1.

11. A process for the preparation of a compound of formula I as defined in claim 1, wherein G is H and $R^7$ and $R^{10}$ form a bond, which comprises reacting a compound of the formula (OO)

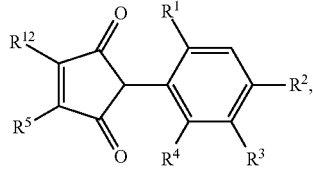

(OO)

wherein $R^1$ to $R^5$ and $R^{12}$ are as defined in claim 1, with a compound of the formula (H)

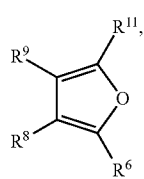

(H)

wherein $R^6$, $R^8$, $R^9$ and $R^{11}$ are as defined in claim 1, in the presence or absence of a Lewis acid as catalyst and in the presence or absence of a solvent.

12. A compound of the formula (OO)

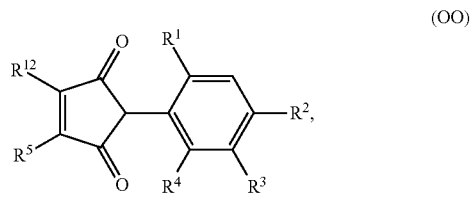

(OO)

wherein $R^1$ to $R^5$ and $R^{12}$ are as defined in claim 1.

13. A herbicidal composition, which, in addition to comprising formulation assistants, comprises a herbicidally effective amount of a compound of formula I as defined in claim 1.

14. A composition according to claim 13, which, in addition to comprising the compound of formula I, comprises a further herbicide as mixing partner and, optionally, a safener.

15. A method of controlling grasses and weeds in crops of useful plants, which comprises applying a herbicidally effective amount of a compound of formula I as defined in claim 1, or of a composition comprising such a compound, to the plants or to the locus thereof.

16. A method according to claim 15, which comprises applying a herbicidally effective amount of a composition comprising the compound to the plants or to the locus thereof, and wherein the crops of useful plants are wheat, barley, rice, corn, rape, sugarbeet, sugarcane, soybean, cotton, sunflower, or peanut.

17. A compound according to claim 1, wherein $R^4$ is hydrogen, methyl or ethyl.

18. A compound according to claim 1, wherein, when G is a latentiating group, then G is a group —C($X^a$)—$R^a$ or —C($X^b$)—$X^c$—$R^b$, wherein the meanings of $X^a$, $R^a$, $X^b$, $X^c$ and $R^b$ are defined in claim 1.

19. A compound according to claim 1, wherein:
$R^5$ and $R^{12}$ are hydrogen,
$R^6$ and $R^{11}$ are independently of each other hydrogen, methyl or methyl substituted by $C_1$-$C_3$alkoxy, and
$R^7$, $R^8$, $R^9$ and $R^{10}$ are independently of each other hydrogen, $C_1$-$C_6$alkyl, $C_2$-$C_6$alkenyl, $C_1$-$C_6$alkoxy or $C_1$-$C_6$alkoxy$C_1$-$C_6$alkyl.

20. A compound according to claim 1, wherein:
$R^5$ and $R^{12}$ are hydrogen,
$R^6$ and $R^{11}$ are independently of each other hydrogen, methyl or methyl substituted by $C_1$-$C_3$alkoxy, and
$R^7$, $R^8$, $R^9$ and $R^{10}$ are hydrogen.

* * * * *